United States Patent
Shi et al.

(10) Patent No.: US 10,023,519 B2
(45) Date of Patent: Jul. 17, 2018

(54) CYCLOBUTANE CONTAINING CARBOXYLIC ACID GPR120 MODULATORS

(71) Applicant: BRISTOL-MYERS SQUIBB COMPANY, Princeton, NJ (US)

(72) Inventors: Yan Shi, Flourtown, PA (US); Ying Wang, Belle Mead, NJ (US); Peter T. W. Cheng, Princeton, NJ (US); Shung C. Wu, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/509,225

(22) PCT Filed: Sep. 8, 2015

(86) PCT No.: PCT/US2015/048782
§ 371 (c)(1),
(2) Date: Mar. 7, 2017

(87) PCT Pub. No.: WO2016/040223
PCT Pub. Date: Mar. 17, 2016

(65) Prior Publication Data
US 2017/0247311 A1 Aug. 31, 2017

Related U.S. Application Data

(60) Provisional application No. 62/047,849, filed on Sep. 9, 2014.

(51) Int. Cl.
| | |
|---|---|
| C07C 59/72 | (2006.01) |
| C07C 59/90 | (2006.01) |
| C07D 309/12 | (2006.01) |
| C07D 237/14 | (2006.01) |
| C07D 213/68 | (2006.01) |
| C07D 307/79 | (2006.01) |
| C07D 213/65 | (2006.01) |
| C07D 271/06 | (2006.01) |
| C07D 213/70 | (2006.01) |
| C07D 213/64 | (2006.01) |
| C07D 277/24 | (2006.01) |
| A61K 45/06 | (2006.01) |
| A61K 31/192 | (2006.01) |
| A61K 31/4418 | (2006.01) |
| A61K 31/4245 | (2006.01) |
| A61K 31/426 | (2006.01) |
| A61K 31/343 | (2006.01) |
| A61K 31/50 | (2006.01) |
| A61K 31/351 | (2006.01) |

(52) U.S. Cl.
CPC ............ *C07C 59/72* (2013.01); *A61K 31/192* (2013.01); *A61K 31/343* (2013.01); *A61K 31/351* (2013.01); *A61K 31/426* (2013.01); *A61K 31/4245* (2013.01); *A61K 31/4418* (2013.01); *A61K 31/50* (2013.01); *A61K 45/06* (2013.01); *C07C 59/90* (2013.01); *C07D 213/64* (2013.01); *C07D 213/65* (2013.01); *C07D 213/68* (2013.01); *C07D 213/70* (2013.01); *C07D 237/14* (2013.01); *C07D 271/06* (2013.01); *C07D 277/24* (2013.01); *C07D 307/79* (2013.01); *C07D 309/12* (2013.01); *C07C 2601/02* (2017.05); *C07C 2601/04* (2017.05); *C07C 2601/08* (2017.05); *C07C 2602/50* (2017.05)

(58) Field of Classification Search
CPC ....... C07C 59/72; C07C 59/90; C07D 309/12; C07D 237/14; C07D 213/68; C07D 307/79; C07D 213/65; C07D 271/06; C07D 213/70; C07D 213/64; C07D 277/24

See application file for complete search history.

(56) References Cited

U.S. PATENT DOCUMENTS

| | | | |
|---|---|---|---|
| 8,962,660 B2 | 2/2015 | Zhang et al. | |
| 9,518,000 B2 | 12/2016 | Shi et al. | |
| 9,598,390 B2 | 3/2017 | Shi et al. | |
| 2013/0331372 A1* | 12/2013 | Lu .......................... | A61K 31/42 514/210.18 |

FOREIGN PATENT DOCUMENTS

| | | |
|---|---|---|
| EP | 1 916 234 A1 | 4/2008 |
| WO | WO2008/134693 A1 | 11/2008 |

(Continued)

OTHER PUBLICATIONS

CAS Registry Entry for Registry No. 1520396-81-9, which entered STN on Jan. 15, 2014.*

(Continued)

*Primary Examiner* — Matthew P Coughlin

(74) *Attorney, Agent, or Firm* — Jing G. Sun

(57) ABSTRACT

The present invention provides compounds of Formula (I): or a stereoisomer, or a pharmaceutically acceptable salt thereof, wherein all of the variables are as defined herein. These compounds are GPR120 G protein-coupled receptor modulators which may be used as medicaments.

(I)

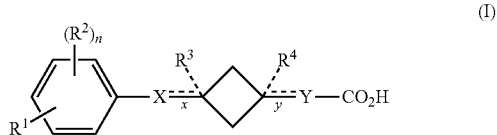

20 Claims, No Drawings

(56) References Cited

FOREIGN PATENT DOCUMENTS

| WO | WO2012/124744 | A1 | 9/2012 | |
|----|----|----|----|----|
| WO | WO 2014099836 | A1 * | 6/2014 | ........... C07D 413/14 |
| WO | WO2014/151247 | A1 | 9/2014 | |
| WO | WO2014/159794 | A2 | 10/2014 | |
| WO | WO2014/159802 | A1 | 10/2014 | |
| WO | WO2016/040222 | A1 | 3/2016 | |
| WO | WO2016/040225 | A1 | 3/2016 | |

OTHER PUBLICATIONS

CAS Registry Entry for Registry No. 1500715-74-1, which entered STN on Dec. 22, 2013.*

U.S. Appl. No. 15/509,214, filed Mar. 7, 2017, Shi, et al.

U.S. Appl. No. 15/509,237, filed Mar. 7, 2017, Cheng et al.

Arbeeny, C. et al., "The Metabolic Syndrome: From Pathophysiology to Novel Treatment Strategies", Current Med. Chem- Imm. Endoc. & Metab. Agents, vol. 1, pp. 1024 (2001).

Barlind, J., et al., "Identification and design of a novel series of MGAT2 inhibitors", Bioorganic & Medicinal Chemistry Letters, vol. 23, pp. 2721-2726 (2013).

Ford, Earl et al., "Prevalence of the Metabolic Syndrome Among Us Adults", JAMA, vol. 287(3), pp. 356-359 ( 2002).

Ichimura, A. et al., "Dysfunction of lipid sensor GPR120 leads to obesity in both mouse and human", Nature, vol. 483, pp. 350-354 (2012).

Im, Dong-Soon, "Omega-3 fatty acids in anti-inflammation (pro-resolution) and GPCRs", Progress in Lipid Research, vol. 51, pp. 232-237 (2012).

Miyauchi, S., "Distribution and regulation of protein expression of the free fatty acid receptor GPR120", Naunyn-Schmied Arch Pharmacol, vol. 379, pp. 427-434 (2009).

Oh, Da Young, et al., "GPR120 is an Omega-3 Fatty Acid Receptor Mediating Potent Anti-inflammatory and Insulin-Sensitizing Effects", Cell, vol. 142, pp. 687-698 (2010).

Shimpukade, B. et al., "Discovery of a Potent and Selective GPR120 Agonist", J. of Medicinal Chemistry, Vo. 55, pp. 4511-4515 (2012).

* cited by examiner

CYCLOBUTANE CONTAINING CARBOXYLIC ACID GPR120 MODULATORS

CROSS-REFERENCE TO RELATED APPLICATIONS

This application claims priority to U.S. Provisional Application Ser. No. 62/047,849, filed Sep. 9, 2014; the entire content of which is incorporated herein reference.

FIELD OF THE INVENTION

The present invention provides novel cyclobutane containing carboxylic acid compounds, and their analogues thereof, which are GPR120 G protein-coupled receptor modulators, compositions containing them, and methods of using them, for example, for the treatment of diabetes and related conditions.

BACKGROUND OF THE INVENTION

Diabetes mellitus is a progressively debilitating disorder of epidemic proportions leading to various micro- and macrovascular complications and morbidity. The most common type of diabetes, type 2 diabetes, is characterized by increasing insulin resistance associated with inadequate insulin secretion after a period of compensatory hyperinsulinemia. Polyunsaturated fatty acids (PUFAs) such as omega-3 fatty acids are known to improve sensitivity to insulin. Insulin sensitivity can be improved by exerting anti-inflammatory effects in monocytes and/or macrophages and/or by enhancing glucose uptake in adipose and muscle. GPR120 is a membrane-bound receptor responsive to PUFAs which is preferentially expressed in adipose tissue and monocytes/macrophages. To decrease the medical burden of type 2 diabetes through enhanced glycemic control, GPR120 modulator compounds hold the promise of exerting a sensitizing effect to insulin as well as potential combination with a broad range of anti-diabetic drugs.

The present invention relates to novel cyclobutane containing carboxylic acid compounds which have the ability to modulate GPR120. Such compounds are therefore potentially useful for the treatment or prophylaxis of diabetes and related conditions.

SUMMARY OF THE INVENTION

The present invention provides cyclobutane containing carboxylic acid compounds, and their analogues thereof, which are useful as GPR120 modulators, including stereoisomers, tautomers, pharmaceutically acceptable salts, polymorphs, or solvates thereof.

The present invention also provides processes and intermediates for making the compounds of the present invention or stereoisomers, tautomers, pharmaceutically acceptable salts, polymorphs, or solvates thereof.

The present invention also provides pharmaceutical compositions comprising a pharmaceutically acceptable carrier and at least one of the compounds of the present invention or stereoisomers, tautomers, pharmaceutically acceptable salts, polymorphs, or solvates thereof.

The compounds of the invention may be used in the treatment of multiple diseases or disorders associated with GPR120, such as diabetes and related conditions, microvascular complications associated with diabetes, the macrovascular complications associated with diabetes, cardiovascular diseases, Metabolic Syndrome and its component conditions, disorders of glucose metabolism, obesity and other maladies.

The compounds of the invention may be used in therapy.

The compounds of the invention may be used for the manufacture of a medicament for the treatment of multiple diseases or disorders associated with GPR120.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

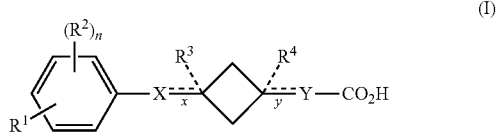

or a stereoisomer, a tautomer, a pharmaceutically acceptable salt, a polymorph, a solvate or a hydrate thereof, wherein:

----- designates a single or double bond;

x and y can be both a single bond; when x is a double bond, then y is a single bond and $R^3$ is absent; when y is a double bond, then x is a single bond and $R^4$ is absent;

X is independently selected from: a bond, O, $CH_2$, $-CH_2CH_2-$, $-OCH_2-$, and $-CH_2O-$;

Y is independently a bond, a hydrocarbon linker substituted with 0-2 $R^a$, a hydrocarbon-heteroatom linker substituted with 0-2 $R^a$, or $-(CH_2)_{1-3}-(O)_{0-1}-(CH_2)_{1-3}-(C_{3-4}$ cycloalkyl substituted with 0-2 $R^a)-(CH_2)_{0-2}-$; wherein said hydrocarbon linker has one to six carbon atoms and may be straight or branched, saturated or unsaturated; and said hydrocarbon-heteroatom linker has one to four carbon atoms and one group selected from O, CO, S, NH, CONH, and NHCO;

W is independently selected from: a bond and O;

$R^1$ is $-W-R^5$;

$R^2$, at each occurrence, is independently selected from: halogen, $C_{1-6}$ alkyl, $C_{1-4}$ alkoxy, $C_{1-4}$ alkylthio, $C_{1-4}$ haloalkyl, $C_{1-6}$ haloalkoxy, and $C_{1-4}$ haloalkylthio;

$R^3$ and $R^4$, at each occurrence, are independently selected from: H, $C_{1-4}$ alkyl, and $C_{1-4}$ alkoxy;

$R^3$ may combine with X to form a 3- to 4 carbocycle;

$R^4$ may combine with Y to form a 3- to 4 carbocycle;

$R^5$ is independently selected from: $C_{3-10}$ carbocycle, pyridyl, thiazolyl and dihydrobenzofuranyl; wherein each moiety is substituted with 0-1 $R^6$ and 0-3 $R^7$;

$R^6$ is independently selected from: $C_{1-6}$ alkyl, $C_{1-6}$ alkoxy, $C_{1-6}$ alkylthio, $C_{1-6}$ haloalkyl, $C_{1-6}$ haloalkoxy, $C_{1-6}$ haloalkylthio and $-(X_1)_{0-1}-(CH_2)_{0-2}-R^8$;

$X_1$ is independently selected from: O, S, NH and CO;

$R^7$, at each occurrence, is independently selected from: halogen, $C_{1-4}$ alkyl and $C_{1-4}$ alkoxy;

$R^8$ is independently selected from: $C_{3-6}$ carbocycle and a 5- to 6-membered heterocycle comprising carbon atoms and 1-4 heteroatoms selected from N, $NR^b$, O, and S; wherein said carbocycle and heterocycle are substituted with 0-3 $R^c$;

$R^a$, at each occurrence, is independently selected from: halogen, OH, $C_{1-4}$ alkyl, $C_{1-4}$ haloalkyl, and $C_{1-4}$ alkoxy;

$R^b$, at each occurrence, is independently selected from: H, $C_{1-4}$ alkyl, and $—(CH_2)_{0-2}$-phenyl;

$R^c$, at each occurrence, is independently selected from: halogen, $C_{1-4}$ alkyl, $C_{1-4}$ alkoxy, $C_{1-4}$ alkylthio, $C_{1-4}$ haloalkyl, $C_{1-4}$ haloalkoxy, and COPh; and n is independently 0, 1, or 2.

In a second aspect, the present invention includes a compound of Formula (II):

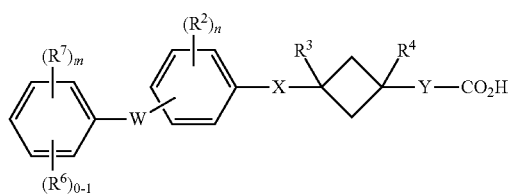

(II)

or a stereoisomer, a tautomer, a pharmaceutically acceptable salt, a polymorph, a solvate or a hydrate thereof, within the scope of the first aspect, wherein X is independently selected from: a bond, O, $CH_2$, $—OCH_2—$, and $—CH_2O—$;

Y is independently selected from: a bond, $—(CH_2)_{0-3}O(CH_2)_{1-2}—$, $—(CH_2)_{1-3}—$,

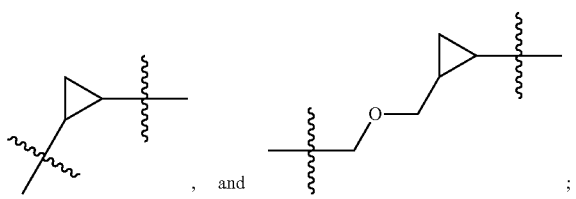 [SMILES: *C1CC1* ; *COCC1CC1*]

, and                ;

W is independently selected from: a bond and O;

$R^2$, at each occurrence, is independently selected from: halogen, $C_{1-4}$ alkyl, and $C_{1-4}$ alkoxy;

$R^3$ and $R^4$, at each occurrence, are independently selected from: H, $C_{1-4}$ alkyl, and $C_{1-4}$ alkoxy;

$R^6$ is independently selected from: $C_{1-4}$ alkoxy, $C_{1-4}$ haloalkoxy, Bn, and $—(O)_{0-1}—R^8$;

$R^7$, at each occurrence, is independently selected from: halogen, $C_{1-4}$ alkyl, and $C_{1-4}$ alkoxy;

$R^8$ is independently selected from: $C_{3-6}$ cycloalkyl, phenyl, tetrahydropyranyl, oxadiazolyl, thiazolyl, pyridyl, and pyridazinyl; wherein each moiety is substituted with 0-2 $R^c$;

$R^c$, at each occurrence, is independently selected from: halogen, $C_{1-4}$ alkyl, $C_{1-4}$ alkoxy, $C_{1-4}$ alkylthio, $C_{1-4}$ haloalkyl, $C_{1-4}$ haloalkoxy, and COPh; and m and n, at each occurrence, are independently 0, 1, or 2.

In a third aspect, the present invention includes a compound of Formula (I) or (II), or a stereoisomer, a tautomer, a pharmaceutically acceptable salt, a polymorph, a solvate or a hydrate thereof, within the scope of any of the above aspects, wherein:

Y is independently selected from: a bond, $—(CH_2)_{0-3}O(CH_2)_{1-2}—$, and $—(CH_2)_{1-3}—$;

W is O;

$R^3$ and $R^4$ are H; and m and n, at each occurrence, are independently 0 or 1.

In a fourth aspect, the present invention includes a compound of Formula (I) or (II), or a stereoisomer, a tautomer, a pharmaceutically acceptable salt, a polymorph, a solvate or a hydrate thereof, within the scope of any of the above aspects, wherein:

$R^6$ is independently selected from: Bn and $—(O)_{0-1}—R^8$;

$R^8$ is independently selected from: phenyl and pyridyl; wherein each moiety is substituted with 0-2 $R^c$; and $R^c$, at each occurrence, is independently selected from: halogen, $C_{1-4}$ alkyl, $C_{1-4}$ alkoxy, $C_{1-4}$ haloalkyl, and $C_{1-4}$ haloalkoxy.

In a fifth aspect, the present invention provides a compound selected from the exemplified examples within the scope of the first aspect, or a stereoisomer, a tautomer, a pharmaceutically acceptable salt, a polymorph, a solvate or a hydrate thereof.

In another aspect, the present invention provides a compound selected from any subset list of compounds within the scope of any of the above aspects.

In another aspect, X is a bond.

In another aspect, X is independently selected from: O, $CH_2$, $—OCH_2—$, and $—CH_2O—$.

In another aspect, $R^1$ is independently phenyl substituted with 0-4 $R^3$ and 0-1 $R^4$.

In another embodiment, the compounds of the present invention have hGPR120 $EC_{50}$ values $\leq 10$ μM.

In another embodiment, the compounds of the present invention have hGPR120 $EC_{50}$ values $\leq 5$ μM.

In another embodiment, the compounds of the present invention have hGPR120 $EC_{50}$ values $\leq 1$ μM.

In another embodiment, the compounds of the present invention have hGPR120 $EC_{50}$ values $\leq 0.5$ μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a pharmaceutical composition further comprising additional therapeutic agent(s). Examples of additional therapeutic agent(s), according to the present invention include, but are not limited to, anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-pancreatitis agents, lipid lowering agents, anorectic agents and appetite suppressants.

In a preferred embodiment, the present invention provides pharmaceutical composition, wherein the additional therapeutic agents are, for example, a dipeptidyl peptidase-IV (DPP4) inhibitor (for example a member selected from saxagliptin, sitagliptin, vildagliptin, linagliptin and alogliptin), a sodium-glucose transporter-2 (SGLT2) inhibitor (for example a member selected from dapagliflozin, canagliflozin, empagliflozin and remagliflozin), a GPR40/FFAR1 (Free fatty acid receptor 1) agonist (for example, TAK-875), and/or an MGAT2 (monoacylglycerol transferase 2) inhibitor (for example, compounds from WO 2012/124744, or compound (S)-10 from Bioorg. Med. Chem. Lett. (2013), doi: http://dx.doi.org/10.1016/j.bmcl.2013.02.084).

In a preferred embodiment, the present invention provides pharmaceutical composition, wherein the additional therapeutic agents are, for example, a dipeptidyl peptidase-IV inhibitor, a sodium-glucose transporter-2 inhibitor and an 11b-HSD-1 inhibitor.

In another embodiment, the present invention provides a method for the treatment of multiple diseases or disorders associated with GPR120, comprising administering to a patient in need of such treatment a therapeutically effective amount of at least one of the compounds of the present invention, alone, or, optionally, in combination with another compound of the present invention and/or at least one other type of therapeutic agent.

Examples of diseases or disorders associated with the activity of the GPR120 that can be prevented, modulated, or treated according to the present invention include, but are not limited to, diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases such as NASH (Non-Alcoholic SteatoHepatitis), NAFLD (Non-Alcoholic Fatty Liver Disease) and liver cirrhosis.

In another embodiment, the present invention provides a method for the treatment of diabetes, hyperglycemia, gestational diabetes, obesity, dyslipidemia and hypertension, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of diabetes, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of hyperglycemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of obesity, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of dyslipidemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of multiple diseases or disorders associated with GPR120.

In another embodiment, the present invention also provides the use of a compound of the present invention for the manufacture of a medicament for the treatment of multiple diseases or disorders associated with GPR120.

In another embodiment, the present invention provides a method for the treatment of multiple diseases or disorders associated with GPR120, comprising administering to a patient in need thereof a therapeutically effective amount of a first and second therapeutic agent, wherein the first therapeutic agent is a compound of the present invention. Preferably, the second therapeutic agent, for example, dipeptidyl peptidase-IV (DPP4) inhibitor (for example a member selected from saxagliptin, sitagliptin, linagliptin, vildagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of multiple diseases or disorders associated with GPR120.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR120 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the GPR120 receptor modulator of the present invention include, but are not limited to, insulin secretagogues or insulin sensitizers, other GPR120 receptor modulators, or other antidiabetic agents. These agents include, but are not limited to, dipeptidyl peptidase IV (DP4) inhibitors (for example, sitagliptin, saxagliptin, linagliptin, alogliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, peliglitazar, tesaglitazar and aleglitazar), glucokinase activators (for example, PF-04937319 and AMG-151), GPR119 receptor modulators (for example, MBX-2952, PSN821, and APD597), sodium-glucose transporter-2 (SGLT2) inhibitors (for example, dapagliflozin, canagliflozin, empagliflozin and remagliflozin), GPR40 receptor agonists (e.g., TAK-875), amylin analogs such as pramlintide, and/or insulin.

The GPR120 receptor modulator of the present invention may also be optionally employed in combination with agents for treating complication of diabetes. These agents include PKC inhibitors and/or AGE inhibitors.

The GPR120 receptor modulator of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, MGAT2 inhibitors and the like. The GPR120 receptor modulator of the present invention may also be employed in combination with an agonist of the glucagon-like peptide-1 receptor (GLP-1 R), such as exenatide, liraglutide, GLP-1(1-36) amide, GLP-1(7-36) amide, GLP-1(7-37), which may be administered via injection, intranasal, or by transdermal or buccal devices.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. The term "stereoisomer(s)" refers to compound(s) which have identical chemical constitution, but differ with regard to the arrangement of the atoms or groups in space. Unless otherwise indicated, all chiral (enantiomeric and diastereomeric) and racemic forms are within the scope of the invention. The term "chiral" refers to molecules which have the property of non-superimposability of the mirror image partner, while the term "achiral" refers to molecules which are superimposable on their mirror image partner. The terms "racemic mixture" and "racemate" refer to an equimolar mixture of two enantiomeric species, devoid of optical activity.

Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms.

Optically active forms may be prepared by resolution of stereoisomeric forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Unless otherwise indicated, any heteroatom with unsatisfied valences is assumed to have hydrogen atoms sufficient to satisfy the valences.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable.

Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), calcium ($Ca^{2+}$) ammonium ($R_nNH_m+$ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of the present invention can form salts which are also within the scope of this invention. Unless otherwise indicated, reference to an inventive compound is understood to include reference to one or more salts thereof. Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984);

f) Rautio, J. et al., *Nature Rev. Drug Discovery*, 7:255-270 (2008); and g) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug*

*Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention is intended to include all isotopes of atoms occurring in the present compounds. isotopes include those atoms having the same atomic number but different mass numbers. By way of general example and without limitation, isotopes of hydrogen include deuterium and tritium. isotopes of carbon include $^{13}C$ and $^{14}C$. isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form(s) having the same chemical structure/composition but different spatial arrangements of the molecules and/or ions forming the crystals. Compounds of the present invention can be provided as amorphous solids or crystalline solids. Lyophilization can be employed to provide the compounds of the present invention as a solid.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography and mass spectrometry, "HPLC" for high pressure liquid chromatography, "[M–H]" for parent mass minus a proton, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
$Ag_2CO_3$ silver carbonate
AgOAc silver acetate
AgOTf silver triflate
$CDCl_3$ deutero-chloroform
$CHCl_3$ chloroform
cDNA complimentary DNA
DMF dimethyl formamide
DMSO dimethyl sulfoxide
EDTA ethylenediaminetetraacetic acid
EtOAc ethyl acetate
$Et_2O$ diethyl ether
$AlCl_3$ aluminum chloride
Boc tert-butyloxycarbonyl
$CH_2Cl_2$ dichloromethane
$CH_3CN$ or ACN acetonitrile
$Cs_2CO_3$ cesium carbonate
HCl hydrochloric acid
$K_2CO_3$ potassium carbonate
KCN potassium cyanide
mCPBA or m-CPBA meta-chloroperbenzoic acid
Pd/C palladium on carbon
$PhSO_2Cl$ benzenesulfonyl chloride
i-$Pr_2NEt$ diisopropylethylamine
PS polystyrene
$SiO_2$ silica oxide/silica gel
$SnCl_2$ tin(II) chloride
TEA triethylamine
TFA trifluoroacetic acid
TFAA trifluoroacetic anhydride
THF tetrahydrofuran
$TMSCHN_2$ trimethylsilyldiazomethane
KOAc potassium acetate
$MgSO_4$ magnesium sulfate
MsCl methanesulfonyl chloride
MsOH or MSA methylsulfonic acid
NaCl sodium chloride
NaH sodium hydride
$NaHCO_3$ sodium bicarbonate
NaOH sodium hydroxide
$Na_2SO_3$ sodium sulfite
$Na_2SO_4$ sodium sulfate
$NH_3$ ammonia
$NH_4Cl$ ammonium chloride
$NH_4OH$ ammonium hydroxide The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and de-protection in the processes below may be carried out by procedures generally known in the art (see, for example, Wuts, P. G. M. et al., *Protecting Groups in Organic Synthesis*, Fourth Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*, Sixth Edition, Wiley & Sons, New York, N.Y. (2007); Katritzky, A. R. et al., eds., *Comprehensive Organic Functional Groups Transformations II*, Second Edition, Elsevier Science Inc., Tarrytown, N.Y. (2004); Larock, R. C., *Comprehensive Organic Transformations*, VCH Publishers, Inc., New York, N.Y. (1999), and references therein.

Scheme 1 describes the synthesis of cis-(3-arylcyclobutoxy)acetic acids 4. Reduction of 3-(4-haloaryl)cyclobutanone (e.g., with $NaBH_4$) gives the cis-3-(4-haloaryl)cyclobutanol 2 as the major isomer. Cyclobutanol 2 is then alkylated under basic conditions with an α-bromoacetate ester to provide the oxyacetic acid ester 3. Suzuki-Miyaura coupling (e.g., *Chem. Soc. Rev.*, 43:412 (2014)) of the 4-haloaryl oxyacetic acid ester 3 with an appropriately substituted aryl boronic acid followed by ester deprotection provides the desired cis-(3-aryl-cyclobutoxy)acetic acids 4.

Alternatively, the 4-haloaryl oxyacetic acid ester 3 undergoes palladium-mediated borylation with a bis-boronate (e.g., *J. Org. Chem.*, 60:7508 (1995)) to give the boronate ester 5. Suzuki-Miyaura coupling of 5 with an appropriately substituted aryl halide, followed by ester deprotection also provides the desired cis-(3-aryl-cyclobutoxy) acetic acids 4.

Scheme 1

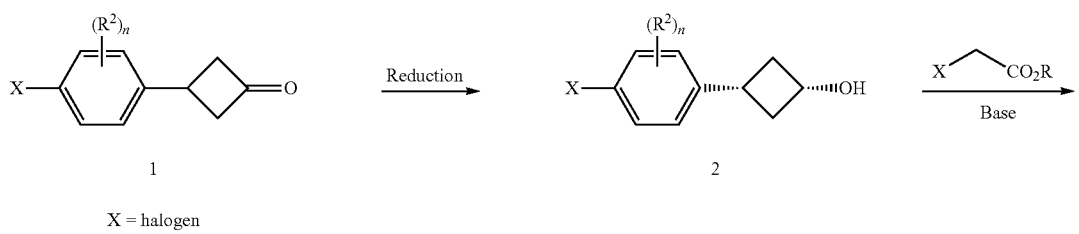

X = halogen

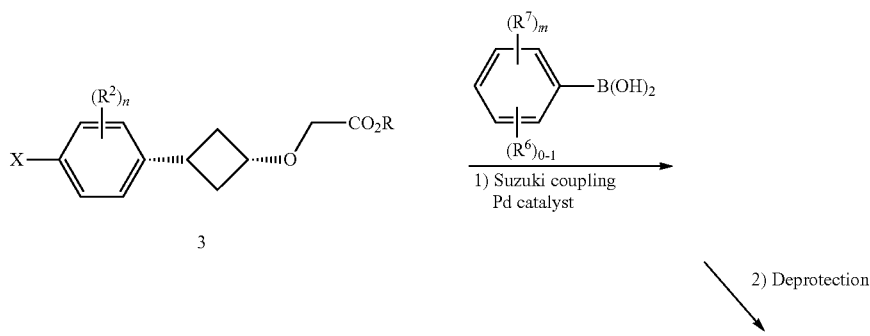

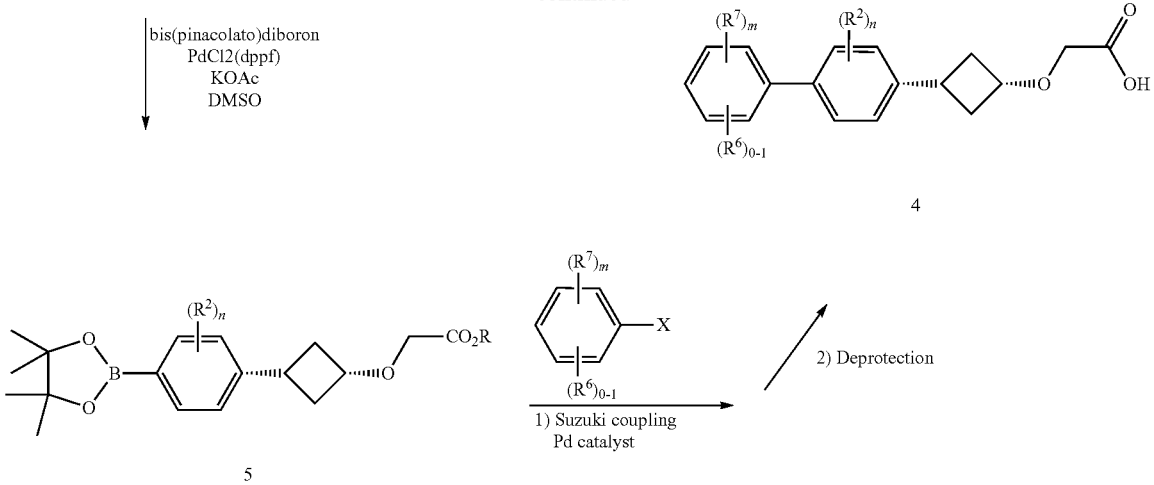

Scheme 2 describes an alternative synthetic route to 3'-oxy[1,1']biaryl cyclobutoxyacetic acids 8 and 9. Suzuki-Miyaura coupling (e.g., *Chem. Soc. Rev.*, 43:412 (2014)) of the 4-haloaryl oxyacetic acid ester 3 with a protected 3-hydroxy arylboronic acid 6 (the protecting group is, e.g., a t-butyl dimethyl silyl ether) followed by deprotection (e.g., $Bu_4NF$) provides the 3'-hydroxy[1,1']biaryl cyclobutoxyacetic acid ester 7. Phenol-cyclobutoxyacetic acid ester 7 is subjected to a Chan-Lam cross-coupling reaction (e.g., *Synthesis*, 829 (2011)) with an appropriately substituted aryl/heteroaryl boronic acid followed by ester deprotection to give the desired 3'-aryl oxy[1,1']biaryl cyclobutoxyacetic acids 8. Alternatively, phenol-cyclobutoxyacetic acid ester 7 is reacted either an appropriate alcohol ($R^7$—OH) under Mitsunobu conditions (*Chem. Rev.*, 109:2551 (2009)) or with an alkyl halide ($R^7$—X) under basic conditions followed by ester deprotection to give the desired 3'-alkoxy [1,1']biaryl cyclobutoxyacetic acids 9.

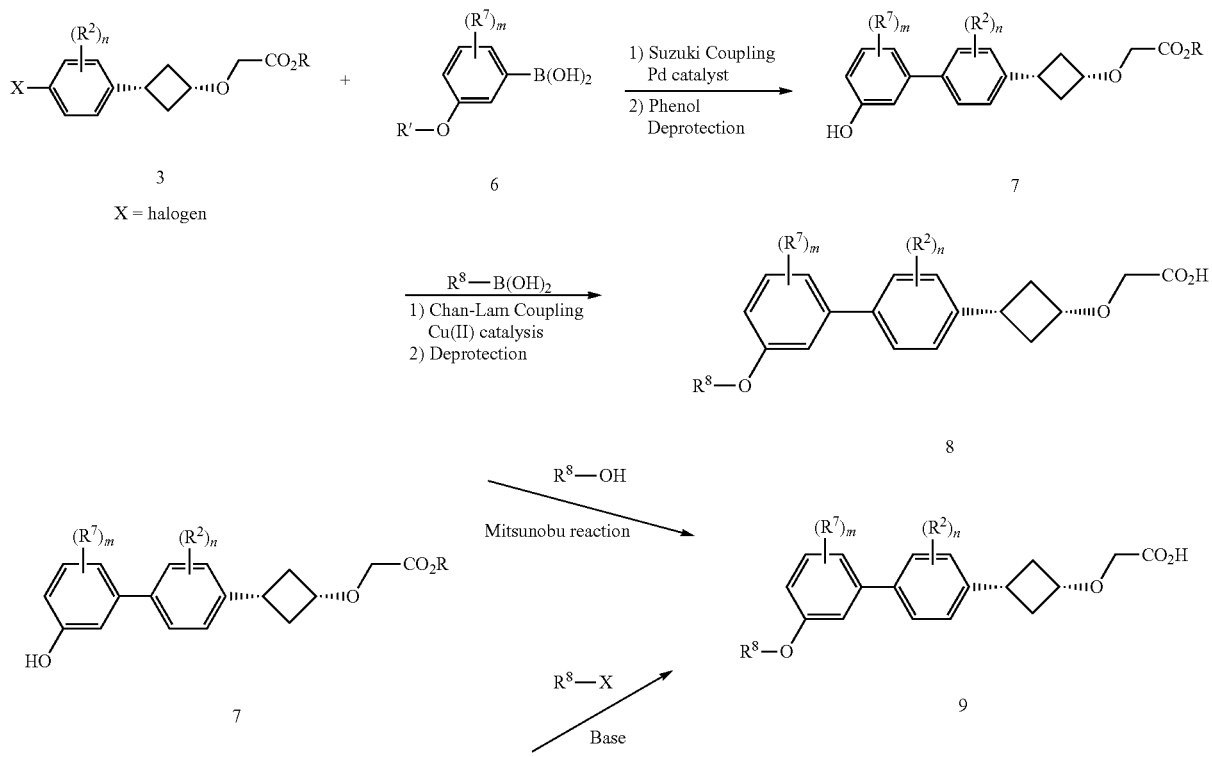

Scheme 3 describes the synthesis of 2-cyclobutylcyclopropanecarboxylic acids 12. Reaction of 3-(4-haloaryl)cyclobutanone with the anion of diethyl (isocyanomethyl)

phosphonate followed by acid-mediated hydrolysis provides the cyclobutyl aldehyde 10. Aldehyde 10 undergoes Horner-Emmons reaction followed by palladium-mediated cyclopropanation (*Tetrahedron Lett.*, 1465-1466 (1972)) to give the α,β-cyclopropyl ester 11. Suzuki-Miyaura coupling of the 4-haloaryl ester 11 with an appropriately substituted boronic acid followed by deprotection provides the desired 2-cyclobutylcyclopropanecarboxylic acids 12.

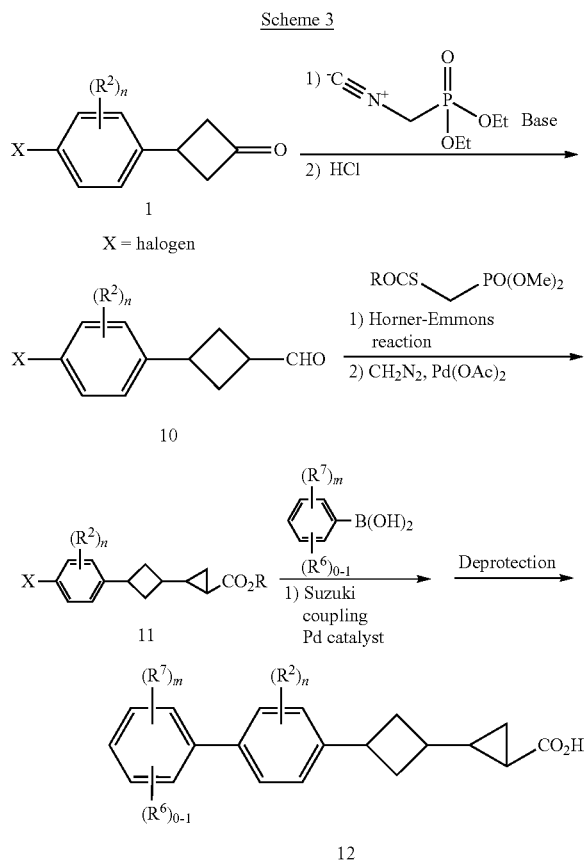

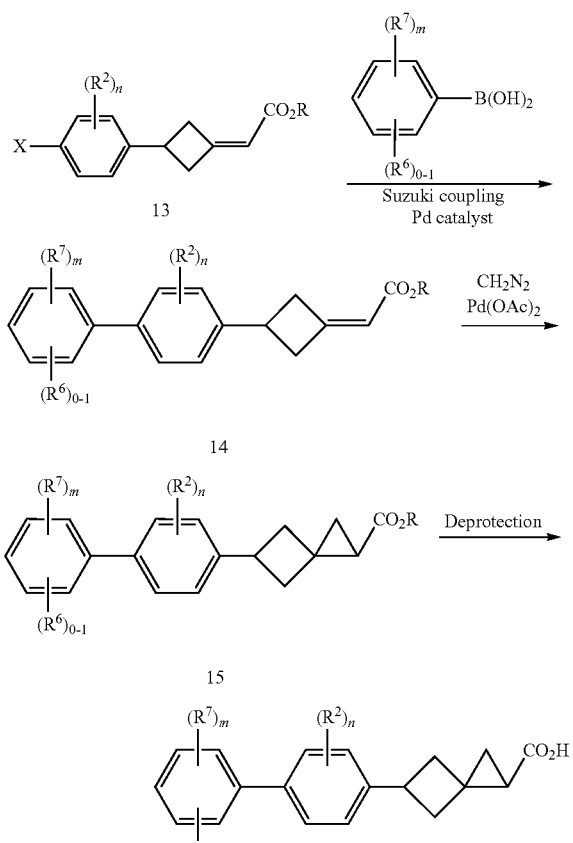

Scheme 4 shows the synthesis of spiro[2.3]hexane-1-carboxylic acids 16. Horner-Wadsworth-Emmons reaction of 3-(4-haloaryl)cyclobutanone 1 provides the α,β-unsaturated ester 13. Suzuki-Miyaura coupling of 4-haloaryl ester 13 with an appropriate aryl boronic acid gives the biaryl α,β-unsaturated ester 14. Palladium-mediated cyclopropanation of 14 (*Tetrahedron Lett.*, 1465-1466 (1972)) gives the α,β-cyclopropyl ester 15. Subsequent deprotection of ester 15 affords spiro[2.3]hexane-1-carboxylic acids 16.

Scheme 5 shows the synthesis of 2-cyclobutylcyclopropanecarboxylic acids 24. The 3-oxocyclobutanecarboxylic acid ester 17 is reacted with an appropriately substituted aryl lithium reagent 18 to give the cyclobutanol ester 19. Reductive ionic hydrogenolysis (e.g., Et$_3$SiH/TFA) of the tertiary alcohol 19 provides the cyclobutyl ester 20, which is then converted to aldehyde 21 in 2 steps (reduction to alcohol with e.g., LiAlH$_4$ or LiBH$_4$, then oxidation with e.g., Dess-Martin periodinane or Swern oxidation to the aldehyde). Cyclobutane aldehyde 21 undergoes a Horner-Emmons reaction with an appropriate phosphono-acetate ester in the presence of base to give the α,β-unsaturated ester 22. Hydrogenation of α,β-unsaturated ester followed by ester reduction provides the cyclobutanepropanol 23, which is alkylated under basic conditions with an α-bromo-acetate ester followed by deprotection to give the desired 2-cyclobutylcyclopropane carboxylic acids 24.

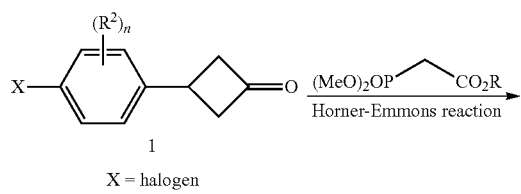

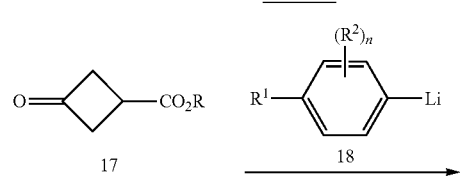

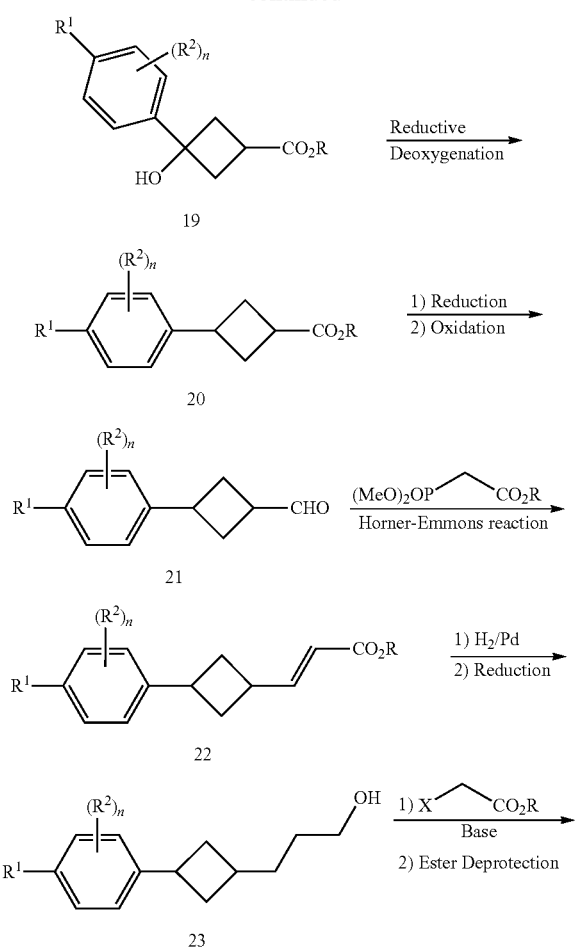

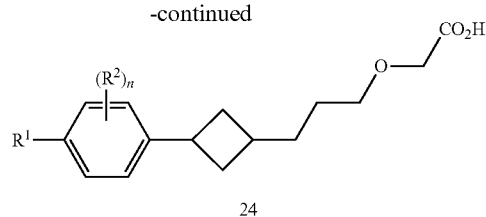

Scheme 6 describes the synthesis of cyclobutane oxyacetic acids 28 and cyclobutane oxypropanoic acids 29. The 3-aryl cyclobutane acid ester 20 is deprotonated (e.g., lithium diisopropyl amide), then reacted with an appropriate alkyl halide to afford the α-alkyl cyclobutane ester 24. Reduction of the ester to the alcohol followed by oxidation (as in Scheme 5) provided the cyclobutane aldehyde 25. Horner-Emmons reaction of aldehyde 25 gave the α,β-unsaturated ester 26, which was hydrogenated and reduced to the cyclobutane propanol 27 (as for Scheme 5). Cyclobutane alcohol 27 is reacted with an α-haloacetate ester in the presence of base, followed by ester deprotection to provide the desired cyclobutane oxyacetic acids 28. Alternatively, cyclobutane alcohol 27 undergoes an Michael addition with an acrylate ester in the presence of base, followed by ester deprotection to provide the desired cyclobutane oxypropanoic acids 29.

Scheme 6

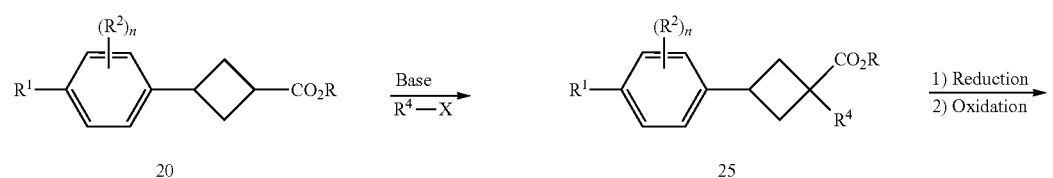

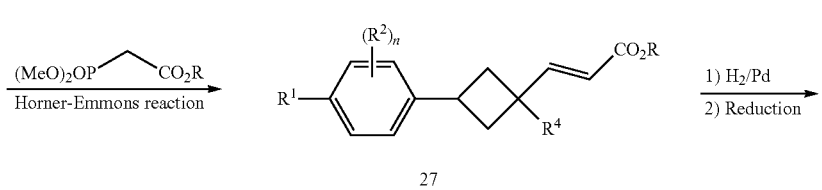

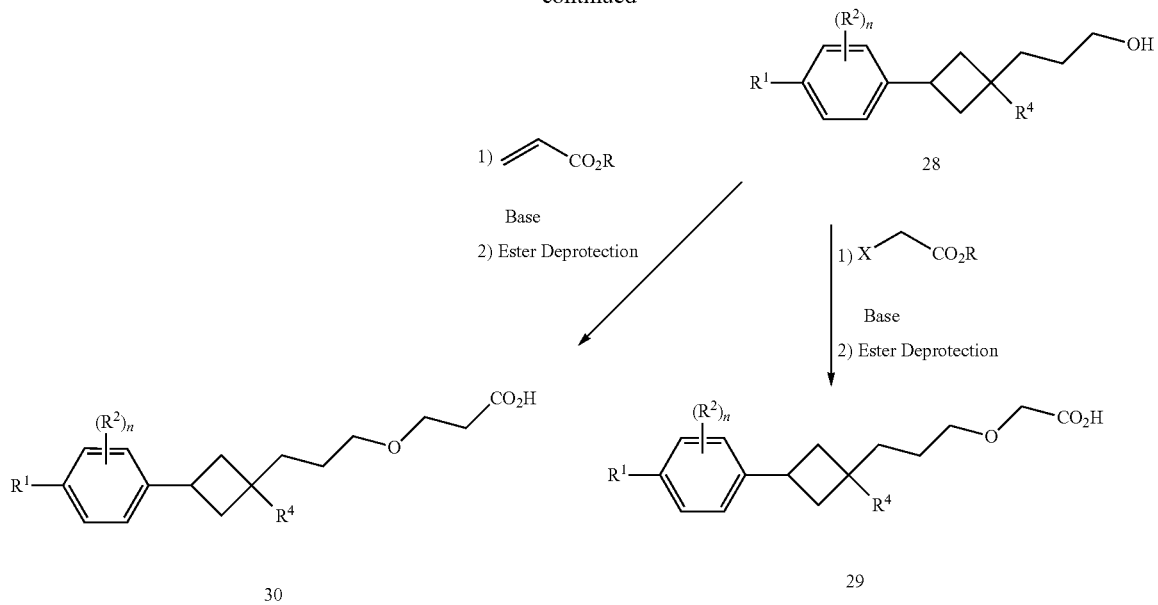

IV. Biology

Diabetes mellitus is a serious disease afflicting over 100 million people worldwide. It is diagnosed as a group of disorders characterized by abnormal glucose homeostasis resulting in elevated blood glucose. Diabetes is a syndrome with interrelated metabolic, vascular, and neuropathic components. The metabolic abnormality is generally characterized by hyperglycemia and alterations in carbohydrate, fat and protein metabolism caused by absent or reduced insulin secretion and/or ineffective insulin secretion. The vascular syndrome consists of abnormalities in the blood vessels leading to cardiovascular, retinal and renal complications. Abnormalities in the peripheral and autonomic nervous systems are also part of diabetic syndrome. Strikingly, diabetes is the fourth leading cause of global death by disease, the largest cause of kidney failure in developed countries, the leading cause of vision loss in industrialized countries and has the greatest prevalence increase in developing countries.

Type 2 diabetes, which accounts for 90% of diabetes cases, is characterized by increasing insulin resistance associated with inadequate insulin secretion after a period of compensatory hyperinsulinemia. The reasons for β cell secondary failure are not completely understood. Acquired pancreatic islet damage or exhaustion and/or genetic factors causing susceptibility to islet secretory insufficiency have been hypothesized.

Recently, five GPCRs (FFAR1 (GPR40), FFAR2 (GPR43), FFAR3 (GPR41), GPR84, and GPR120) were reported to recognize free fatty acids FFAR1, recognizes medium-long chainfatty acids like palmitic acid and linoleic acid FFAR2 and FFAR3 recognize short-chain fatty acids like acetate and butyrate whereas GPR84 recognizes medium-chain fatty acid like lauric acid. GPR120 recognizes long-chain fatty acids, especially EPA and DHA (Im, *Progress in Lipid Research,* 51:232-237(2012)). GPR120 has been detected in macrophages, dendritic cells, adipocytes, clara cells in bronchiole epithelium, and enteroendocrine L cells in colon (Miyauchi et al., *Naunyn-Schmiede-bergs Arch Pharmacol.,* 379:427-434 (2009)). The anti-inflammatory mechanism of omega-3 fatty acids using GPR120 knock-out mice was investigated (Oh et al., *Cell,* 142:687-698 (2010)). They suggested GPR120 activation by DHA interacts with TAB1 via b-arrestin-2, and that this interaction interrupts TAK1 activation by LPS or TNF-alpha, suppressing inflammatory responses via NF-δB and JNK in macrophages and dendritic cells (Oh et al., *Cell,* 142:687-698 (2010)). Furthermore, GPR120 activation was shown to enhance insulin-induced glucose uptake in adipose tissues through Gq/11 proteins and PI 3-kinase.

Similarly, GPR120-deficient mice fed a high-fat diet develop obesity, glucose intolerance and fatty liver with decreased adipocyte differentiation and lipogenesis and enhanced hepatic lipogenesis (Ichimura et al., *Nature,* 483 (7389):350-354 (2012). Insulin resistance in such mice was shown to be associated with reduced insulin signalling and enhanced inflammation in adipose tissue. In humans, GPR120 expression in adipose tissue was shown to be significantly higher in obese individuals than in lean controls. GPR120 gene sequencing in obese subjects revealed a deleterious non-synonymous mutation (p.R270H) that inhibits GPR120 signalling activity. Furthermore, the p.R270H variant was associated with increased risk of obesity in European populations.

Given the increase in the worldwide patient population afflicted by type 2 diabetes, there is a need for novel therapies which are effective with minimal adverse events. To decrease medical burden of type 2 diabetes through enhanced glycemic control, GPR120 modulator compounds of the present invention are being investigated here for their ability to increase glucose tolerance as well as the potential combination with a broad range of anti-diabetic drugs.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a GPR120 modulator. Exemplary subjects include human beings of any age with risk factors for metabolic disease. Common risk factors include, but are not limited to, age, sex, weight, family history, or signs of insulin resistance such as acanthosis nigricans, hypertension, dislipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; (b) relieving the disease-state, i.e., causing regression of the disease state; and/or (c) preventing the disease-state from occurring in a mammal, in particular, when such mammal is predisposed to the disease-state but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state. As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate GPR120 and/or to prevent or treat the disorders listed herein. When applied to a combination, the term refers to combined amounts of the active ingredients that result in the preventive or therapeutic effect, whether administered in combination, serially, or simultaneously.

GPR120 activity was monitored by measuring phosphorylation of ERK (pERK), since G protein receptors are known to activate the ERK signaling cascade either directly and/or through recruitment of arrestin that serves as a scaffold for downstream signaling events. Molecules that activated GPR120 with sufficient potency and efficacy in the pERK assay that also possessed desirable pharmacokinetic properties were evaluated in mice for glucose lowering by monitoring disposition of an oral glucose load by an oral glucose tolerance test (oGTT).

GPR120 pERK AlphaScreen SureFire Assay

The human and mouse GPR120-mediated intracellular phosphorylated ERK assays were established using CHOA12 cells stably transfected with the short form of human or mouse GPR120 receptor. Cells were cultured in growth medium consisting of F-12 media (Invitrogen Cat. #11765) with 5% Charcoal/Dextran FBS (Invitrogen Cat. #12676-029), 500 µg/mL GENETICIN® (Life Technologies Cat. #10131-027) and 250 µg/mL Zeocin (Invitrogen Cat. #R250-01). Cells were cryo preserved at a concentration of $2 \times 10^7$ cells/mL, in 90% Charcoal/Dextran FBS and 10% DMSO, and frozen in liquid nitrogen at a low passage number.

For the pERK assay, $2 \times 10^7$ cells/mL cryopreserved human and mouse cells were thawed rapidly in a 37° C. water bath and added to a T-225 flask containing 50 mL growth medium. The flasks were placed in a tissue culture incubator overnight (37° C., 5% $CO_2$). The next day, cells were harvested with trypsin (Gibco Cat. #25300-054), resuspended in serum-containing growth medium and counted using a Cellometer and volume adjusted to a concentration of $0.6 \times 10^6$ cells/mL. Cells were plated into 384-well clear bottom tissue culture plates (BD Cat. #353962) at 50 µL/well, for a density of 30,000 cells/well using a MULTIDROP® and incubated for 16-18 hours (overnight) at 37° C. with 5% $CO_2$. The next day, cells were serum starved in 30 µL of F-12 media without any serum or antibiotics for 2 hours at 37° C.

Test compounds were 3-fold, 11-point serially diluted in DMSO in a REMP assay plate (Matrix Cat. #4307) by Tecan and 5 µL was transferred into an ECHO source plate (Labcyte Cat. #LC-0200). Cells were then stimulated with 50 nL of compound dilutions using ECHO liquid handler for 7 minutes at 37° C. Compounds ranged from final assay concentrations of 33.33 µM to 0.56 nM.

The media was then dumped and cells lysed with 20 µL of 1× Lysis buffer from the AlphaScreen SureFire Phospho-ERK 1/2 Kit (Perkin Elmer Cat. #6760617M). The lysis buffer was diluted 5-fold with water before use. The plate was agitated on a shaker for 10 minutes after which 2 µL was transferred into a 384-well white proxiplate (Perkin Elmer Cat. #6008289). The SureFire assay reagent mix was prepared by mixing 60 parts Reaction Buffer, 10 parts Activation Buffer, 1 part Donor Beads, 1 part Acceptor Beads (Perkin Elmer Cat. #TGRES10K). 3.5 µL/well of this reagent mix was manually added to the proxiplate with a multichannel pipettor. Plates were spun down at 1000 rpm for 2 minutes, followed by light-protected incubation at room temperature for 2 hours. The plates were read on the Alpha-technology compatible Envision multilabel plate reader using AlphaScreen protocol according to manufacturer's specifications. The agonist effect of compounds was expressed as 100× (average sample−average blank)/(average total−average blank) where sample is the luminescence activity in the presence of test compound, blank is equal to the luminescence activity in the presence of DMSO control and the total is signal induced by 50 µM linolenic acid as reference compound. Activation data for the test compound over a range of concentrations was plotted as percentage activation of the test compound (100%=maximum response). After correcting for background, $EC_{50}$ values were determined. The $EC_{50}$ is defined as the concentration of test compound which produces 50% of the maximal response and was quantified using the 4 parameter logistic equation to fit the data.

The human and mouse GPR120-mediated intracellular phosphorylated ERK assays were also established using CHO-K1 cells stably transfected with the short form of human or mouse GPR120 receptor. Cells were cultured in growth medium consisting of F-12 media (Invitrogen Cat. #11765) with 5% Charcoal/Dextran FBS (Invitrogen Cat. #12676-029) and 500 µg/mL GENETICIN® (Life Technologies Cat. #10131-027). Cells were cryo preserved at a concentration of $3\times10^6$ cells/mL, in 70% F-12, 20% Charcoal/Dextran FBS and 10% DMSO, and frozen in liquid nitrogen at a low passage number.

For the pERK assay, $3\times10^6$ cells/mL cryopreserved human and mouse cells were thawed rapidly in a 37° C. water bath and added to a T-225 flask containing 50 mL growth medium. The flasks were placed in a tissue culture incubator overnight (37° C., 5% $CO_2$). The next day, cells were harvested with trypsin (Gibco Cat. #25300-054), resuspended in serum-containing growth medium and counted using a Cellometer and volume adjusted to a concentration of $0.5\times10^6$ cells/mL. Cells were plated into 384-well clear bottom tissue culture plates (BD Cat. #353962) at 50 µL/well, for a density of 25,000 cells/well using a MULTIDROP® and incubated for 16-18 hours (overnight) at 37° C. with 5% $CO_2$. The next day, cells were washed once with 50 µL of PBS without $Ca^{++}/Mg^{++}$ (Gibco Cat. #14190-036) and serum starved in 25 µL of F-12 media without any serum or antibiotics for 2 hours at 37° C.

Test compounds were 3-fold, 11-point serially diluted in DMSO in a REMP assay plate (Matrix Cat. #4307) by Tecan and 5 µL was transferred into an ECHO source plate (Labcyte Cat. #LC-0200). Cells were then stimulated with 40 nL of compound dilutions using ECHO liquid handler for 7 minutes at 37° C. Compounds ranged from final assay concentrations of 32 µM to 0.54 nM.

The media was then dumped and cells lysed with 20 µL of 1× Lysis buffer from the AlphaScreen SureFire Phospho-ERK 1/2 Kit (Perkin Elmer Cat. #6760617M). The lysis buffer was diluted 5-fold with water before use. The plate was agitated on a shaker for 10 minutes after which 2 µL was transferred into a 384-well white proxiplate (Perkin Elmer Cat. #6008289). The SureFire assay reagent mix was prepared by mixing 60 parts Reaction Buffer, 10 parts Activation Buffer, 1 part Donor Beads, 1 part Acceptor Beads (Perkin Elmer Cat. #TGRES10K). 3.5 µL/well of this reagent mix was manually added to the proxiplate with a multichannel pipettor. Plates were spun down at 1000 rpm for 2 minutes, followed by light-protected incubation at room temperature for 2 hours. The plates were read on the Alpha-technology compatible Envision multilabel plate reader using AlphaScreen protocol according to manufacturer's specifications. The agonist effect of compounds was expressed as 100× (average sample−average blank)/(average total−average blank) where sample is the luminescence activity in the presence of test compound, blank is equal to the luminescence activity in the presence of DMSO control and the total is signal induced by 50 µM linolenic acid as reference compound.

Activation data for the test compound over a range of concentrations was plotted as percentage activation of the test compound (100%=maximum response). After correcting for background, $EC_{50}$ values were determined. The $EC_{50}$ is defined as the concentration of test compound which produces 50% of the maximal response and was quantified using the 4 parameter logistic equation to fit the data.

The exemplified Examples disclosed below were tested in the GPR120 in vitro assays described above and were found having GPR120 agonist activity. Table 1 below lists the $EC_{50}$ values measured in the human GPR120 pERK assay for the following Examples.

| Example No. | $EC_{50}$ (µM) |
|---|---|
| 1 | 0.17 |
| 2 | 0.53 |
| 3 | 0.41 |
| 4 | 1.46 |
| 5 | 2.07 |
| 6 | 0.88 |
| 7 | 0.59 |
| 8 | 0.90 |
| 9 | 1.59 |
| 10 | 1.02 |
| 11 | 0.56 |
| 12 | 0.43 |
| 13 | 2.61 |
| 14 | 0.83 |
| 15 | 0.80 |
| 16 | 0.48 |
| 17 | 0.55 |
| 18 | 3.13 |
| 19 | 1.59 |
| 20 | 0.27 |
| 21 | 0.55 |
| 22 | 0.36 |
| 23 | 3.46 |
| 24 | 2.90 |
| 25 | 1.90 |
| 26 | 0.49 |
| 27 | 0.42 |
| 28 | 0.66 |
| 29 | 5.00 |
| 30 | 1.40 |
| 31 | 0.71 |
| 32 | 0.23 |
| 33 | 0.76 |
| 34 | 0.24 |
| 35 | 0.29 |
| 36 | 0.13 |
| 37 | 0.59 |
| 38 | 0.54 |
| 39 | 0.41 |
| 40 | 9.27 |
| 41 | 32.00 |
| 42 | 2.21 |
| 43 | 0.21 |
| 44 | 0.14 |
| 45 | 0.12 |
| 46 | 0.65 |
| 47 | 0.46 |
| 48 | 0.79 |
| 49 | 0.50 |
| 50 | 0.65 |
| 51 | 0.56 |
| 52 | 0.94 |
| 53 | 0.43 |
| 54 | 3.85 |
| 55 | 0.47 |
| 56 | 0.17 |
| 57 | 0.70 |
| 58 | 0.42 |
| 59 | 0.52 |
| 60 | 0.74 |
| 61 | 0.15 |
| 62 | 0.57 |
| 63 | 1.26 |
| 64 | 0.44 |
| 65 | 2.27 |
| 66 | 0.11 |
| 67 | 0.33 |
| 68 | 2.80 |

In Vivo GPR120 Assays

1) Acute Oral Glucose Tolerance Test

C57BL/6 mice were housed individually and fed a standard rodent chow diet. At approximately 11 weeks age, after a 5 h fast, these mice were orally treated with vehicle or test compounds 60 min before a glucose challenge (2 g/kg). Blood glucose levels were determined from tail bleeds taken at −60, 0, 15, 30, 60 and 120 min after the glucose challenge. The blood glucose excursion profile from t=0-120 min was used to calculate an area under the curve (AUC) for compound treatment. This AUC for compound treatment is compared to vehicle treatment. For instance, Example 1 (dosed at 30 mg/kg) reduced glucose AUC by 42% in this oral glucose tolerance test.

2) Acute Intraperitoneal Insulin Tolerance Test

C57BL/6 mice were housed individually and fed a standard rodent chow diet. At approximately 11 weeks age, after 5 h fast, these mice were orally treated with vehicle or test compounds 30 min before an insulin challenge (0.1 µ/kg). Blood glucose levels were determined from tail bleeds taken at −30, 0, 15, 30, 60, 90 and 120 min after insulin injection. The blood glucose excursion profile from t=0-120 min was used to calculate a negative area under the curve (AUC) for compound treatment. This AUC for compound treatment is compared to vehicle treatment.

The compounds of the present invention possess activity as modulators of GPR120, and, therefore, may be used in the treatment of diseases associated with GPR120 activity. Via modulation of GPR120, the compounds of the present invention may preferably be employed to modulate the production/secretion of insulin and/or gut hormones, such as GLP-1, GIP, PYY, CCK and amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, fatty liver disease, dyslipidemia, hyperlipidemia, hypertriglyceridemia, hypercholesterolemia, low HDL, high LDL, lipid disorders, lipodystrophy, liver diseases such as NASH (Non-Alcoholic SteatoHepatitis), NAFLD (Non-Alcoholic Fatty Liver Disease) and liver cirrhosis, and treatment of side-effects related to diabetes.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR120 modulators or one or more other suitable therapeutic agents useful in the treatment of the aforementioned disorders including: antidiabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatitis agents, lipid lowering agents, anorectic agents, appetite suppressants, treatments for heart failure, treatments for peripheral arterial disease and anti-inflammatory agents.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR120 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the compound of the present invention include, but are not limited to, insulin secretagogues or insulin sensitizers, other GPR120 receptor modulators, or other antidiabetic agents. These agents include, but are not limited to, dipeptidyl peptidase IV (DP4) inhibitors (for example, sitagliptin, saxagliptin, linagliptin. alogliptin, vildagliptin), biguanides (for example, metformin, phenformin), sulfonyl ureas (for example, gliburide, glimepiride, glipizide), glucosidase inhibitors (for example, acarbose, miglitol), PPARγ agonists such as thiazolidinediones (for example, rosiglitazone, pioglitazone), PPAR α/γ dual agonists (for example, muraglitazar, peliglitazar, tesaglitazar, aleglitazar), glucokinase activators (e.g., PF-04937319 and AMG-151, as well as other compounds described in Fyfe, M. C. T. et al., *Drugs of the Future*, 34(8):641-653 (2009) and incorporated herein by reference), GPR40 receptor modulators (e.g., TAK-875), GPR119 receptor modulators (e.g., MBX-2952, PSN821, APD597), other GPR120 receptor modulators (e.g., compound 43 from *J. Med. Chem.*, 55:4511-4515 (2012)), sodium-glucose transporter-2 (SGLT2) inhibitors (for example dapagliflozin, canagliflozin, remagliflozin), 11β-HSD-1 inhibitors (for example MK-0736, BI35585, BMS-823778, and LY2523199), amylin analogs such as pramlintide, and/or insulin. Reviews of current and emerging therapies for the treatment of diabetes can be found in: Mohler, M. L. et al., *Medicinal Research Reviews,* 29(1): 125-195 (2009), and Mizuno, C. S. et al., *Current Medicinal Chemistry,* 15:61-74 (2008).

The GPR120 receptor modulator of the present invention may also be optionally employed in combination with agents for treating complication of diabetes. These agents include PKC inhibitors and/or AGE inhibitors.

The GPR120 receptor modulator of the present invention way also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, MGAT2 (monoacylglycerol transferase 2) inhibitors (for example, compounds from WO 2012/124744, or compound (S)-10 from *Bioorg. Med. Chem. Lett*. (2013), doi: http://dx.doi.org/10.1016/j.bmcl.2013.02.084) and the like. The compound of structure I may also be employed in combination with an agonist of the glucagon-like peptide-1 receptor (GLP-1 R), such as exenatide, liraglutide, GLP-1(1-36) amide, GLP-1 (7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., *Nature Reviews Drug Discovery,* 5:369-370 (2006); Jones, D., *Nature Reviews: Drug Discovery,* 8:833-834 (2009); Obici, S., *Endocrinology,* 150(6):2512-2517 (2009); and Elangbam, C. S., *Vet. Pathol.,* 46(1):10-24 (2009).

The above other therapeutic agents, when employed in combination with the compounds of the present invention may be used, for example, in those amounts indicated in the Physicians' Desk Reference, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the GPR120 receptor. Such compounds may be provided in a commercial kit, for example, for use in pharmaceutical research involving GPR120 or anti-diabetic activity. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving GPR120.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of multiple diseases or disorders associated with GPR120 (as defined previously). In another embodiment, the package insert states that the pharmaceutical composition can be used in combination (as defined previously) with a second therapeutic agent for the treatment of multiple diseases or disorders associated with GPR120. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

NMR Employed in Characterization of Examples

NMR (nuclear magnetic resonance) spectra were typically obtained on Bruker or JEOL® 400 MHz and 500 MHz instruments in the indicated solvents. All chemical shifts are reported in ppm from tetramethylsilane with the solvent resonance as the internal standard. $^1$H NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

Spectral data are reported as chemical shift (multiplicity, number of hydrogens, coupling constants in Hz) and are reported in ppm (δ units) relative to either an internal standard (tetramethylsilane=0 ppm) for $^1$H NMR spectra, or are referenced to the residual solvent peak (2.49 ppm for CD$_3$SOCD$_2$H, 3.30 ppm for CD$_2$HOD, 1.94 for CHD$_2$CN, 7.26 ppm for CHCl$_3$, 5.32 ppm for CDHCl$_2$).

HPLC/MS and Preparatory/Analytical HPLC Methods Employed in Characterization or Purification of Examples The term HPLC refers to a Shimadzu high performance liquid chromatography with one of following methods:

HPLC-1: SunFire C18 (4.6×150 mm) 3.5 μm, gradient from 10 to 100% B:A for 12 min, then 3 min hold at 100% B;

Mobile Phase A: 0.05% TFA in H$_2$O:CH$_3$CN (95:5);

Mobile Phase B: 0.05% TFA in CH$_3$CN:H$_2$O (95:5);

TFA Buffer pH=2.5; Flow rate: 1 mL/min; Detector wavelength: 254 nm, 220 nm.

HPLC-2: XBridge Phenyl (4.6×150 mm) 3.5 μm, gradient from 10 to 100% B:A for 12 min, then 3 min hold at 100% B;

Mobile Phase A: 0.05% TFA in H$_2$O:CH$_3$CN (95:5);

Mobile Phase B: 0.05% TFA in CH$_3$CN:H$_2$O (95:5);

TFA Buffer pH=2.5; Flow rate: 1 mL/min; Detector wavelength: 254 nm, 220 nm.

HPLC-3: CHIRALPAK® AD-H, 4.6×250 mm, 5 μm;

Mobile Phase: 30% EtOH-heptane (1:1)/70% CO$_2$;

Flow rate=40 mL/min, 100 Bar, 35° C.; Detector wavelength: 220 nm.

HPLC-4: Waters Acquity UPLC BEH C18, 2.1×50 mm, 1.7 μm particles;

Mobile Phase A: 5:95 MeCN:H$_2$O with 10 mM NH$_4$OAc;

Mobile Phase B: 95:5 CH$_3$CN:H$_2$O with 10 mM NH$_4$OAc;

Temperature: 50° C.; Gradient: 0-100% B over 3 min, then a 0.75-min hold at 100% B;

Flow: 1.11 mL/min; Detection: UV at 220 nm.

HPLC-5: Waters Acquity UPLC BEH C18, 2.1×50 mm, 1.7-μm particles;

Mobile Phase A: 5:95 MeCN:H$_2$O with 0.1% TFA;

Mobile Phase B: 95:5 CH$_3$CN:H$_2$O with 0.1% TFA;

Temperature: 50° C.; Gradient: 0-100% B over 3 min, then a 0.75-min hold at 100% B; Flow: 1.11 mL/min; Detection: UV at 220 nm.

Example 1

Cis-2-(-3-(2'-fluoro-5'-phenoxy-[1,1'-biphenyl]-4-yl)cyclobutoxy)acetic acid

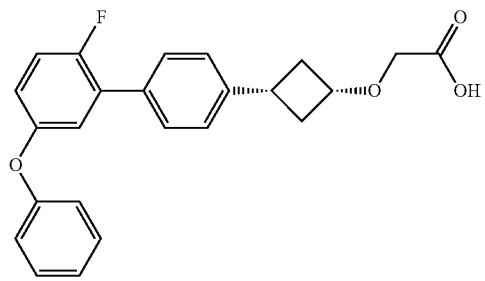 [SMILES: O=C(O)CO[C@H]1C[C@@H](c2ccc(-c3cc(Oc4ccccc4)ccc3F)cc2)C1]

1A. Cis-3-(4-bromophenyl)cyclobutanol

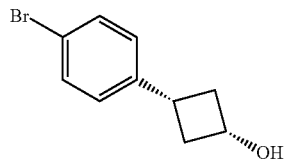 [SMILES: O[C@H]1C[C@@H](c2ccc(Br)cc2)C1]

To a 0° C. solution of 3-(4-bromophenyl)cyclobutanone (489 mg, 2.17 mmol) in MeOH (6 mL) was added NaBH$_4$ (107 mg, 2.82 mmol). The solution was allowed to warm to rt and stirred for 2 h at rt, after which sat'd aq. NaHCO$_3$ was added. The mixture was concentrated in vacuo and extracted with EtOAc. The combined organic extracts were dried (MgSO$_4$) and concentrated in vacuo. The residue was chromatographed (SiO$_2$; 40 g cartridge; EtOAc/Hexanes=3/7) to give the title compound (389 mg, 1.71 mmol, 79% yield) as a clear oil. LCMS, [M+H]$^+$=226.9. $^1$H NMR (500 MHz, CDCl$_3$) δ 7.45-7.40 (m, 2H), 7.13-7.07 (m, 2H), 4.34-4.24 (m, 1H), 2.92 (tt, J=10.1, 7.5 Hz, 1H), 2.82-2.73 (m, 2H), 2.03-1.94 (m, 2H), 1.77 (d, J=6.1 Hz, 1H).

1B. Cis-tert-butyl 2-(3-(4-bromophenyl)cyclobutoxy)acetate

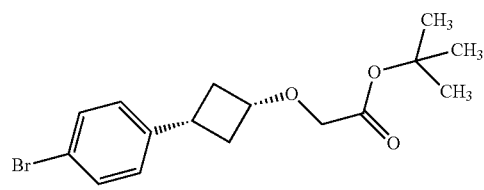 [SMILES: CC(C)(C)OC(=O)CO[C@H]1C[C@@H](c2ccc(Br)cc2)C1]

To a 0° C. solution of cis-3-(4-bromophenyl)cyclobutanol (490 mg, 2.16 mmol) in toluene (15 mL) was added 35% aq. NaOH (5 mL), followed by Bu$_4$NHSO$_4$ (44 mg, 0.13 mmol). The reaction mixture was stirred at 0° C. for 30 min, then tert-butyl 2-bromoacetate (0.64 mL, 4.32 mmol) was added and the reaction mixture was stirred for 14 h at rt. The reaction was acidified with conc HCl and extracted with EtOAc (3×). The combined organic extracts were washed with brine (5 mL), dried (MgSO$_4$) and concentrated in vacuo. The residue was chromatographed (SiO₂; 40 g; continuous gradient from 0 to 20% Solvent B over 25 min, hold at 20% Solvent B for 10 min, where Solvent A=Hexanes and Solvent B=10% EtOAc) to give the title compound (672 mg, 1.97 mmol, 91% yield) as a colorless oil. ¹H NMR showed that the product contained ~7% of the trans-isomer. LCMS, [M+H]⁺=341.0. ¹H NMR (500 MHz, CDCl₃) δ 7.45-7.39 (m, 2H), 7.11 (m, 2H), 4.09-4.00 (m, 1H), 3.93 (s, 2H), 2.99-2.88 (m, 1H), 2.76-2.66 (m, 2H), 2.14-2.02 (m, 2H), 1.49 (s, 9H).

1C. Cis-tert-butyl 2-(3-(2'-fluoro-5'-phenoxy-[1,1'-biphenyl]-4-yl)cyclobutoxy)acetate

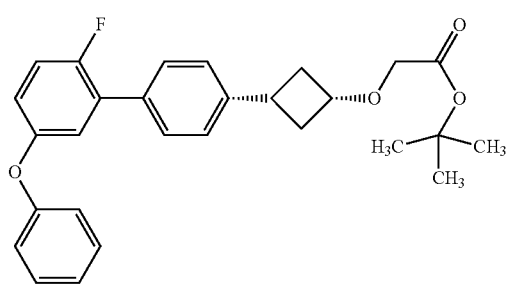

A mixture of cis-tert-butyl 2-(3-(4-bromophenyl)cyclobutoxy)acetate (40 mg, 0.12 mmol), (2-fluoro-5-phenoxyphenyl)boronic acid (41 mg, 0.18 mmol), (Ph₃P)₄Pd (14 mg, 0.012 mmol) and K₂CO₃ (49 mg, 0.35 mmol) in THF (2 mL) and water (0.7 mL) was heated in a microwave reactor at 130° C. for 20 min under Ar. The reaction was then cooled to rt and acidified with 1N aq. HCl to pH=~2-3, and extracted with EtOAc (4×10 mL). The combined organic extracts were dried (MgSO₄) and concentrated in vacuo to afford the crude product which was used in the next step without further purification. LCMS, [M+Na]⁺=471.1.

Example 1

A mixture of LiOH.H₂O (25 mg, 0.59 mmol) and cis-tert-butyl 2-(3-(2'-fluoro-5'-phenoxy-[1,1'-biphenyl]-4-yl)cyclobutoxy)acetate (66 mg, 0.15 mmol) in THF (1 mL) and water (0.5 mL) was stirred at rt overnight, then was partitioned between EtOAc (10 mL) and H₂O (10 mL). The aqueous layer was washed with EtOAc (2×5 mL). The combined organic washes were extracted with H₂O (3×5 mL). The combined aqueous extracts were acidified with 1N aq. HCl to pH ~3 and extracted with EtOAc (3×20 mL). The combined organic extracts were washed with brine (5 mL), dried (MgSO₄) and concentrated in vacuo. The crude product was purified by preparative LC/MS using the following conditions: Column: Waters XBridge C18, 19×200 mm, 5-μm particles; Guard Column: Waters XBridge C18, 19×10 mm, 5-μm particles; Mobile Phase A: 5:95 MeCN:H₂O with 0.1% TFA; Mobile Phase B: 95:5 MeCN:H₂O with 0.1% TFA; Gradient: 50-90% B over 20 min, then a 5-min hold at 100% B; Flow: 20 mL/min. Fractions containing the desired product were combined and dried via centrifugal evaporation to give the title compound (18 mg, 0.05 mmol, 32% yield). LCMS, [M–H]⁺=391.1. ¹H NMR (500 MHz, DMSO-d₆) δ 7.49-7.45 (m, 2H), 7.42-7.29 (m, 5H), 7.17-7.11 (m, 2H), 7.07-6.99 (m, 3H), 4.05 (quin, J=7.3 Hz, 1H), 3.89 (s, 2H), 3.05-2.95 (m, 1H), 2.68-2.59 (m, 2H), 1.99-1.88 (m, 2H). HPLC-4: RT=1.68 min; HPLC-5: RT=2.22 min; purity=100%.

Examples from Table 1 were prepared using the general synthetic sequence described for the preparation of Example 1.

TABLE 1

| Ex. No. | Structure (Ar—) and Name | Analytical Data |
|---|---|---|
| 2 | Cis-2-(3-(2'-fluoro-5'-isopropoxy-[1,1'-biphenyl]-4-yl)cyclobutoxy)acetic acid | LCMS, [M – H]⁺ = 357.2. ¹H NMR (500 MHz, CDCl₃) δ 7.50 (dd, J = 8.0, 1.4 Hz, 2H), 7.33 (d, J = 8.3 Hz, 2H), 7.08-7.01 (m, 1H), 6.95 (dd, J = 6.5, 3.2 Hz, 1H), 6.81 (dt, J = 8.8, 3.4 Hz, 1H), 4.56-4.46 (m, 1H), 3.68 (quin, J = 8.3 Hz, 1H), 2.84-2.74 (m, 1H), 2.70 (d, J = 7.7 Hz, 2H), 2.50-2.41 (m, 2H), 2.25 (ddd, J = 12.8, 8.8, 4.3 Hz, 2H), 1.35 (d, J = 6.1 Hz, 6H). HPLC-4: RT = 1.56 min; HPLC-5: RT = 2.06 min; purity = 100%. |
| 3 | Cis-2-(3-(5'-(cyclopentyloxy)-2'-fluoro-[1,1'-biphenyl]-4-yl)cyclobutoxy)acetic acid | LCMS, [M – H]⁺ = 383.2. ¹H NMR (500 MHz, DMSO-d₆) δ 7.44 (d, J = 7.3 Hz, 2H), 7.30 (d, J = 7.9 Hz, 2H), 7.15 (t, J = 9.6 Hz, 1H), 6.91-6.82 (m, 2H), 4.82-4.75 (m, 1H), 4.06-3.97 (m, 1H), 3.92 (s, 2H), 3.04-2.93 (m, 1H), 2.62 (d, J = 7.3 Hz, 2H), 1.97-1.80 (m, 4H), 1.72-1.47 (m, 6H). HPLC-4: RT = 1.74 min; HPLC-5: RT = 2.30 min; purity = 100%. |
| 4 | Cis-2-(3-(2'-phenoxy-[1,1'-biphenyl]-4-yl)cyclobutoxy)acetic acid | LCMS, [M – H]⁺ = 385.0. ¹H NMR (500 MHz, DMSO-d₆) δ 7.50-7.43 (m, 3H), 7.39-7.21 (m, 6H), 7.05 (t, J = 7.4 Hz, 1H), 6.98 (d, J = 8.0 Hz, 1H), 6.90 (d, J = 8.0 Hz, 2H), 4.08-3.98 (m, 1H), 3.89 (s, 2H), 3.00-2.91 (m, 1H), 2.65-2.56 (m, 2H), 1.97-1.87 (m, 2H). HPLC-4: RT = 1.65 min; HPLC-5: RT = 2.16 min; purity = 96%. |
| 5 | Cis-2-(3-(4-(5-fluoro-2-isopropoxypyridin-4-yl)phenyl)cyclobutoxy)acetic acid | LCMS, [M – H]⁺ = 411.1. ¹H NMR (500 MHz, DMSO-d₆) δ 8.19 (d, J = 2.5 Hz, 1H), 7.61-7.55 (m, 2H), 7.37 (d, J = 8.0 Hz, 2H), 6.88 (d, J = 5.5 Hz, 1H), 5.20 (quin, J = 6.2 Hz, 1H), 4.10-4.00 (m, 1H), 3.92 (s, 2H), 3.09-2.97 (m, 1H), 2.69-2.59 (m, 2H), 2.01-1.91 (m, 2H), 1.30 (d, J = 6.1 Hz, 6H). HPLC-4: RT = 1.46 min; HPLC-5: RT = 1.89 min; purity = 99%. |

TABLE 1-continued

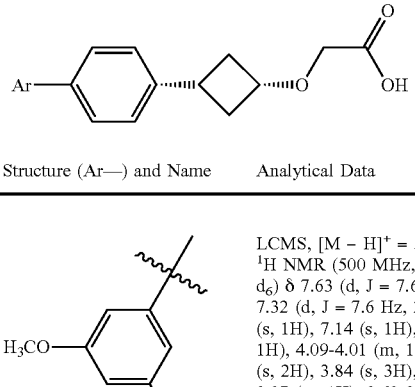

| Ex. No. | Structure (Ar—) and Name | Analytical Data |
|---|---|---|
| 6 | 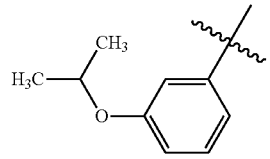 [SMILES: *c1cccc(OC(C)C)c1]<br>Cis-2-(3-(3'-chloro-5'-methoxy-[1,1'-biphenyl]-4-yl)cyclobutoxy)acetic acid | LCMS, [M − H]+ = 345.1.<br>1H NMR (500 MHz, DMSO-d6) δ 7.63 (d, J = 7.6 Hz, 2H), 7.32 (d, J = 7.6 Hz, 2H), 7.26 (s, 1H), 7.14 (s, 1H), 7.00 (s, 1H), 4.09-4.01 (m, 1H), 3.94 (s, 2H), 3.84 (s, 3H), 3.06-2.97 (m, 1H), 2.69-2.60 (m, 2H), 2.00-1.90 (m, 2H). HPLC-4: RT = 1.52 min; HPLC-5: RT = 2.07 min; purity = 100%. |
| 7 | 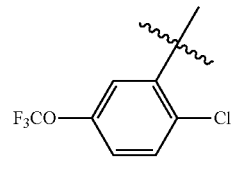 [SMILES: *c1cc(OC(F)(F)F)ccc1Cl]<br>Cis-2-(3-(3'-isopropoxy-[1,1'-biphenyl]-4-yl)cyclobutoxy)acetic acid | LCMS, [M − H]+ = 339.2.<br>1H NMR (500 MHz, DMSO-d6) δ 7.58 (d, J = 6.7 Hz, 2H), 7.36- 7.26 (m, 3H), 7.18-7.08 (m, 2H), 6.89 (d, J = 7.9 Hz, 1H), 4.74-4.65 (m, 1H), 3.93 (br. s., 2H), 3.42-3.35 (m, 1H), 3.03-2.96 (m, 1H), 2.70-2.58 (m, 2H), 2.01-1.91 (m, 2H), 1.28 (d, J = 6.1 Hz, 6H). HPLC-4: RT = 1.54 min; HPLC-5: RT = 2.08 min; purity = 100%. |
| 8 | 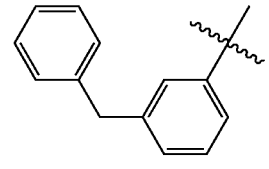 [SMILES: *c1cccc(Cc2ccccc2)c1]<br>Cis-2-(3-(2'-chloro-5'-(trifluoromethoxy)-[1,1'-biphenyl]-4-yl)cyclobutoxy)acetic acid | LCMS, [M − H]+ = 399.1.<br>1H NMR (500 MHz, DMSO-d6) δ 7.70 (d, J = 8.5 Hz, 1H), 7.45-7.29 (m, 6H), 4.16-3.82 (m, 3H), 3.11-2.96 (m, 1H), 2.71-2.59 (m, 2H), 2.09-1.88 (m, 2H). HPLC-4: RT = 1.68 min; HPLC-5: RT = 2.23 min; purity = 99%. |
| 9 | 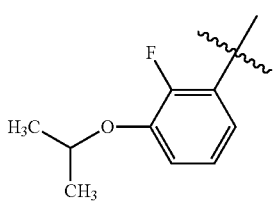<br>Cis-2-(3-(3'-benzyl-[1,1'-biphenyl]-4-yl)cyclobutoxy)acetic acid | LCMS, [M − H]+ = 371.2.<br>1H NMR (500 MHz, DMSO-d6) δ 7.58-7.48 (m, 3H), 7.44 (d, J = 7.6 Hz, 1H), 7.37-7.25 (m, 7H), 7.21-7.15 (m, J = 7.6 Hz, 2H), 4.06-4.01 (m, 1H), 3.92 (br. s., 2H), 3.03-2.93 (m, 1H), 2.68-2.59 (m, 2H), 1.99-1.90 (m, 2H). HPLC-4: RT = 1.74 min; HPLC-5: RT = 2.28 min; purity = 99%. |
| 10 | 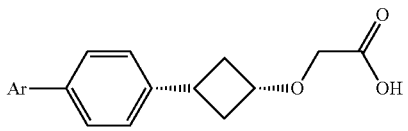<br>Cis-2-(3-(2'-fluoro-3'-isopropoxy-[1,1'-biphenyl]-4-yl)cyclobutoxy)acetic acid | LCMS, [M − H]+ = 357.2.<br>1H NMR (500 MHz, DMSO-d6) δ 7.45 (d, J = 7.6 Hz, 2H), 7.32 (d, J = 7.9 Hz, 2H), 7.19-7.11 (m, 2H), 7.03-6.96 (m, 1H), 4.64 (dt, J = 12.1, 5.9 Hz, 1H), 4.10-4.00 (m, 1H), 3.92 (s, 2H), 3.06-2.94 (m, 1H), 2.69-2.60 (m, 2H), 2.02-1.89 (m, 2H), 1.30 (d, J = 6.1 Hz, 6H). HPLC-4: RT = 1.53 min; HPLC-5: RT = 2.06 min; purity = 95%. |
| 11 | 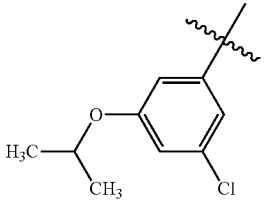 [SMILES: *c1cc(Cl)cc(OC(C)C)c1]<br>Cis-2-(3-(3'-chloro-5'-isopropoxy-[1,1'-biphenyl]-4-yl)cyclobutoxy) acetic acid | LCMS, [M − H]+ = 373.1.<br>1H NMR (500 MHz, DMSO-d6) δ 7.61 (d, J = 7.6 Hz, 2H), 7.31 (d, J = 7.6 Hz, 2H), 7.21 (s, 1H), 7.09 (s, 1H), 6.96 (s, 1H), 4.80-4.68 (m, 1H), 4.09-4.00 (m, 1H), 3.92 (s, 2H), 3.06-2.95 (m, 1H), 2.69-2.59 (m, 2H), 2.00-1.89 (m, 2H), 1.28 (d, J = 5.8 Hz, 6H). HPLC-4: RT = 1.74 min; HPLC-5: RT = 2.32 min; purity = 99%. |
| 12 | 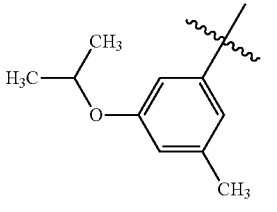 [SMILES: *c1cc(C)cc(OC(C)C)c1]<br>Cis-2-(3-(3'-isopropoxy-5'-methyl-[1,1'-biphenyl]-4-yl)cyclobutoxy) acetic acid | LCMS, [M − H]+ = 353.2.<br>1H NMR (500 MHz, DMSO-d6) δ 7.55 (d, J = 7.6 Hz, 2H), 7.28 (d, J = 7.6 Hz, 2H), 6.98 (s, 1H), 6.90 (s, 1H), 6.71 (s, 1H), 4.70-4.62 (m, 1H), 4.09-3.99 (m, 1H), 3.92 (s, 2H), 2.99 (m, 1H), 2.68-2.58 (m, 2H), 2.31 (s, 3H), 1.99-1.87 (m, 2H), 1.27 (d, J = 6.1 Hz, 6H). HPLC-4: RT = 1.64 min; HPLC-5: RT = 2.20 min; purity = 100%. |
| 13 | 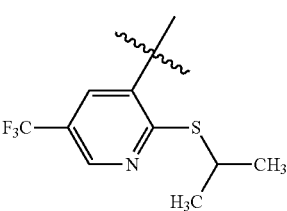 [SMILES: *c1cc(C(F)(F)F)cnc1SC(C)C]<br>Cis-2-(3-(4-(2-(isopropylthio)-5-(trifluoromethyl)pyridin-3-yl)phenyl)cyclobutoxy)acetic acid | LCMS, [M − H]+ = 424.1.<br>1H NMR (500 MHz, DMSO-d6) δ 8.82 (s, 1H), 7.80 (s, 1H), 7.41-7.31 (m, 4H), 4.09-3.97 (m, 2H), 3.95 (s, 2H), 3.08-2.98 (m, 1H), 2.70-2.61 (m, 2H), 2.03- 1.91 (m, 2H), 1.31 (d, J = 6.7 Hz, 6H). HPLC-4: RT = 1.83 min; HPLC-5: RT = 2.41 min; purity = 99%. |
| 14 | 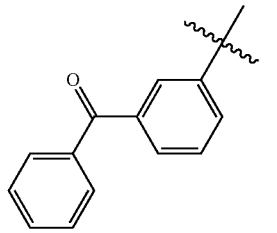 [SMILES: *c1cccc(C(=O)c2ccccc2)c1]<br>Cis-2-(3-(3'-benzoyl-[1,1'-biphenyl]-4-yl)cyclobutoxy) acetic acid | LCMS, [M − H]+ = 385.1.<br>1H NMR (500 MHz, DMSO-d6) δ 7.98-7.91 (m, 2H), 7.79 (d, J = 7.6 Hz, 2H), 7.72-7.55 (m, 7H), 7.34 (d, J = 7.9 Hz, 2H), 4.09-4.00 (m, 1H), 3.94 (s, 2H), 3.06-2.95 (m, 1H), 2.69-2.60 (m, 2H), 2.00-1.89 (m, 2H). HPLC-4: RT = 1.52 min; HPLC-5: RT = 2.03 min; purity = 100%. |

TABLE 1-continued

Ar—⟨phenyl⟩—⟨cyclobutyl⟩—O—CH₂—COOH

| Ex. No. | Structure (Ar—) and Name | Analytical Data |
|---|---|---|
| 15 | Cis-2-(3-(2',6'-difluoro-3'-isopropoxy-[1,1'-biphenyl]-4-yl)cyclobutoxy)acetic acid | LCMS, [M – H]⁺ = 375.1. ¹H NMR (500 MHz, DMSO-d₆) δ 7.39-7.32 (m, 4H), 7.23-7.16 (m, 1H), 7.12-7.06 (m, 1H), 4.63-4.54 (m, 1H), 4.10-4.01 (m, 1H), 3.91 (br. s., 2H), 3.06-2.97 (m, 1H), 2.69-2.60 (m, 2H), 2.03-1.92 (m, 2H), 1.28 (d, J = 5.8 Hz, 6H). HPLC-4: RT = 1.55 min; HPLC-5: RT = 2.05 min; purity = 94%. |
| 16 | Cis-2-(3-(2'-methoxy-5'-(trifluoromethoxy)-[1,1'-biphenyl]-4-yl)cyclobutoxy)acetic acid | LCMS, [M – H]⁺ = 395.1. ¹H NMR (500 MHz, DMSO-d₆) δ 7.42 (d, J = 7.9 Hz, 2H), 7.35-7.22 (m, 4H), 7.18 (d, J = 9.2 Hz, 1H), 4.09-4.00 (m, J = 7.2, 7.2 Hz, 1H), 3.92 (s, 2H), 3.78 (s, 3H), 3.04-2.94 (m, 1H), 2.68-2.59 (m, 2H), 2.00-1.90 (m, 2H). HPLC-4: RT = 1.61 min; HPLC-5: RT = 2.11 min; purity = 95%. |
| 17 | Cis-2-(3-(2'-fluoro-5'-(trifluoromethoxy)-[1,1'-biphenyl]-4-yl)cyclobutoxy)acetic acid | LCMS, [M – H]⁺ = 383.1. ¹H NMR (500 MHz, DMSO-d₆) δ 7.55-7.32 (m, 7H), 4.20-3.82 (m, 3H), 3.09-2.96 (m, 1H), 2.74-2.59 (m, 2H), 2.09-1.88 (m, 2H). HPLC-4: RT = 1.61 min; HPLC-5: RT = 2.14 min; purity = 98%. |
| 18 | Cis-2-(3-(3'-fluoro-5'-isopropoxy-[1,1'-biphenyl]-4-yl)cyclobutoxy)acetic acid | LCMS, [M – H]⁺ = 357.2. ¹H NMR (500 MHz, DMSO-d₆) δ 7.67-7.51 (m, 2H), 7.39-7.23 (m, 2H), 7.04-6.91 (m, 2H), 6.76 (d, J = 10.7 Hz, 1H), 4.78-4.64 (m, 1H), 4.16-3.77 (m, 3H), 3.10-2.93 (m, 1H), 2.68-2.59 (m, 2H), 2.02-1.83 (m, 2H), 1.28 (d, J = 5.5 Hz, 6H). HPLC-4: RT = 1.62 min; HPLC-5: RT = 2.16 min; purity = 96%. |
| 19 | Cis-2-(3-(3'-isopropoxy-5'-methoxy-[1,1'-biphenyl]-4-yl)cyclobutoxy)acetic acid | LCMS, [M – H]⁺ = 369.2. ¹H NMR (500 MHz, DMSO-d₆) δ 7.59-7.53 (m, 2H), 7.32-7.25 (m, 2H), 6.71 (s, 2H), 6.44 (br. s., 1H), 4.73-4.61 (m, 1H), 4.14-3.84 (m, 3H), 3.78 (s, 3H), 3.08-2.94 (m, 1H), 2.69-2.59 (m, 2H), 2.04-1.87 (m, 2H), 1.27 (d, J = 5.8 Hz, 6H). HPLC-4: RT = 1.54 min; HPLC-5: RT = 2.06 min; purity = 92%. |

Example 20

Cis-2-(3-(2'-fluoro-5'-((6-methylpyridin-3-yl)oxy)-[1,1'-biphenyl]-4-yl)cyclobutoxy) acetic acid

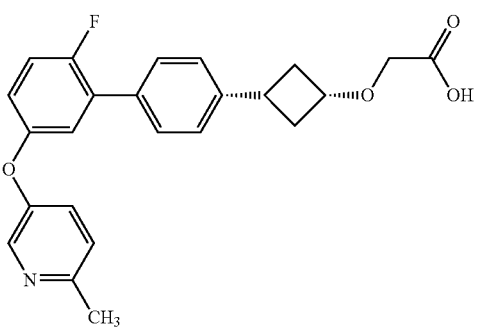

20A. Cis-tert-butyl 2-(3-(4-(4,4,5,5-tetramethyl-1,3,2-dioxaborolan-2-yl)phenyl) cyclobutoxy)acetate

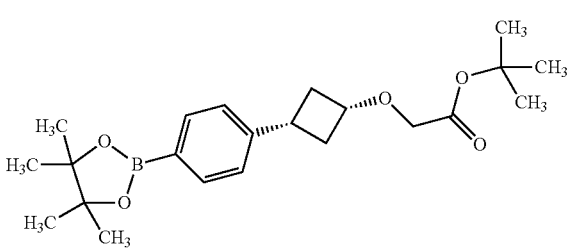 [SMILES: CC(C)(C)OC(=O)CO[C@H]1C[C@@H](c2ccc(B3OC(C)(C)C(C)(C)O3)cc2)C1]

A mixture of cis-tert-butyl 2-(3-(4-bromophenyl)cyclobutoxy)acetate (150 mg, 0.44 mmol), KOAc (129 mg, 1.32 mmol), bis(pinacolato)diboron (134 mg, 0.53 mmol) in DMSO (0.8 mL) was degassed with N₂ for 15 min, after which PdCl₂(dppf) (32 mg, 0.044 mmol) was added and then the mixture was degassed again with N₂ for 15 min. The reaction vessel was sealed and heated at 85° C. for 5 h, then was cooled to rt and filtered. The filter-cake was washed with EtOAc and the combined filtrates were concentrated in vacuo. The residue was chromatographed (SiO₂; 24 g; A=Hexanes, B=EtOAc; 25 min gradient from 0% B:100% A to 20% B:80% A; flow rate=60 mL/min) to give the title compound (95 mg, 0.25 mmol, 56% yield) as a colorless oil. LCMS, [M+Na]⁺=411.3. ¹H NMR (500 MHz, CDCl₃) δ 7.75 (d, J=8.0 Hz, 2H), 7.25 (d, J=7.7 Hz, 2H), 4.12-4.03 (m, 1H), 3.94 (s, 2H), 2.99 (tt, J=10.2, 7.7 Hz, 1H), 2.76-2.67 (m, 2H), 2.20-2.09 (m, 2H), 1.52-1.48 (m, 9H), 1.34 (s, 12H).

20B.
5-(3-Bromo-4-fluorophenoxy)-2-methylpyridine

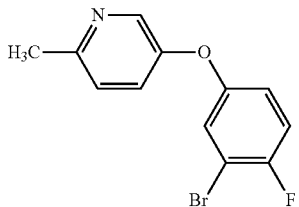 [SMILES: Cc1ccc(Oc2ccc(F)c(Br)c2)cn1]

To a solution of 6-methylpyridin-3-ol (299 mg, 2.74 mmol) and (3-bromo-4-fluorophenyl) boronic acid (500 mg, 2.29 mmol) in DCM (10 mL), 4A° molecular sieves, (0.1 g) and TEA (1.6 mL, 11.4 mmol) and pyridine (0.90 mL, 11.4 mmol) were added, followed by Cu(OAc)$_2$ (830 mg, 4.57 mmol). The reaction was stirred at rt under an atmosphere of air (balloon) overnight. LC-MS showed the reaction was complete at this point. The reaction mixture was filtered; the filtrate was concentrated in vacuo and the crude product was chromatographed (SiO$_2$; 80 g; continuous gradient from 0% to 80% Solvent B:A over 30 min, hold at 80% Solvent B:A for 10 min, where Solvent A=hexanes and Solvent B=EtOAc) to give the title compound (261 mg, 0.92 mmol, 40% yield) as a brown oil. LCMS, [M+H]$^+$=283.9. $^1$H NMR (500 MHz, CDCl$_3$) δ 8.29 (d, J=2.8 Hz, 1H), 7.23-7.07 (m, 4H), 6.96-6.89 (m, 1H), 2.56 (s, 3H).

20C. Cis-tert-butyl 2-(3-(2'-fluoro-5'-phenoxy-[1,1'-biphenyl]-4-yl)cyclobutoxy)acetate

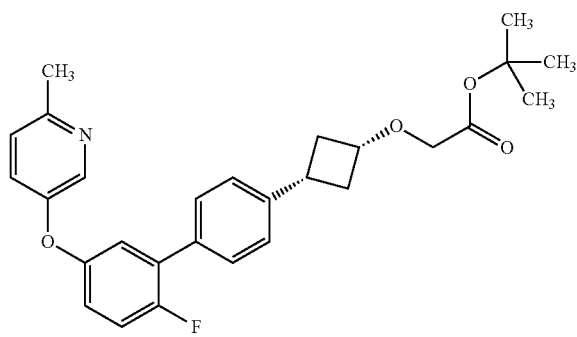 [SMILES: Cc1ccc(Oc2ccc(F)c(-c3ccc([C@H]4C[C@@H](OCC(=O)OC(C)(C)C)C4)cc3)c2)cn1]

A mixture of cis-tert-butyl 2-(3-(4-(4,4,5,5-tetramethyl-1,3,2-dioxaborolan-2-yl)phenyl)cyclobutoxy)acetate (21 mg, 0.05 mmol), 5-(3-bromo-4-fluorophenoxy)-2-methylpyridine (15 mg, 0.05 mmol), (Ph$_3$P)$_4$Pd (6 mg, 5.3 nmol) and K$_2$CO$_3$ (22 mg, 0.16 mmol) in THF (2 mL) and water (0.7 mL) was heated at 130° C. for 20 min under Ar, then was cooled to rt. The reaction mixture was diluted with water (5 mL) and extracted with EtOAc (4×10 mL). The combined organic extracts were dried (MgSO$_4$) and concentrated in vacuo to afford the crude product which was used directly in the next step without further purification. LCMS, [M+Na]$^+$=464.2.

Example 20

To a solution of cis-tert-butyl 2-(3-(2'-fluoro-5'-((6-methylpyridin-3-yl)oxy)-[1,1'-biphenyl]-4-yl)cyclobutoxy)acetate (25 mg, 0.05 mmol) in THF (1 mL)/water (0.5 mL)/MeOH (1 mL) was added KOH (89 mg, 1.59 mmol). The mixture was heated to 80° C. in a microwave vial for 30 min, then was cooled to rt. The mixture was acidified with 1N aq. HCl to pH=2~3, then was extracted with EtOAc (3×10 mL), dried (MgSO$_4$) and concentrated in vacuo to afford the crude product which was purified by preparative LC/MS: Column: Waters XBridge C18, 19×200 mm, 5-μm particles; Guard Column: Waters XBridge C18, 19×10 mm, 5-nm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and dried via centrifugal evaporation to give the title compound (18 mg, 0.05 mmol, 32% yield). LCMS, [M−H]$^+$=406.2. $^1$H NMR (500 MHz, DMSO-d$_6$) δ 8.37 (br. s., 1H), 7.62-7.55 (m, 1H), 7.51-7.29 (m, 6H), 7.23-7.16 (m, 1H), 7.12-7.04 (m, 1H), 4.08-4.00 (m, 1H), 3.96 (br. s., 2H), 3.06-2.95 (m, 1H), 2.68-2.60 (m, 2H), 2.54 (s, 3H), 2.00-1.89 (m, 2H). HPLC-4: RT=1.41 min; HPLC-5: RT=1.33 min; purity=95%.

Examples from Table 2 were prepared using the general synthetic sequence described for the preparation of Example 20.

TABLE 2

Ar—⟨phenyl⟩—⟨cyclobutyl⟩—O—CH$_2$—C(=O)OH

| Ex. No. | Structure (Ar—) and Name | Analytical Data |
|---|---|---|
| 21 | [Structure: 4-fluorophenyl with 5-methyl-1,2,4-oxadiazol-3-yl substituent]<br>Cis-2-(3-(2'-Fluoro-5'-(5-methyl-1,2,4-oxadiazol-3-yl)-[1,1'-biphenyl]-4-yl)cyclobutoxy)acetic acid | LCMS, [M − H]$^+$ = 381.0. $^1$H NMR (500 MHz, DMSO-d$_6$) δ 8.04-7.95 (m, 2H), 7.53-7.44 (m, 3H), 7.36 (d, J = 7.9 Hz, 1H), 4.07-3.97 (m, 1H), 3.90 (s, 2H), 3.06-2.94 (m, 1H), 2.68-2.59 (m, 5H), 2.00-1.88 (m, J = 8.2 Hz, 2H). HPLC-4: RT = 1.37 min; HPLC-5: RT = 1.83 min; purity = 100%. |
| 22 | [Structure: 2-chloropyridine with 3-fluorophenoxy]<br>Cis-2-(3-(4-(2-Chloro-5-(3-fluorophenoxy)pyridin-3-yl)phenyl)cyclobutoxy)acetic acid | LCMS, [M − H]$^+$ = 426.1. $^1$H NMR (500 MHz, DMSO-d$_6$) δ 8.23 (d, J = 2.7 Hz, 1H), 7.53 (d, J = 2.7 Hz, 1H), 7.47-7.38 (m, 3H), 7.33 (d, J = 7.9 Hz, 2H), 7.09-6.95 (m, 3H), 3.97-3.90 (m, 1H), 3.60 (s, 2H), 3.05-2.94 (m, 1H), 2.68-2.57 (m, 2H), 2.01-1.85 (m, J = 7.3 Hz, 2H). HPLC-4: RT = 1.58 min; HPLC-5: RT = 2.05 min; purity = 97%. |

TABLE 2-continued

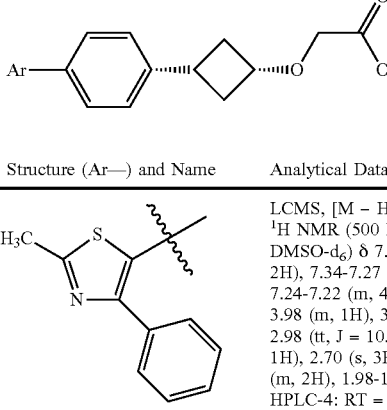

| Ex. No. | Structure (Ar—) and Name | Analytical Data |
|---|---|---|
| 23 | ![structure] Cis-2-(3-(4-(2-Methyl-4-phenylthiazol-5-yl)phenyl) cyclobutoxy)acetic acid | LCMS, [M − H]⁺ = 378.1. $^1$H NMR (500 MHz, DMSO-$d_6$) δ 7.45-7.40 (m, 2H), 7.34-7.27 (m, 3H), 7.24-7.22 (m, 4H), 4.07-3.98 (m, 1H), 3.95 (s, 2H), 2.98 (tt, J = 10.3, 7.6 Hz, 1H), 2.70 (s, 3H), 2.66-2.57 (m, 2H), 1.98-1.88 (m, 2H). HPLC-4: RT = 1.33 min; HPLC-5: RT = 1.69 min; purity = 99%. |

Example 24

Cis-2-(3-(4-(5-chloro-2,2-dimethyl-2,3-dihydrobenzofuran-7-yl)phenyl)cyclobutoxy) acetic acid

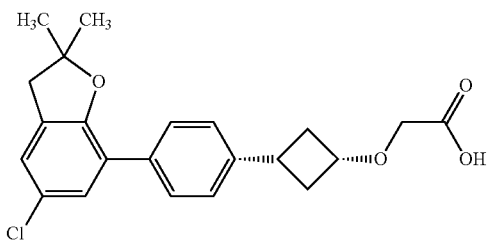

24A. Cis-tert-butyl 2-(3-(5'-chloro-2'-hydroxy-[1,1'-biphenyl]-4-yl)cyclobutoxy)acetate

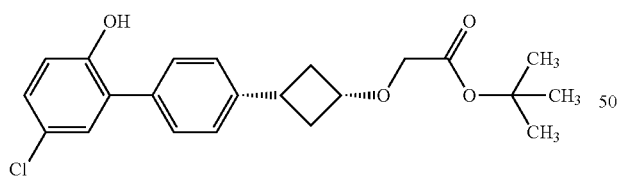

A mixture of cis-tert-butyl 2-(3-(4-bromophenyl)cyclobutoxy)acetate (60 mg, 0.18 mmol), (5-chloro-2-hydroxyphenyl)boronic acid (36 mg, 0.21 mmol), (Ph$_3$P)$_4$Pd (20 mg, 0.02 mmol) and K$_2$CO$_3$ (73 mg, 0.53 mmol) in THF (2 mL) and water (0.7 mL) was heated at 80° C. for 8 h under Ar, then was cooled to rt. The reaction was acidified with 1N aq. HCl to pH=2-3, and extracted with EtOAc (4×10 mL). The combined organic extracts were dried (MgSO$_4$) and concentrated in vacuo to afford the crude product, which was chromatographed (SiO$_2$; 12 g; eluted with EtOAc/Hexanes 0% to 30% over 20 min) to give the title compound (42 mg, 0.11 mmol, 61% yield) as a beige solid. LCMS, [M+Na]⁺=410.9. $^1$H NMR (500 MHz, CDCl$_3$) δ 7.41-7.35 (m, 4H), 7.22-7.18 (m, 2H), 6.94-6.90 (m, 1H), 4.17-4.05 (m, 1H), 3.96 (s, 2H), 3.10-2.99 (m, 1H), 2.82-2.69 (m, 2H), 2.24-2.12 (m, 2H), 1.51 (s, 9H).

24B. Cis-tert-butyl 2-(3-(5'-chloro-2'-((2-methylallyl)oxy)-[1,1'-biphenyl]-4-yl)cyclobutoxy)acetate

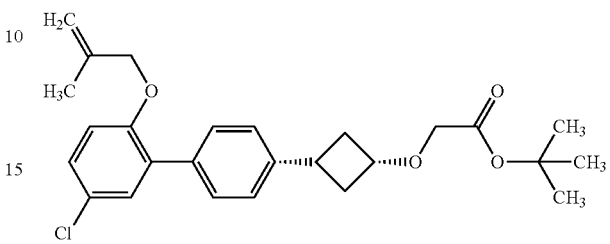

A mixture of cis-tert-butyl 2-(3-(5'-chloro-2'-hydroxy-[1,1'-biphenyl]-4-yl)cyclobutoxy) acetate (40 mg, 0.10 mmol) K$_2$CO$_3$ (31 mg, 0.23 mmol and KI (0.85 mg, 5.14 nmol) in DMF (1.2 mL) was heated to 65° C. under N$_2$, and 3-chloro-2-methylprop-1-ene (0.02 mL, 0.21 mmol) was added. The reaction mixture was heated at 65° C. under N$_2$ for 16 h, then was cooled to rt. LC/MS indicated the formation of the desired product. Water (5 mL) and EtOAc (10 mL) were added, and the organic layer was washed with H$_2$O (3 mL) and brine (5 mL), dried (MgSO$_4$) and concentrated in vacuo. The residue was chromatographed (SiO$_2$; 8 g; continuous gradient from 0 to 15% Solvent B:A over 15 min, hold at 15% Solvent B:A for 10 min, where Solvent A=hexanes and Solvent B=EtOAc) to give the title compound (42 mg, 0.10 mmol, 92% yield) as a colorless oil. LCMS, [M+H]⁺=465.2. $^1$H NMR (500 MHz, CDCl$_3$) δ 7.47 (d, J=7.2 Hz, 2H), 7.33-7.28 (m, 3H), 7.22 (dt, J=8.8, 1.2 Hz, 1H), 6.88 (d, J=8.8 Hz, 1H), 5.00 (s, 1H), 4.93 (s, 1H), 4.40 (s, 2H), 4.14-4.04 (m, 1H), 3.95 (s, 2H), 3.08-2.96 (m, 1H), 2.80-2.69 (m, 2H), 2.24-2.12 (m, 2H), 1.75 (s, 3H), 1.53-1.47 (s, 9H).

24C. Cis-2-(3-(5'-chloro-2'-hydroxy-3'-(2-methylallyl)-[1,1'-biphenyl]-4-yl)cyclobutoxy) acetic acid

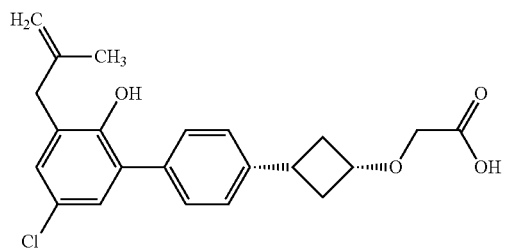

Cis-tert-Butyl 2-(3-(5'-chloro-2'-((2-methylallyl)oxy)-[1,1'-biphenyl]-4-yl) cyclobutoxy)acetate (40 mg, 0.09 mmol) was azeotroped several times from toluene and then heated neat in a heating block for 16 h at 195° C. LC/MS indicated the presence of the desired product. The brown liquid was carried on to the next step without any further purification. LCMS, [M−H]⁺=385.1.

Example 24

A solution of cis-2-(3-(5'-chloro-2'-hydroxy-3'-(2-methylallyl)-[1,1'-biphenyl]-4-yl)cyclobutoxy)acetic acid (40 mg, 0.10 mmol) in formic acid (0.5 mL) and water (0.05 mL) was heated at 110° C. for 30 h. Volatiles were removed in vacuo and the residue was azeotroped with toluene. The crude product was purified by preparative LC/MS using the following conditions: Column: Waters XBridge C18, 19×200 mm, 5-μm particles; Guard Column: Waters XBridge C18, 19×10 mm, 5-μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and dried via centrifugal evaporation to provide the title compound (14 mg, 0.04 mmol, 35% yield). LCMS, [M−H]$^+$=385.1. $^1$H NMR (500 M Hz, DMSO-d$_6$) δ 7.60 (d, J=7.7 Hz, 2H), 7.32-7.25 (m, 3H), 7.21 (s, 1H), 4.04 (quin, J=7.2 Hz, 1H), 3.92 (s, 2H), 3.06 (s, 2H), 2.98 (quin, J=8.8 Hz, 1H), 2.67-2.57 (m, 2H), 2.00-1.89 (m, 2H), 1.43 (s, 6H). HPLC-4: RT=1.76 min; HPLC-5: RT=2.30 min; purity=99%.

Example 25

Cis-2-(3-(2'-fluoro-5'-(pyridin-4-yloxy)-[1,1'-biphenyl]-4-yl)cyclobutoxy)acetic acid

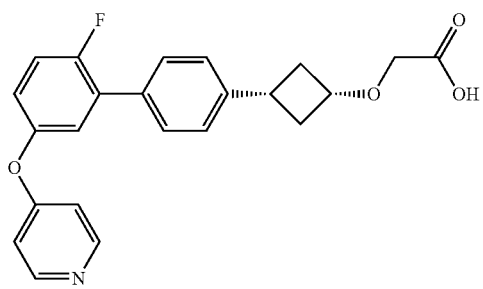 [SMILES: O=C(O)CO[C@H]1C[C@@H](c2ccc(-c3cc(Oc4ccncc4)ccc3F)cc2)C1]

25A. Cis-tert-butyl 2-(3-(2'-fluoro-5'-hydroxy-[1,1'-biphenyl]-4-yl)cyclobutoxy)acetate

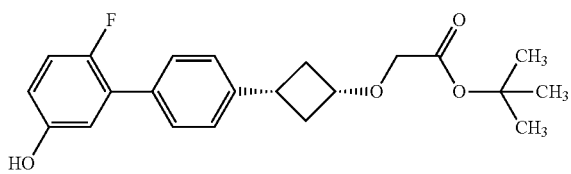

A mixture of cis-tert-butyl 2-(3-(4-bromophenyl)cyclobutoxy)acetate (450 mg, 1.32 mmol), (5-((tert-butyldimethylsilyl)oxy)-2-fluorophenyl)boronic acid (356 mg, 1.32 mmol), (Ph$_3$P)$_4$Pd (152 mg, 0.13 mmol) and K$_2$CO$_3$ (547 mg, 3.96 mmol) in THF (2 mL) and water (0.7 mL) was heated in a microwave reactor at 130° C. for 20 min under Ar, then was cooled to rt. The reaction was acidified with 1N aq. HCl to pH=2-3, and extracted with EtOAc (4×15 mL). The combined organic fractions were dried (MgSO$_4$), and concentrated in vacuo. The residue was chromatographed (SiO$_2$; 80 g; gradient of EtOAc/Hexanes (0% to 30% over 30 min) to give the title compound (151 mg, 0.41 mmol, 31% yield) as a light yellow colored oil. LCMS, [M+Na]$^+$=395.2. $^1$H NMR (500 MHz, CDCl$_3$) δ 7.48 (dd, J=8.3, 1.7 Hz, 2H), 7.31 (d, J=8.3 Hz, 2H), 7.04-6.98 (m, 1H), 6.92-6.86 (m, 1H), 6.75 (dt, J=8.8, 3.4 Hz, 1H), 4.16-4.04 (m, 1H), 3.96 (s, 2H), 3.02 (tt, J=10.3, 7.7 Hz, 1H), 2.79-2.70 (m, 2H), 2.18 (tdt, J=10.9, 8.2, 2.6 Hz, 2H), 1.49 (s, 9H).

Example 25

A mixture of cis-tert-butyl 2-(3-(2'-fluoro-5'-hydroxy-[1,1'-biphenyl]-4-yl) cyclobutoxy)acetate (15 mg, 0.04 mmol), 4-bromopyridine hydrochloride (24 mg, 0.12 mmol), and K$_2$CO$_3$ (28 mg, 0.20 mmol) in DMF (0.5 mL) was stirred at 150° C. overnight, after which LCMS showed the reaction was completed. After cooling to rt, volatiles were removed in vacuo. The crude product was dissolved in THF (1 mL)/water (0.5 mL)/MeOH (1 mL), and KOH (84 mg, 1.5 mmol) was added. The mixture was stirred at RT overnight, then was acidified with 1N aq. HCl to pH=2-3. The mixture was extracted with EtOAc (3×10 mL). The combined organic extracts were dried (MgSO$_4$) and concentrated in vacuo to afford the crude product, which was purified by preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and dried via centrifugal evaporation to provide the title compound (19 mg, 0.05 mmol, 96% yield). LCMS, [M−H]$^+$=392.1. $^1$H NMR (500 MHz, DMSO-d$_6$) δ 7.56-7.44 (m, 5H), 7.36-7.28 (m, 6H), 4.04 (m, 1H), 3.96 (s, 2H), 3.07-2.97 (m, 1H), 2.69-2.60 (m, 2H), 2.02-1.87 (m, 2H). HPLC-4: RT=1.32 min; HPLC-5: RT=1.32 min; purity=99%.

Examples from Table 3 were prepared using the general synthetic sequence described for the preparation of Example 25.

TABLE 3

| Ex. No. | Structure (Ar—) and Name | Analytical Data |
|---|---|---|
| 26 | Cis-2-(3-(2'-fluoro-5'-(pyridin-2-yloxy)-[1,1'-biphenyl]-4-yl) cyclobutoxy) acetic acid | LCMS, [M − H]$^+$ = 392.1. $^1$H NMR (500 MHz, DMSO-d$_6$) δ 8.14 (d, J = 4.6 Hz, 1H), 7.86 (t, J = 7.6 Hz, 1H), 7.49 (d, J = 7.6 Hz, 2H), 7.38-7.30 (m, 3H), 7.26 (d, J = 4.0 Hz, 1H), 7.18-7.10 (m, 2H), 7.06 (d, J = 8.2 Hz, 1H), 4.10-3.99 (m, 1H), 3.92 (s, 2H), 3.07-2.95 (m, 1H), 2.69-2.59 (m, 2H), 2.01-1.89 (m, 2H). HPLC-4: RT = 1.42 min; HPLC-5: RT = 1.89 min; purity = 96%. |

TABLE 3-continued

| Ex. No. | Structure (Ar—) and Name | Analytical Data |
|---|---|---|
| 27 | Cis-2-(3-(2'-fluoro-5'-((2-methylthiazol-5-yl)oxy)-[1,1'-biphenyl]-4-yl)cyclobutoxy)acetic acid | LCMS, [M − H]⁺ = 412.1. $^1$H NMR (500 MHz, CDCl$_3$) δ 7.48-7.43 (m, 2H), 7.31-7.28 (m, 2H), 7.22 (s, 1H), 7.15-7.07 (m, 2H), 7.03-6.98 (m, 1H), 4.16-4.07 (m, 1H), 4.05 (s, 2H), 3.11-2.99 (m, 1H), 2.80-2.70 (m, 2H), 2.63 (s, 3H), 2.20-2.11 (m, 2H). HPLC-4: RT = 1.44 min; HPLC-5: RT = 1.87 min; purity = 100%. |
| 28 | Cis-2-(3-(2'-fluoro-5'-(pyridin-3-yloxy)-[1,1'-biphenyl]-4-yl)cyclobutoxy)acetic acid | LCMS, [M − H]⁺ = 392.1. $^1$H NMR (500 MHz, DMSO-d$_6$) δ 7.54-7.45 (m, 4H), 7.40-7.30 (m, 5H), 7.25-7.20 (m, 1H), 7.13-7.06 (m, J = 8.5 Hz, 1H), 4.09-4.00 (m, 1H), 3.95 (s, 2H), 3.07-2.96 (m, 1H), 2.69-2.59 (m, 2H), 2.01-1.90 (m, 2H). HPLC-4: RT = 1.34 min; HPLC-5: RT = 1.37 min; purity = 100%. |
| 29 | Cis-2-(3-(2'-fluoro-5'-((6-methylpyridazin-3-yl)oxy)-[1,1'-biphenyl]-4-yl)cyclobutoxy)acetic acid | LCMS, [M − H]⁺ = 407.1. $^1$H NMR (500 MHz, DMSO-d$_6$) δ 7.63 (d, J = 9.2 Hz, 1H), 7.52-7.45 (m, 2H), 7.40-7.28 (m, 5H), 7.24-7.16 (m, 1H), 4.03 (quin, J = 7.3 Hz, 1H), 3.95 (s, 2H), 3.06-2.94 (m, 1H), 2.68-2.59 (m, 2H), 2.53 (s, 3H), 2.00-1.89 (m, 2H). HPLC-4: RT = 1.20 min; HPLC-5: RT = 1.42 min; purity = 99%. |

Example 30

Cis2-(3-(2'-fluoro-5'-((tetrahydro-2H-pyran-3-yl)oxy)-[1,1'-biphenyl]-4-yl)cyclobutoxy)acetic acid

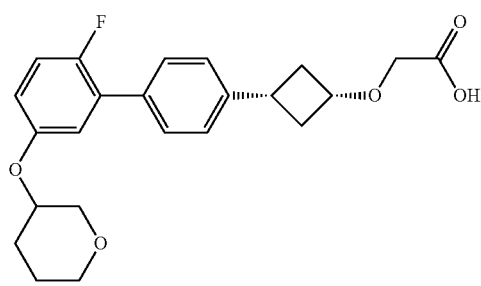 [SMILES: O=C(O)CO[C@H]1C[C@@H](c2ccc(-c3cc(OC4CCCOC4)ccc3F)cc2)C1]

To a 0° C. mixture of cis-tert-butyl 2-(3-(2'-fluoro-5'-hydroxy-[1,1'-biphenyl]-4-yl)cyclobutoxy)acetate (20 mg, 0.05 mmol), tetrahydro-2H-pyran-3-ol (11 mg, 0.11 mmol), Ph$_3$P (28 mg, 0.11 mmol) and THF (0.5 mL) was added DIAD (0.02 mL, 0.11 mmol) dropwise over 2 min. The reaction was allowed to slowly warm to rt overnight under Ar. Volatiles were removed in vacuo and the residue was chromatographed (SiO$_2$; 8 g; continuous gradient from 0 to 50% Solvent B:A over 20 min, hold at 50% Solvent B for 10 min, where Solvent A=hexanes and Solvent B=EtOAc) to give cis-tert-butyl 2-(3-(2'-fluoro-5'-((tetrahydro-2H-pyran-3-yl)oxy)-[1,1'-biphenyl]-4-yl)cyclobutoxy) acetate. This ester was dissolved in THF (1 mL)/water (0.5 mL)/MeOH (1 mL) and KOH (91 mg, 1.62 mmol) was added. The mixture was heated in a microwave reactor for 30 min, then was cooled to rt. The mixture was acidified with 1N aq. HCl to pH=2-3. The mixture was extracted with EtOAc (3×10 mL), dried (MgSO$_4$) and concentrated in vacuo. The residue was purified by preparative LC/MS with the following conditions: Column: Waters XBridge C18, 19×200 mm, 5-nm particles; Guard Column: Waters XBridge C18, 19×10 mm, 5-nm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and dried via centrifugal evaporation. The title compound (0.3 mg, 0.71 μmol, 1.3% yield) was obtained. LCMS, [M−H]⁺=399.2. $^1$H NMR (500 MHz, DMSO-d$_6$) δ 7.48 (d, J=6.9 Hz, 2H), 7.32 (d, J=8.0 Hz, 2H), 7.22-7.15 (m, 1H), 7.02 (dd, J=6.3, 3.0 Hz, 1H), 6.96 (dt, J=9.0, 3.5 Hz, 1H), 4.39 (tt, J=6.7, 3.6 Hz, 1H), 4.11-3.99 (m, 1H), 3.85-3.76 (m, 3H), 3.62 (ddd, J=10.9, 6.6, 3.7 Hz, 1H), 3.54-3.45 (m, 2H), 3.06-2.95 (m, 1H), 2.68-2.58 (m, 2H), 2.05-1.88 (m, 3H), 1.82-1.63 (m, 2H), 1.58-1.44 (m, 1H). HPLC-4: RT=1.43 min; HPLC-5: RT=1.90 min; purity=95%.

Example 31

Cis-2-(3-(2'-fluoro-5'-(p-tolyloxy)-[1,1'-biphenyl]-4-yl)cyclobutoxy)acetic acid

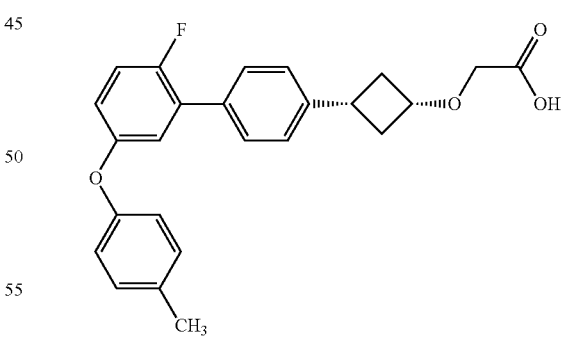

To a mixture of cis-tert-butyl 2-(3-(2'-fluoro-5'-hydroxy-[1,1'-biphenyl]-4-yl)cyclobutoxy) acetate (15 mg, 0.04 mmol), p-tolylboronic acid (11 mg, 0.08 mmol), 4A° molecular sieves, (0.1 g), TEA (0.03 mL, 0.20 mmol) and Py (0.02 mL, 0.20 mmol) in DCM (0.5 mL) was added Cu(OAc)$_2$ (15 mg, 0.08 mmol). The reaction mixture was stirred at rt under an atmosphere of air overnight (at this point LC-MS showed the reaction was complete), then was filtered; the filtrate was concentrated in vacuo. This crude product was dissolved in THF (1 mL)/water (0.5 mL)/ MeOH (1 mL) and KOH (67 mg, 1.20 mmol) was added. The reaction mixture was stirred at 80° C. in a microwave for 30 min, then was cooled to rt. The mixture was acidified with 1N aq. HCl to pH=2-3. The mixture was extracted with EtOAc (3×10 mL); the combined organic extracts were dried (MgSO$_4$) and concentrated in vacuo. The residue was purified by preparative LC/MS using the following conditions: Column: Waters XBridge C18, 19×200 mm, 5-μm particles; Guard Column: Waters XBridge C18, 19×10 mm, 5-μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and dried via centrifugal evaporation to provide the title compound (12 mg, 0.03 mmol, 75% yield). LCMS, [M−H]$^+$=405.2. $^1$H NMR (500 MHz, DMSO-d$_6$) δ 7.41 (d, J=7.6 Hz, 2H), 7.33-7.23 (m, 3H), 7.17 (d, J=8.2 Hz, 2H), 7.03-6.88 (m, 4H), 4.06-3.96 (m, 1H), 3.91 (s, 2H), 3.04-2.91 (m, 1H), 2.66-2.56 (m, 2H), 2.25 (s, 3H), 1.98-1.86 (m, 2H). HPLC-4: RT=1.84 min; HPLC-5: RT=2.34 min; purity=100%.

Example 32

Cis-2-(3-(2'-fluoro-5'-(3-fluorophenoxy)-[1,1'-biphenyl]-4-yl)cyclobutoxy)acetic acid

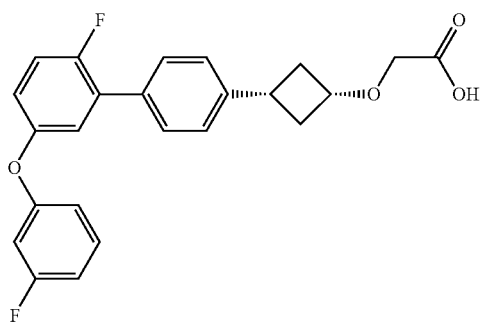 [SMILES: O=C(O)CO[C@H]1C[C@@H](c2ccc(-c3cc(Oc4cccc(F)c4)ccc3F)cc2)C1]

The title compound was prepared from 3-fluorophenylboronic acid using a synthetic sequence analogous to that used to prepare Example 31. The title compound (11 mg, 0.03 mmol, 66% yield) was obtained. LCMS, [M−H]$^+$=409.1. $^1$H NMR (500 MHz, DMSO-d$_6$) δ 7.50-7.29 (m, 6H), 7.18 (dd, J=6.4, 2.7 Hz, 1H), 7.10-7.05 (m, 1H), 6.94 (t, J=8.4 Hz, 1H), 6.90-6.81 (m, 2H), 4.03 (quin, J=7.2 Hz, 1H), 3.92 (s, 2H), 2.99 (quin, J=8.8 Hz, 1H), 2.68-2.58 (m, 2H), 2.00-1.86 (m, 2H). HPLC-4: RT=1.76 min; HPLC-5: RT=2.25 min; purity=100%.

Example 33

Cis-2-(3-(5'-(cyclohexyloxy)-2'-fluoro-[1,1'-biphenyl]-4-yl)cyclobutoxy)acetic acid

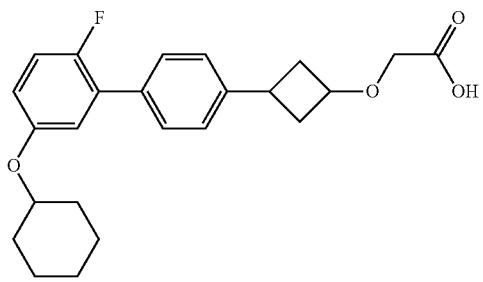 [SMILES: O=C(O)COC1CC(c2ccc(-c3cc(OC4CCCCC4)ccc3F)cc2)C1]

NaH (3 mg, 0.08 mmol, 60% in mineral oil) was added to a solution of cis-tert-butyl 2-(3-(2'-fluoro-5'-hydroxy-[1,1'-biphenyl]-4-yl)cyclobutoxy)acetate (15 mg, 0.04 mmol) in DMF (0.5 mL) at 0° C. After 30 min, iodocyclohexane (85 mg, 0.40 mmol) was added and the reaction was stirred at 50° C. for 4 h, then was cooled to rt. A mixture of THF (1 mL), H$_2$O (0.5 mL), MeOH (1 mL) and two pellets of KOH were added; the reaction was stirred at rt overnight. The mixture was acidified with 1N aq. HCl to pH=2-3. The mixture was extracted with EtOAc (3×10 mL), dried (MgSO$_4$) and concentrated in vacuo. The residue was purified by preparative LC/MS using the following conditions: Column: Waters XBridge C18, 19×200 mm, 5-μm particles; Guard Column: Waters XBridge C18, 19×10 mm, 5-μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5 min hold at 100% B; Flow: 20 mL/min. Fractions containing the desired product were combined and dried via centrifugal evaporation to provide the title compound (4 mg, 9.3 μmol, 23% yield). LCMS, [M−H]$^+$=397.2. $^1$H NMR (500 MHz, DMSO-d$_6$) δ 7.45 (d, J=7.3 Hz, 2H), 7.31 (d, J=7.9 Hz, 2H), 7.16 (t, J=9.6 Hz, 1H), 6.97-6.88 (m, 2H), 4.36-4.27 (m, 1H), 4.03 (s, 1H), 3.92 (s, 2H), 3.05-2.94 (m, 1H), 2.68-2.59 (m, 2H), 2.00-1.83 (m, 4H), 1.75-1.62 (m, 2H), 1.55-1.16 (m, 6H). HPLC-4: RT=1.82 min; HPLC-5: RT=2.39 min; purity=100%.

Example 34

Cis-2-(3-(2',3'-difluoro-5'-(4-fluorophenoxy)-[1,1'-biphenyl]-4-yl)cyclobutoxy)acetic acid

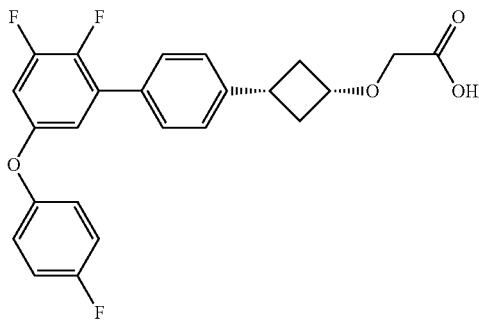 [SMILES: O=C(O)CO[C@H]1C[C@@H](c2ccc(-c3cc(Oc4ccc(F)cc4)cc(F)c3F)cc2)C1]

34A. Cis-tert-butyl 2-(3-(2',3'-difluoro-5'-hydroxy-[1,1'-biphenyl]-4-yl)cyclobutoxy) acetate

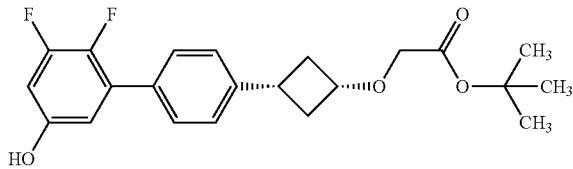 [SMILES: CC(C)(C)OC(=O)CO[C@H]1C[C@@H](c2ccc(-c3cc(O)cc(F)c3F)cc2)C1]

A mixture of cis-tert-butyl 2-(3-(4-bromophenyl)cyclobutoxy)acetate (15 mg, 0.04 mmol), (5-((tert-butyldimethylsilyl)oxy)-2,3-difluorophenyl)boronic acid (19 mg, 0.07 mmol), (Ph$_3$P)$_4$Pd (5 mg, 4.40 µmol) and K$_2$CO$_3$ (18 mg, 0.13 mmol) in THF (2 mL) and water (0.7 mL) was heated in a microwave reactor at 130° C. for 20 min under Ar, then was cooled to rt. The reaction was acidified with 1N aq. HCl to pH=~2-3, and extracted with EtOAc (4×10 mL). The organic fractions were combined, dried (MgSO$_4$), and concentrated in vacuo. The residue was chromatographed (SiO$_2$; 8 g; EtOAc/Hexanes (0% EtOAc to 40% EtOAc over 20 min) to give the title compound (16 mg, 0.03 mmol, 70% yield) as a colorless oil. LCMS, [M−H]$^+$=389.2. $^1$H NMR (500 MHz, CDCl$_3$) δ 7.45 (dd, J=8.0, 1.4 Hz, 2H), 7.31 (d, J=8.3 Hz, 2H), 6.73-6.62 (m, 2H), 4.13-4.03 (m, 1H), 3.97 (s, 2H), 3.07-2.97 (m, 1H), 2.78-2.69 (m, 2H), 2.22-2.13 (m, 2H), 1.51 (s, 9H).

34B. Cis-tert-butyl 2-(3-(2',3'-difluoro-5'-hydroxy-[1,1'-biphenyl]-4-yl)cyclobutoxy) acetate

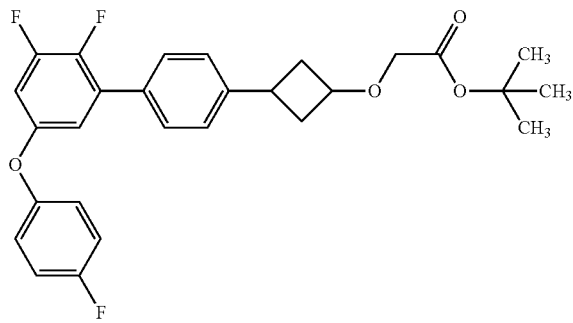 [SMILES: CC(C)(C)OC(=O)COC1CC(c2ccc(-c3cc(Oc4ccc(F)cc4)cc(F)c3F)cc2)C1]

To a mixture of cis-tert-butyl 2-(3-(2',3'-difluoro-5'-hydroxy-[1,1'-biphenyl]-4-yl)cyclobutoxy) acetate (13 mg, 0.03 mmol), (4-fluorophenyl)boronic acid (9 mg, 0.07 mmol), molecular sieves, 4A° (0.1 g), TEA (0.02 mL, 0.17 mmol) and pyridine (0.01 mL, 0.17 mmol) in DCM (0.5 mL) was added CuOAc$_2$ (12 mg, 0.07 mmol). The reaction was stirred at rt under an atmosphere of air overnight, then was filtered. The filtrate was dissolved in EtOAc (15 mL), washed with 1N aq. HCl and water, dried (MgSO$_4$) and concentrated in vacuo. The crude product was chromatographed (SiO$_2$; 8 g; gradient of EtOAc/Hexanes (0% EtOAc to 25% EtOAc over 15 min) to give the title compound (12 mg, 0.02 mmol, 71% yield) as a clear oil. $^1$H NMR (500 MHz, CDCl$_3$) δ 7.46-7.42 (m, 2H), 7.32 (d, J=8.3 Hz, 2H), 7.11-6.99 (m, 4H), 6.83-6.71 (m, 2H), 4.17-4.04 (m, 1H), 3.95 (s, 3H), 3.08-2.97 (m, 1H), 2.80-2.67 (m, 2H), 2.23-2.11 (m, 2H), 1.53-1.48 (m, 9H).

Example 34

LiOH.H$_2$O (4 mg, 0.09 mmol) was added to a solution of cis-tert-butyl 2-(3-(2',3'-difluoro-5'-(4-fluorophenoxy)-[1,1'-biphenyl]-4-yl)cyclobutoxy)acetate (11 mg, 0.02 mmol) in THF (1 mL) and water (0.5 mL) at rt. The reaction was stirred at rt overnight, then was diluted with EtOAc (20 mL) and H$_2$O (5 mL). The aqueous layer was acidified with 1N aq. HCl to pH ~3. The organic layer was washed with brine (5 mL), dried (MgSO$_4$) and concentrated in vacuo. The crude product was purified by preparative LC/MS using the following conditions: Column: Waters XBridge C18, 19×200 mm, 5-nm particles; Guard Column: Waters XBridge C18, 19×10 mm, 5-µm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5 min hold at 100% B; Flow: 20 mL/min. Fractions containing the desired product were combined and dried via centrifugal evaporation to provide the title compound (8 mg, 0.02 mmol, 81% yield). LCMS, [M−H]$^+$=427.1. $^1$H NMR (500 MHz, DMSO-d$_6$) δ 7.48 (d, J=7.2 Hz, 2H), 7.34 (d, J=8.0 Hz, 2H), 7.28-7.22 (m, 2H), 7.19-7.11 (m, 3H), 6.95-6.90 (m, 1H), 4.05 (quin, J=7.2 Hz, 1H), 3.91 (s, 2H), 3.06-2.95 (m, 1H), 2.68-2.60 (m, 2H), 2.00-1.90 (m, 2H). HPLC-4: RT=1.86 min; HPLC-5: RT=2.32 min; purity=100%.

Examples from Table 4 were prepared using the general synthetic sequence described for the preparation of Example 34.

TABLE 4

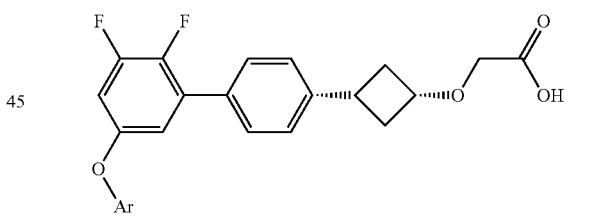

| Ex. No. | Structure (Ar—) and Name | Analytical Data |
|---|---|---|
| 35 | 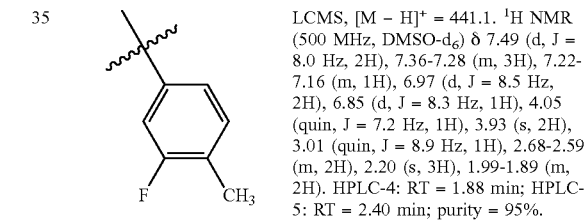<br>Cis-2-(3-(2',3'-difluoro-5'-(3-fluoro-4-methylphenoxy)-[1,1'-biphenyl]-4-yl)cyclobutoxy)acetic acid | LCMS, [M − H]$^+$ = 441.1. $^1$H NMR (500 MHz, DMSO-d$_6$) δ 7.49 (d, J = 8.0 Hz, 2H), 7.36-7.28 (m, 3H), 7.22-7.16 (m, 1H), 6.97 (d, J = 8.5 Hz, 2H), 6.85 (d, J = 8.3 Hz, 1H), 4.05 (quin, J = 7.2 Hz, 1H), 3.93 (s, 2H), 3.01 (quin, J = 8.9 Hz, 1H), 2.68-2.59 (m, 2H), 2.20 (s, 3H), 1.99-1.89 (m, 2H). HPLC-4: RT = 1.88 min; HPLC-5: RT = 2.40 min; purity = 95%. |

TABLE 4-continued

[Structure showing difluoro-phenyl with Ar-O substituent, biphenyl, cyclobutoxy-acetic acid]

| Ex. No. | Structure (Ar—) and Name | Analytical Data |
|---|---|---|
| 36 | [3-fluorophenyl structure]<br>Cis-2-(3-(2',3'-difluoro-5'-(3-fluorophenoxy)-[1,1'-biphenyl]-4-yl)cyclobutoxy)acetic acid | LCMS, [M − H]⁺ = 427.1. ¹H NMR (500 MHz, DMSO-d₆) δ 7.51 (d, J = 7.7 Hz, 2H), 7.47-7.33 (m, 3H), 7.29-7.23 (m, 1H), 7.06-6.96 (m, 3H), 6.92 (d, J = 8.3 Hz, 1H), 4.05 (quin, J = 7.1 Hz, 1H), 3.93 (s, 2H), 3.02 (quin, J = 8.9 Hz, 1H), 2.68-2.59 (m, 2H), 2.00-1.90 (m, 2H). HPLC-4: RT = 1.76 min; HPLC-5: RT = 2.26 min; purity = 96%. |
| 37 | [pyridyl structure with CH₃]<br>Cis-2-(3-(2',3'-difluoro-5'-(3-fluorophenoxy)-[1,1'-biphenyl]-4-yl)cyclobutoxy)acetic acid | LCMS, [M − H]⁺ = 424.1. ¹H NMR (500 MHz, DMSO-d₆) δ 8.33 (d, J = 2.8 Hz, 1H), 7.51-7.47 (m, 3H), 7.37-7.29 (m, 3H), 7.25-7.17 (m, 1H), 7.00-6.95 (m, 1H), 4.09-4.01 (m, 1H), 3.96 (s, 2H), 3.07-2.97 (m, 1H), 2.68-2.60 (m, 2H), 2.47 (s, 3H), 2.00-1.90 (m, 2H). HPLC-4: RT = 1.48 min; HPLC-5: RT = 1.43 min; purity = 95%. |
| 38 | [p-tolyl structure with CH₃]<br>Cis-2-(3-(2',3'-difluoro-5'-(p-tolyloxy)-[1,1'-biphenyl]-4-yl)cyclobutoxy)acetic acid | LCMS, [M − H]⁺ = 423.1. ¹H NMR (500 MHz, DMSO-d₆) δ 7.44 (d, J = 7.6 Hz, 2H), 7.33 (d, J = 7.9 Hz, 2H), 7.21 (d, J = 7.9 Hz, 2H), 7.08-6.95 (m, 3H), 6.86-6.80 (m, 1H), 4.06-3.98 (m, 1H), 3.91 (s, 2H), 3.04-2.94 (m, 1H), 2.66-2.57 (m, 2H), 2.28 (s, 3H), 1.98-1.87 (m, 2H). HPLC-4: RT = 1.88 min; HPLC-5: RT = 2.41 min; purity = 98%. |

Example 39

Trans-2-(3-(2'-fluoro-5'-phenoxy-[1,1'-biphenyl]-4-yl)cyclobutoxy)acetic acid

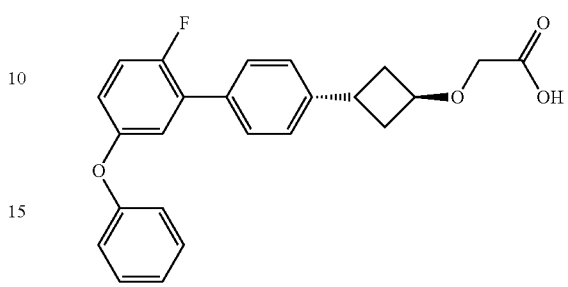

39A. Trans-3-(4-bromophenyl)cyclobutyl benzoate

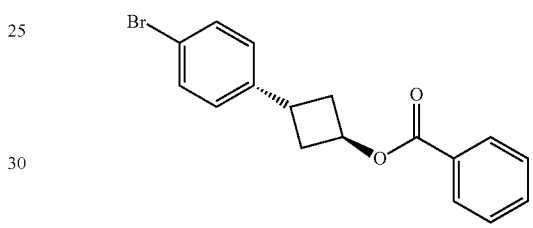

To a solution of cis-3-(4-bromophenyl)cyclobutanol (80 mg, 0.35 mmol), benzoic acid (95 mg, 0.78 mmol) and Ph₃P (185 mg, 0.71 mmol) in THF (0.5 mL) was added DIAD (0.14 mL, 0.71 mmol) dropwise at rt. The reaction was stirred overnight at RT under Ar (LC-MS showed that the reaction was complete), then was concentrated in vacuo to afford the crude product. This material was chromatographed (SiO₂; 12 g; continuous gradient from 0 to 20% Solvent B over 25 min, hold at 20% Solvent B for 10 min, where Solvent A=Hexanes and Solvent B=EtOAc) to give the desired product (92 mg, 0.28 mmol, 79% yield) as a white solid. LCMS, [M+H]⁺=331.0. ¹H NMR (500 MHz, CDCl₃) δ 8.11-8.08 (m, 2H), 7.61-7.56 (m, 1H), 7.50-7.45 (m, 4H), 7.19-7.16 (m, 2H), 5.46-5.40 (m, 1H), 3.77-3.69 (m, 1H), 2.77-2.61 (m, 4H).

39B. Trans-3-(4-bromophenyl)cyclobutanol

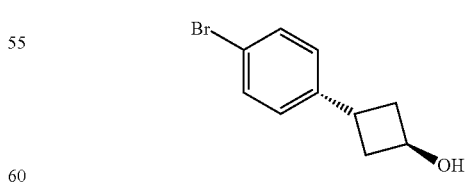

LiOH.H₂O (46 mg, 1.09 mmol) was added to a solution of trans-3-(4-bromophenyl)cyclobutyl benzoate (90 mg, 0.27 mmol) in THF (1 mL), water (0.5 mL) and MeOH (1 mL) at rt. The reaction was stirred at rt overnight, then was diluted with EtOAc (5 mL) and H₂O (10 mL). The layers were separated. The aqueous layer was washed with EtOAc (2×5 mL). The combined organic washes were extracted with H$_2$O (3×10 mL). The combined aqueous layers were acidified with 1N aq. HCl to pH ~3 and extracted with EtOAc (3×20 mL). The combined organic extracts were washed with brine (5 mL), dried (MgSO$_4$), and concentrated in vacuo. The residue was chromatographed (SiO$_2$; 8 g; continuous gradient from 0 to 40% Solvent B over 15 min, hold at 40% Solvent B for 10 min, where Solvent A=Hexanes and Solvent B=EtOAc) to give the desired product (60 mg, 0.27 mmol, 98% yield) as a white solid. $^1$H NMR (500 MHz, CDCl$_3$) δ 7.45-7.41 (m, 2H), 7.14-7.10 (m, 2H), 4.57-4.50 (m, 1H), 3.64-3.56 (m, 1H), 2.51-2.39 (m, 4H).

39C. Trans-2-(3-(4-bromophenyl)cyclobutoxy)acetic acid

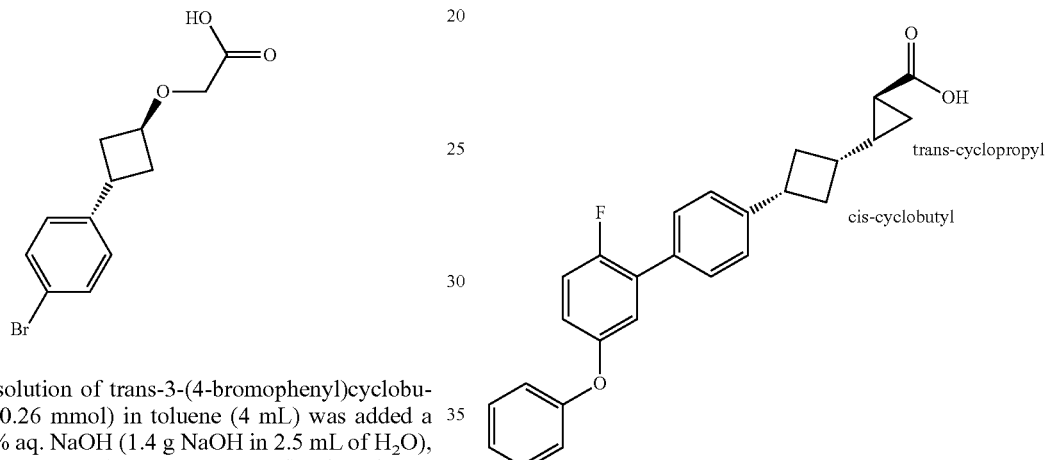

To a 0° C. solution of trans-3-(4-bromophenyl)cyclobutanol (60 mg, 0.26 mmol) in toluene (4 mL) was added a solution of 35% aq. NaOH (1.4 g NaOH in 2.5 mL of H$_2$O), followed by Bu$_4$NHSO$_4$ (44 mg, 0.13 mmol). The mixture was stirred at 0° C. for 30 min, after which tert-butyl 2-bromoacetate (0.08 mL, 0.53 mmol) was added. The reaction mixture was stirred for 14 h at rt, then was acidified with conc HCl and extracted with EtOAc (3×). The combined organic extracts were washed with brine (5 mL), dried (MgSO$_4$) and concentrated in vacuo. The crude residue was purified by Prep. HPLC (PHENOMENEX® Synergi reverse phase ODS-A-5µ 21.2×250 mm column; flow rate=25 mL/min, 10 to 100% Solvent B in A over 30 min, hold to 37 min, where Solvent A=90:10:0.1 H$_2$O:ACN:TFA and Solvent B=90:10:0.1 ACN:H$_2$O:TFA) to give the title compound (45 mg, 0.16 mmol, 60% yield) as a white solid. LCMS, [M+H]$^+$=285.0. $^1$H NMR (400 MHz, CDCl$_3$) δ 7.47-7.41 (m, 2H), 7.13-7.08 (m, 2H), 4.34-4.25 (m, 1H), 4.09 (s, 2H), 3.67-3.55 (m, 1H), 2.61-2.51 (m, 2H), 2.46-2.35 (m, 2H).

Example 39

A mixture of trans-2-(3-(4-bromophenyl)cyclobutoxy) acetic acid (15 mg, 0.05 mmol), (2-fluoro-5-phenoxyphenyl) boronic acid (18 mg, 0.08 mmol), (Ph$_3$P)$_4$Pd (6 mg, 5.26 µmol) and K$_2$CO$_3$ (22 mg, 0.16 mmol) in THF (2 mL) and water (0.7 mL) was heated in a microwave reactor at 130° C. for 20 min under Ar, then was cooled to rt. The reaction was acidified with 1N aq. HCl to pH=2-3, and extracted with EtOAc (4×10 mL). The combined organic extracts were dried (MgSO$_4$) and concentrated in vacuo. The residue was purified by preparative LC/MS using the following conditions: Column: Waters XBridge C18, 19×200 mm, 5-µm particles; Guard Column: Waters XBridge C18, 19×10 mm, 5-µm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5 min hold at 100% B; Flow: 20 mL/min. Fractions containing the desired product were combined and dried via centrifugal evaporation to provide the title compound (12 mg, 0.03 mmol, 54% yield). LCMS, [M–H]$^+$=391.1. $^1$H NMR (500 MHz, DMSO-d$_6$) δ 7.48 (d, J=7.7 Hz, 2H), 7.42-7.30 (m, 5H), 7.17-7.12 (m, 2H), 7.08-7.00 (m, 3H), 4.29-4.21 (m, 1H), 3.92 (s, 2H), 3.61-3.52 (m, 1H), 2.46-2.28 (m, 4H). HPLC-4: RT=1.74 min; HPLC-5: RT=2.26 min; purity=96%.

Example 40

2-(3-(2'-Fluoro-5'-phenoxy-[1,1'-biphenyl]-4-yl) cyclobutyl)cyclopropanecarboxylic acid

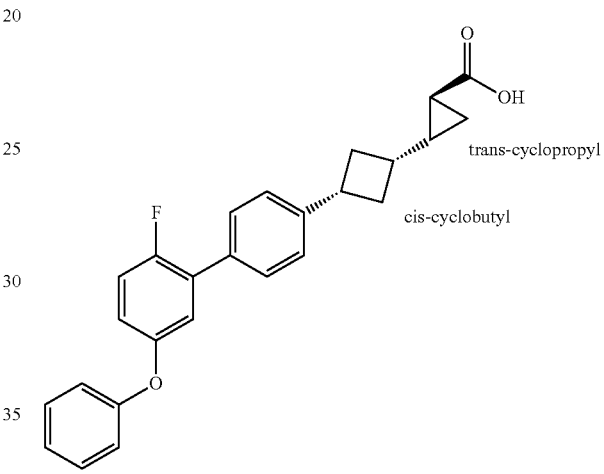

40A. Cis-3-(4-bromophenyl)cyclobutanecarbaldehyde

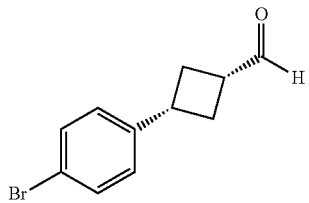 [SMILES: O=C[C@H]1C[C@@H](c2ccc(Br)cc2)C1]

To a solution of diethyl (isocyanomethyl)phosphonate (300 mg, 1.69 mmol) in anhydrous ether (8 mL) at −78° C. under Ar was added dropwise n-BuLi (0.85 mL of a 2.0 M solution in heptane, 1.69 mmol) and the reaction was stirred at −78° C. for 1 h. A solution of 3-(4-bromophenyl)cyclobutanone (318 mg, 1.41 mmol) in anhydrous Et$_2$O (3 mL) was then added dropwise over 10 min. The reaction mixture was then allowed to warm to rt and stirred for 16 h at rt. Conc HCl (2 mL) was added dropwise and the reaction mixture was stirred at rt for 5 h. The mixture was partitioned between EtOAc and water. The layers were separated and the aqueous layer was extracted with EtOAc (3×). The combined organic extracts were washed with brine (10 mL), dried (MgSO$_4$) and concentrated in vacuo to afford the crude product which was chromatographed (SiO$_2$; 40 g; continuous gradient from 0 to 15% Solvent B over 40 min, hold at 15% Solvent B for 10 min, where Solvent A=hexanes and Solvent B=EtOAc) to give the faster eluting trans-isomer, 3-(4-bromophenyl)cyclobutanecarbaldehyde (133 mg, 0.56 mmol, 39% yield) as a white solid and the slower eluting cis-isomer, 3-(4-bromophenyl) cyclobutanecarbaldehyde (80 mg, 0.34 mmol, 24% yield) as a colorless oil. $^1$H NMR (500 MHz, CDCl$_3$) δ 9.73 (d, J=1.9 Hz, 1H), 7.45-7.42 (m, 2H), 7.10-7.07 (m, 2H), 3.53 (quin, J=9.1 Hz, 1H), 3.23 (ttd, J=9.8, 8.1, 2.1 Hz, 1H), 2.62-2.54 (m, 2H), 2.40-2.30 (m, 2H). LCMS, [M+H]$^+$=226.9.

40B. (E)-Methyl-cis-3-(3-(4-bromophenyl)cyclobutyl)acrylate

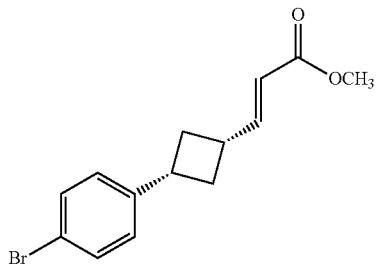 [SMILES: COC(=O)/C=C/[C@H]1C[C@@H](c2ccc(Br)cc2)C1]

A mixture of trimethyl phosphonoacetate (0.07 mL, 0.50 mmol), DBU (0.08 mL, 0.50 mmol) and LiCl (21 mg, 0.50 mmol) in MeCN (2 mL) was stirred at 0° C. under N$_2$ for 30 min, and then cis-3-(4-bromophenyl)cyclobutanecarbaldehyde (80 mg, 0.34 mmol) was added. The reaction was stirred for 2 h at rt (at this point LC-MS showed the starting material had disappeared), then was concentrated in vacuo. The residue was diluted with EtOAc, washed in succession with 1N aq. HCl, sat. aq. NaHCO$_3$, and brine, then dried (MgSO$_4$) and concentrated in vacuo. The residue was chromatographed (SiO$_2$; 12 g; gradient of EtOAc/Hexanes from 0% EtOAc:hex to 20% EtOAc:hex over 25 min) to give the title compound (76 mg, 0.26 mmol, 77% yield) as a colorless oil. LCMS, [M+H]$^+$=295.0. $^1$H NMR (500 MHz, CDCl$_3$) δ 7.44-7.40 (m, 2H), 7.09-7.00 (m, 3H), 5.80 (dd, J=15.7, 1.4 Hz, 1H), 3.74 (s, 3H), 3.47-3.37 (m, 1H), 3.14-3.02 (m, 1H), 2.65-2.57 (m, 2H), 2.08-1.97 (m, 2H).

40C. Methyl 2-(3-(4-bromophenyl)cyclobutyl)cyclopropanecarboxylate

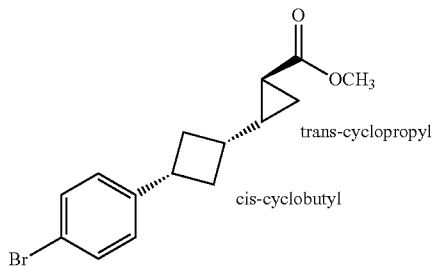 [SMILES: COC(=O)[C@H]1CC1[C@H]1C[C@@H](c2ccc(Br)cc2)C1]

To a vigorously stirred 0° C. (brine plus ice) mixture of Et$_2$O (5 mL) and aq. 40% KOH (2 mL) was added N-methyl-N'-nitro-N-nitrosoguanidine (1.0 g, 6.8 mmol) portionwise over 15 min. After the addition was complete the aq. layer was separated. The ether layer was dried over KOH pellets (twice) at 0° C. for 5 min, then was poured onto a 0° C. solution of (E)-methyl-cis-3-(3-(4-bromophenyl) cyclobutyl)acrylate (70 mg, 0.24 mmol) in THF (2 mL). Pd(OAc)$_2$ (5 mg, 0.02 mmol) was added and the reaction allowed to warm to rt and stirred for 1 h at rt, then was concentrated in vacuo. The residue was chromatographed (SiO$_2$; 12 g; gradient of EtOAc/Hexanes (from 0% EtOAc to 15% EtOAc over 25 min) to give the title compound (68 mg, 0.22 mmol, 92% yield) as a clear oil. LCMS, [M+H]$^+$=309.0. $^1$H NMR (500 MHz, CDCl$_3$) δ 7.43-7.38 (m, 2H), 7.07-7.04 (m, 2H), 3.68 (s, 3H), 3.31-3.19 (m, 1H), 2.48-2.36 (m, 2H), 2.16-2.04 (m, 1H), 1.82-1.70 (m, 2H), 1.53-1.40 (m, 2H), 1.15 (dt, J=9.0, 4.4 Hz, 1H), 0.78 (ddd, J=8.3, 6.5, 4.4 Hz, 1H).

Example 40

A mixture of above methyl 2-(3-(4-bromophenyl)cyclobutyl)cyclopropane carboxylate (15 mg, 0.05 mmol), (2-fluoro-5-phenoxyphenyl)boronic acid (17 mg, 0.07 mmol), (Ph$_3$P)$_4$Pd (6 mg, 4.85 nmol) and K$_2$CO$_3$ (20 mg, 0.15 mmol) in THF (1.2 mL) and water (0.4 mL) was heated in a microwave reactor at 130° C. for 20 min. under Ar, then was cooled to rt. The reaction mixture was acidified with 1N aq. HCl to pH=~2-3, and extracted with EtOAc (4×10 mL). The combined organic extracts were dried (MgSO$_4$), and concentrated in vacuo to afford the crude product. LiOH.H$_2$O (10 mg, 0.25 mmol) was added to a solution of the above crude product in THF (1 mL) and water (0.5 mL). The reaction was stirred at rt overnight, then was partitioned between EtOAc (5 mL) and H$_2$O (10 mL). The aqueous layer was washed with EtOAc (2×5 mL). The combined organic washes were extracted with H$_2$O (3×10 mL). The combined aqueous extracts were acidified with 1N aq. HCl to pH ~3 and extracted with EtOAc (3×10 mL). The combined organic extracts were washed with brine (5 mL), dried (MgSO$_4$) and concentrated in vacuo. The residue was purified by preparative LC/MS with the following conditions: Column: Waters XBridge C18, 19×200 mm, 5 μm particles; Guard Column: Waters XBridge C18, 19×10 mm, 5 μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and dried via centrifugal evaporation to provide the title compound (15 mg, 0.04 mmol, 74% yield). LCMS, [M–H]$^+$=401.2. $^1$H NMR (500 MHz, DMSO-d$_6$) δ 7.48-7.44 (m, 2H), 7.42-7.37 (m, 2H), 7.35-7.29 (m, 3H), 7.16-7.11 (m, 2H), 7.07-7.00 (m, 3H), 3.37-3.23 (m, 1H), 2.41-2.32 (m, 2H), 2.14-2.02 (m, 1H), 1.75 (qd, J=10.3, 6.2 Hz, 2H), 1.39-1.30 (m, 2H), 0.93 (dt, J=8.6, 4.4 Hz, 1H), 0.78-0.70 (m, 1H). HPLC-4: RT=2.28 min; HPLC-5: RT=2.49 min; purity=99%.

Example 41 and Example 42

5-(2'-Fluoro-5'-isopropoxy-[1,1'-biphenyl]-4-yl)spiro[2.3]hexane-1-carboxylic acid

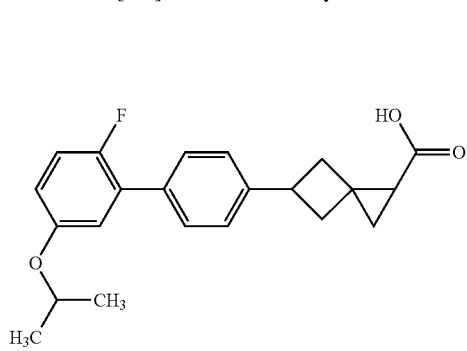

Example 41

Peak 1

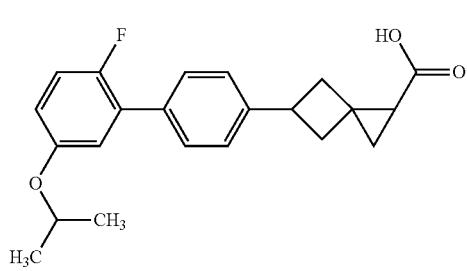

Example 42

Peak 2 a pair of racemic diastereomers

41A. Methyl 2-(3-(4-bromophenyl)cyclobutylidene)acetate

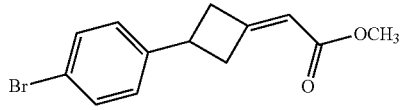 [SMILES: COC(=O)C=C1CC(c2ccc(Br)cc2)C1]

Trimethyl phosphonoacetate (0.144 mL, 1.00 mmol) and DBU (0.151 mL, 1.00 mmol) were added to a suspension of LiCl (42 mg, 1.00 mmol) in MeCN (1.5 mL) at 0° C. under $N_2$. The mixture was stirred at 0° C. for 30 min, then 3-(4-bromophenyl) cyclobutanone (150 mg, 0.666 mmol) was added. The reaction was stirred overnight at rt, then was concentrated in vacuo. The residue was dissolved in EtOAc, then washed in succession with 1N aq. HCl, sat. aq. NaHCO₃, and brine, dried (MgSO₄) and concentrated in vacuo. The crude oil was chromatographed (SiO₂; 24 g; gradient of EtOAc/Hexanes from 0% to 15% over 20 min) to give the title compound (185 mg, 0.659 mmol, 99% yield) as a clear oil. LCMS, $[M+H]^+$=283.0. $^1$H NMR (500 MHz, CDCl₃) δ 7.48-7.43 (m, 2H), 7.16-7.12 (m, 2H), 5.74 (quin, J=2.2 Hz, 1H), 3.72 (s, 3H), 3.69-3.58 (m, 2H), 3.32-3.13 (m, 2H), 2.94 (ddd, J=16.8, 4.1, 2.5 Hz, 1H).

41B. Methyl 2-(3-(2'-fluoro-5'-isopropoxy-[1,1'-biphenyl]-4-yl)cyclobutylidene)acetate

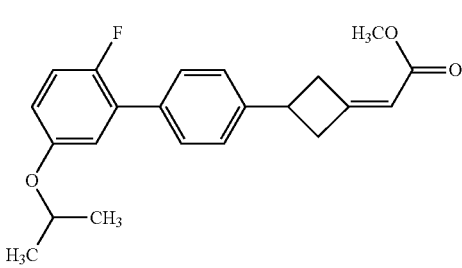 [SMILES: COC(=O)C=C1CC(c2ccc(-c3cc(OC(C)C)ccc3F)cc2)C1]

A mixture of methyl 2-(3-(4-bromophenyl)cyclobutylidene)acetate (53 mg, 0.189 mmol), (2-fluoro-5-isopropoxyphenyl) boronic acid (56 mg, 0.283 mmol), Pd(PPh₃)₄ (22 mg, 0.019 mmol) and K₂CO₃ (78 mg, 0.566 mmol) in THF (3 mL) and water (1 mL) was heated in a microwave reactor at 130° C. for 20 min under Ar, then was cooled to rt. The reaction was acidified with 1N aq. HCl to pH=2-3, and extracted with EtOAc (4×20 mL). The combined organic fractions were dried (MgSO₄) and concentrated in vacuo. The residue was chromatographed (SiO₂; 12 g; continuous gradient from 0 to 20% Solvent B over 30 min, hold at 20% Solvent B for 10 min, where Solvent A=hexanes and Solvent B=EtOAc) to afford the title compound (37 mg, 0.103 mmol, 55% yield) as a colorless oil. LCMS, $[M+H]^+$=355.2.

41C. Methyl 5-(2'-fluoro-5'-isopropoxy-[1,1'-biphenyl]-4-yl)spiro[2.3]hexane-1-carboxylate

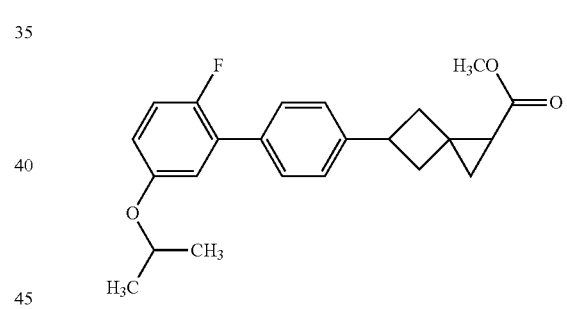

To a 0° C. solution of Et₂O (5 mL) and aq. 40% KOH (2 mL) was added N-methyl-N'-nitro-N-nitrosoguanidine (500 mg, 3.40 mmol) portionwise with vigorous stirring over 15 min at 0° C. The layers were separated; the ether layer was dried twice with KOH pellets at 0° C. for 5 min, then decanted into a 0° C. solution of methyl 2-(3-(2'-fluoro-5'-isopropoxy-[1,1'-biphenyl]-4-yl)cyclobutylidene)acetate (35 mg, 0.099 mmol) THF (2 mL). Pd(OAc)₂ (2 mg, 9.9 umol) was added and the reaction was allowed to warm to rt and stirred for 1 h at rt. The reaction was concentrated in vacuo and the crude product was used in the next step without further purification. LCMS, $[M+NH_3]^+$=386.3.

Example 41 and Example 42

LiOH.H₂O (17 mg, 0.396 mmol) was added to methyl 5-(2'-fluoro-5'-isopropoxy-[1,1'-biphenyl]-4-yl)spiro[2.3]hexane-1-carboxylate (37 mg, 0.099 mmol) in THF (1 mL) and water (0.5 mL) at rt; the reaction was then stirred at rt overnight. The reaction was diluted with EtOAc (5 mL) and H₂O (5 mL). The layers were separated and the aqueous layer was washed with EtOAc (2×2 mL). The combined organic washes were extracted with H₂O (3×5 mL). The combined aqueous extracts were acidified with 1N aq. HCl to pH ~3 and extracted with EtOAc (3×10 mL). The combined organic extracts were washed with brine (5 mL), dried (MgSO₄) and concentrated in vacuo. The residue was purified via preparative LC/MS using the following conditions: Column: Waters XBridge C18, 19×200 mm, 5-μm particles; Guard Column: Waters XBridge C18, 19×10 mm, 5-μm particles; Mobile Phase A: 5:95 MeCN: H₂O with 0.1% TFA; Mobile Phase B: 95:5 MeCN:H₂O with 0.1% TFA; Gradient: 50-90% B over 20 min, then a 5-min hold at 100% B; Flow: 20 mL/min. Fractions containing the desired product were combined and dried via centrifugal evaporation.

Example 41 (6 mg, 0.015 mmol, 15% yield) was the first eluting peak. LCMS, [M−H]⁺=353.1. ¹H NMR (500 MHz, DMSO-d₆) δ 7.48 (d, J=6.9 Hz, 2H), 7.36 (d, J=8.3 Hz, 2H), 7.18 (dd, J=10.2, 9.4 Hz, 1H), 6.97 (dd, J=6.6, 3.0 Hz, 1H), 6.91 (dt, J=8.8, 3.4 Hz, 1H), 4.62 (dt, J=12.1, 6.1 Hz, 1H), 3.68 (quin, J=8.4 Hz, 1H), 2.56-2.42 (m, 2H), 2.38-2.27 (m, 2H), 1.53 (dd, J=7.8, 5.6 Hz, 1H), 1.26 (d, J=5.8 Hz, 6H), 1.11-1.02 (m, 2H). HPLC-4: RT=2.05 min, purity=97%; HPLC-5: RT=2.22 min, purity=97%.

Example 42 (4 mg, 0.012 mmol, 12% yield) was the second eluting peak. LCMS, [M−H]⁺=353.3. ¹H NMR (400 MHz, CDCl₃) δ 7.51 (dd, J=8.4, 1.5 Hz, 2H), 7.37 (d, J=8.1 Hz, 2H), 7.05 (dd, J=9.9, 9.0 Hz, 1H), 6.95 (dd, J=6.4, 3.1 Hz, 1H), 6.81 (dt, J=8.9, 3.4 Hz, 1H), 4.50 (dt, J=12.1, 6.1 Hz, 1H), 3.73 (quin, J=8.4 Hz, 1H), 2.74 (t, J=10.6 Hz, 1H), 2.61 (t, J=10.3 Hz, 1H), 2.52-2.39 (m, 2H), 1.76 (dd, J=8.3, 5.4 Hz, 1H), 1.37-1.32 (m, 6H), 1.31-1.24 (m, 1H), 1.15 (dd, J=8.4, 4.8 Hz, 1H). Example 41 and Example 42 are a pair of racemic diastereomers.

Example 43

2-(3-(2'-Fluoro-5'-isopropoxy-[1,1'-biphenyl]-4-yl) cyclobutyl)acetic acid

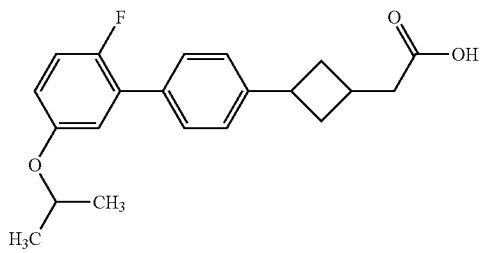

a mixture of cis- and trans-isomers

43A. Methyl 2-(3-(2'-fluoro-5'-isopropoxy-[1,1'-biphenyl]-4-yl)cyclobutyl)acetate

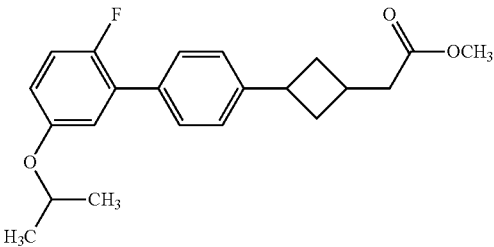 [SMILES: COC(=O)CC1CC(c2ccc(-c3cc(OC(C)C)ccc3F)cc2)C1]

A solution of methyl 2-(3-(2'-fluoro-5'-isopropoxy-[1,1'-biphenyl]-4-yl)cyclobutylidene)acetate (75 mg, 0.21 mmol) in MeOH (5 mL) was evacuated and flushed with Ar. 10% Pd/C (10 mg, 0.02 mmol) was added and the mixture was placed under an atmosphere of H₂ and stirred at rt overnight. The catalyst was filtered off and washed with EtOAc. The combined filtrates were concentrated in vacuo to give the title compound as a colorless oil which was used in the next step without further purification.

Example 43

LiOH.H₂O (36 mg, 0.85 mmol) was added to a solution of methyl 2-(3-(2'-fluoro-5'-isopropoxy-[1,1'-biphenyl]-4-yl)cyclobutyl)acetate (76 mg, 0.21 mmol) in THF (1.4 mL) and water (0.7 mL) at rt. The reaction was stirred at rt overnight, then was partitioned between EtOAc (5 mL) and H₂O (5 mL). The aqueous layer was washed with EtOAc (2×5 mL). The organic layer was extracted with H₂O (3×5 mL). The combined aqueous extracts were acidified with 1N aq. HCl to pH ~3, then extracted with EtOAc (3×10 mL). The combined organic extracts were washed with brine (5 mL), dried (MgSO₄) and concentrated in vacuo. The residue was purified by preparative LC/MS using the following conditions: Column: Waters XBridge C18, 19×200 mm, 5 μm particles; Guard Column: Waters XBridge C18, 19×10 mm, 5 μm particles; Mobile Phase A: 5:95 MeCN:H₂O with 0.1% TFA; Mobile Phase B: 95:5 MeCN:H₂O with 0.1% TFA; Gradient: 50-90% B over 20 min, then a 5-min hold at 100% B; Flow: 20 mL/min. Fractions containing the desired product were combined and dried via centrifugal evaporation to provide the title compound (65 mg, 90% yield). LCMS, [M−H]⁺=341.2. ¹H NMR (500 MHz, DMSO-d₆) δ 7.49-7.43 (m, 2H), 7.36-7.29 (m, 2H), 7.21-7.16 (m, 1H), 6.98-6.88 (m, 2H), 4.66-4.58 (m, 1H), 3.42-3.31 (m, 1H), 2.65-2.52 (m, 1H), 2.49-2.43 (m, 2H), 2.33-2.22 (m, 2H), 2.15-2.07 (m, 1H), 1.83-1.74 (m, 1H), 1.28-1.24 (m, 6H). HPLC-4: RT=1.87 min; HPLC-5: RT=2.21 min; purity=100%.

Example 44

2-(Trans-3-(2'-fluoro-5'-isopropoxy-[1,1'-biphenyl]-4-yl)cyclobutyl)acetic acid and

Example 45

2-(Cis-3-(2'-fluoro-5'-isopropoxy-[1,1'-biphenyl]-4-yl)cyclobutyl)acetic acid

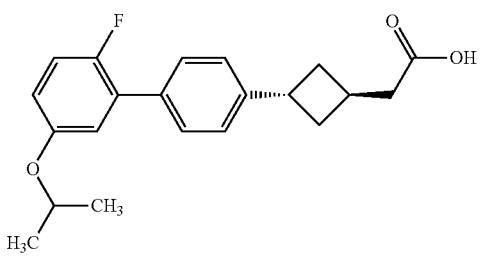

Example 44

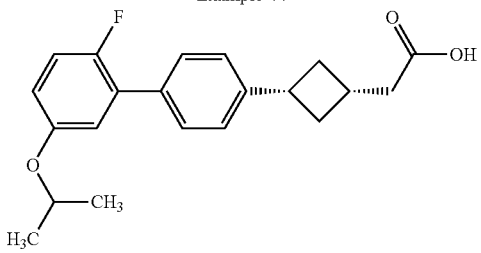

Example 45

A sample of 2-(3-(2'-fluoro-5'-isopropoxy-[1,1'-biphenyl]-4-yl)cyclobutyl) acetic acid (65 mg, 0.190 mmol) were separated by chiral HPLC chromatography (Instrument: Berger Multigram II SFC; Column: CHIRALCEL® OJ-H, 21×250 mm, 5μ; Mobile Phase: 15% EtOH/85% CO$_2$; Flow Conditions: 45 mL/min, 100 Bar, 40° C.; Detector Wavelength: 249 nm; Injection Details: 0.5 mL of 13 mg/mL in MeCN-MeOH). Example 44, the trans-isomer (first eluting peak, 15 mg, 0.044 mmol, 23% yield) was obtained: LCMS, [M−H]$^+$=341.3. $^1$H NMR (500 MHz, CDCl$_3$) δ 7.50 (d, J=6.9 Hz, 2H), 7.33 (d, J=8.3 Hz, 2H), 7.05 (t, J=9.5 Hz, 1H), 6.95 (dd, J=6.6, 3.0 Hz, 1H), 6.81 (dt, J=8.8, 3.4 Hz, 1H), 4.55-4.46 (m, 1H), 3.68 (quin, J=8.3 Hz, 1H), 2.83-2.67 (m, 3H), 2.50-2.41 (m, 2H), 2.29-2.20 (m, 2H), 1.35 (d, J=6.1 Hz, 6H). HPLC-1: Rt=12.02 min, purity=98%; HPLC-2: Rt=9.96 min, purity=97%. Example 45, the cis-isomer (second eluting peak, 33 mg, 0.092 mmol, 48% yield) was obtained: LCMS, [M−H]$^+$=341.3. $^1$H NMR (500 MHz, CDCl$_3$) δ 7.48 (d, J=6.6 Hz, 2H), 7.30-7.23 (m, 2H), 7.04 (t, J=9.5 Hz, 1H), 6.94 (dd, J=6.3, 3.0 Hz, 1H), 6.81 (dt, J=8.9, 3.5 Hz, 1H), 4.50 (spt, J=6.1 Hz, 1H), 3.52-3.40 (m, 1H), 2.76-2.60 (m, 3H), 2.52 (d, J=7.2 Hz, 2H), 1.95-1.85 (m, 2H), 1.35 (s, 6H). HPLC-1: Rt=12.02 min, purity=100%; HPLC-2: RT=9.96 min, purity=100%.

Example 46

Cis-3-(3-(2'-fluoro-5'-isopropoxy-[1,1'-biphenyl]-4-yl)cyclobutyl)propanoic acid

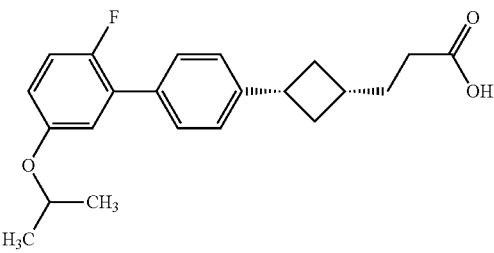 [SMILES: CC(C)Oc1ccc(F)c(-c2ccc([C@H]3C[C@@H](CCC(=O)O)C3)cc2)c1]

46A. Cis-1-diazo-3-(3-(2'-fluoro-5'-isopropoxy-[1,1'-biphenyl]-4-yl)cyclobutyl)propan-2-one

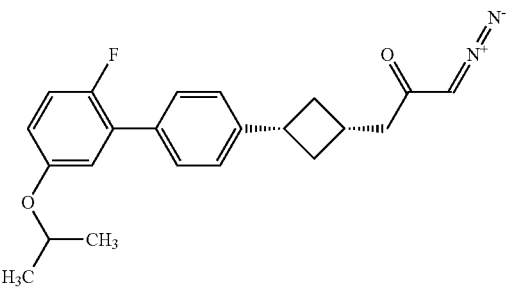 [SMILES: CC(C)Oc1ccc(F)c(-c2ccc([C@H]3C[C@@H](CC(=O)C=[N+]=[N-])C3)cc2)c1]

To a 0° C. solution of cis-2-(3-(2'-fluoro-5'-isopropoxy-[1,1'-biphenyl]-4-yl)cyclobutyl)acetic acid (15 mg, 0.04 mmol) in CH$_2$Cl$_2$ (1 mL) was added oxalyl chloride (0.07 mL, 0.13 mmol), followed by 1 drop of DMF. After stirring for 10 min at 0° C., the mixture was allowed to warm to rt and stirring was continued at rt for 1 h (reaction complete at this point by LC/MS). Volatiles were removed in vacuo and the residue was azeotroped with toluene to give the crude acid chloride product, which was dissolved in THF (0.5 mL)/MeCN (0.5 mL). To this 0° C. solution was added Me$_3$SiCHN$_2$ (0.11 mL of a 2.0 M solution in Et$_2$O; 0.22 mmol), and the resulting mixture was allowed to warm up to rt slowly and stirring was continued at rt overnight. Volatiles were removed in vacuo to afford a light yellow oil, which was chromatographed (SiO$_2$; 4 g; gradient from 0 to 30% Solvent B over 15 min, hold at 30% Solvent B for 10 min, where Solvent A=hexanes and Solvent B=EtOAc) to give the title compound (6 mg, 0.02 mmol, 37% yield) as a white solid. LCMS, [M+Na]$^+$=389.2.

Example 46

To a solution of cis-1-diazo-3-(3-(2'-fluoro-5'-isopropoxy-[1,1'-biphenyl]-4-yl)cyclobutyl) propan-2-one (6 mg, 0.02 mmol) in THF (0.6 mL) and water (0.3 mL) was added AgNO$_3$ (3 mg, 0.02 mmol). The yellow/green solution was stirred overnight, then was concentrated in vacuo to remove the THF. The resulting slurry was partitioned between H$_2$O and CH$_2$Cl$_2$. The aqueous layer was extracted with CH$_2$Cl$_2$ (5×10 mL). The combined organic extracts were washed with brine (5 mL), dried (MgSO$_4$) and concentrated in vacuo. The residue was purified by preparative LC/MS using the following conditions: Column: Waters XBridge C18, 19×200 mm, 5-μm particles; Guard Column: Waters XBridge C18, 19×10 mm, 5-μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and dried via centrifugal evaporation to provide the desired product (4 mg, 10.89 μmol, 67% yield). LCMS, [M−H]$^+$=355.2. $^1$H NMR (500M Hz, DMSO-d$_6$) δ 7.46 (d, J=7.2 Hz, 2H), 7.30 (d, J=7.4 Hz, 2H), 7.18 (t, J=9.6 Hz, 1H), 6.99-6.87 (m, 2H), 4.67-4.57 (m, 1H), 2.47-2.39 (m, 3H), 2.27-2.10 (m, 3H), 1.73-1.58 (m, 4H), 1.26 (d, J=5.8 Hz, 6H). HPLC-4: RT=2.08 min; HPLC-5: RT=2.34 min; purity=97%.

Example 47

3-((2'-Fluoro-5'-isopropoxy-[1,1'-biphenyl]-4-yl) methylene)cyclobutanecarboxylic acid

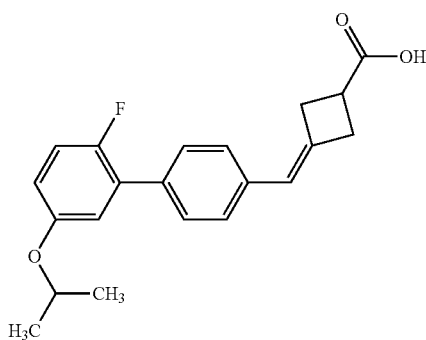 [SMILES: CC(C)Oc1ccc(F)c(-c2ccc(C=C3CC(C(=O)O)C3)cc2)c1]

47A. Methyl 3-oxocyclobutanecarboxylate

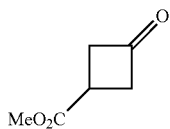

To a mixture of 3-oxocyclobutanecarboxylic acid (2.5 g, 21.9 mmol), EDC (6.3 g, 32.9 mmol) and DMAP (0.27 g, 2.19 mmol) in DCM (100 mL) was added MeOH (0.98 mL, 24.1 mmol). The mixture was stirred at rt overnight, then was concentrated in vacuo to give a crude oil, which was chromatographed (SiO$_2$; 80 g; continuous gradient from 0 to 25% Solvent B over 30 min, hold at 25% Solvent B for 10 min, where Solvent A=Hexanes and Solvent B=10% EtOAc) to give the title compound (2.41 g, 18.81 mmol, 86% yield) as a colorless oil. $^1$H NMR (500 MHz, CDCl$_3$) δ 3.77 (s, 3H), 3.47-3.40 (m, 2H), 3.34-3.21 (m, 3H).

47B. Methyl 3-(4-bromobenzylidene)cyclobutanecarboxylate

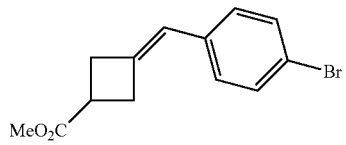

Potassium tert-butoxide (3.90 mL of a 1.0 M solution in THF; 3.90 mmol) was added dropwise to a solution of (4-bromobenzyl)triphenylphosphonium bromide (2.10 g, 4.10 mmol) in toluene (10 mL). After stirring at 25° C. for 0.5 h, this ylide solution was cooled to 0° C., and a solution of methyl 3-oxocyclobutanecarboxylate (0.5 g, 3.90 mmol) in toluene (2 mL) was added rapidly. The mixture was heated at reflux for 24 h, then cooled to rt and partitioned between water (25 mL) and EtOAc (200 mL). The aqueous layer was extracted with EtOAc (20 mL). The combined organic extracts were washed with water (2×20 mL), brine (20 mL), dried (MgSO$_4$) and concentrated in vacuo. This residue was chromatographed (SiO$_2$; 80 g; EtOAc/hexanes—from 0% EtOAc to 20% EtOAc over 25 min) to afford the title compound (562 mg, 2.00 mmol, 51% yield) as a beige oil. LCMS, [M+H]$^+$=281.1. $^1$H NMR (500 MHz, CDCl$_3$) δ 7.44-7.41 (m, 2H), 7.07-7.04 (m, 2H), 6.13-6.10 (m, 1H), 3.74 (s, 3H), 3.38-3.14 (m, 4H), 3.12-3.04 (m, 1H).

47C. Methyl 3-((2'-fluoro-5'-isopropoxy-[1,1'-biphenyl]-4-yl)methylene) cyclobutanecarboxylate

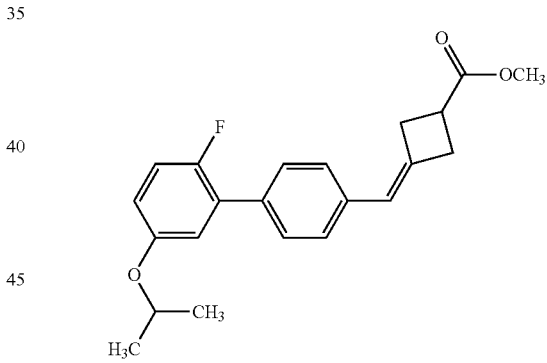

A mixture of methyl 3-(4-bromobenzylidene)cyclobutanecarboxylate (100 mg, 0.36 mmol), (2-fluoro-5-isopropoxyphenyl)boronic acid (106 mg, 0.53 mmol), (Ph$_3$P)$_4$Pd (41 mg, 0.04 mmol) and K$_2$CO$_3$ (147 mg, 1.07 mmol) in THF (6 mL) and water (2 mL) was heated in a microwave reactor at 130° C. for 20 min. under Ar, then was cooled to rt. Water (5 mL) was added and the mixture was extracted with EtOAc (4×10 mL). The combined organic extracts were dried (MgSO$_4$) and concentrated in vacuo. This residue was chromatographed (SiO$_2$; 12 g; EtOAc/hexanes—from 0% EtOAc to 15% EtOAc over 20 min) to give the title compound (87 mg, 0.24 mmol, 69% yield) as a colorless oil. LCMS, [M+H]$^+$=355.1.

Example 47

LiOH.H$_2$O (5 mg, 0.11 mmol) was added to a solution of methyl 3-((2'-fluoro-5'-isopropoxy-[1,1'-biphenyl]-4-yl)

methylene)cyclobutanecarboxylate (10 mg, 0.03 mmol) in THF (1 mL) and water (0.5 mL) at rt. The reaction was stirred at rt overnight, then was partitioned between EtOAc (5 mL) and H$_2$O (5 mL). The aqueous layer was washed with EtOAc (2×5 mL). The combined organic extracts were extracted with H$_2$O (3×5 mL). The combined aqueous extracts were acidified with 1N aq. HCl to pH ~3 and extracted with EtOAc (3×10 mL). The combined organic extracts were washed with brine (5 mL), dried (MgSO$_4$) and concentrated in vacuo. The residue was purified by preparative LC/MS using the following conditions: Column: Waters XBridge C18, 19×200 mm, 5 μm particles; Guard Column: Waters XBridge C18, 19×10 mm, 5 μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5 min hold at 100% B; Flow: 20 mL/min. Fractions containing the desired product were combined and dried via centrifugal evaporation to provide the title compound (6 mg, 0.02 mmol, 65% yield). LCMS, [M–H]$^+$=339.1. $^1$H NMR (500 MHz, DMSO-d$_6$) δ 7.50 (dd, J=8.3, 1.7 Hz, 2H), 7.30 (d, J=8.3 Hz, 2H), 7.19 (dd, J=10.3, 8.9 Hz, 1H), 7.00-6.97 (m, 1H), 6.91 (dt, J=8.8, 3.4 Hz, 1H), 6.23-6.20 (m, 1H), 4.66-4.58 (m, 1H), 3.26-3.20 (m, 3H), 3.10-2.98 (m, 2H), 1.26 (d, J=5.8 Hz, 6H). HPLC-4: RT=1.70 min; HPLC-5: RT=2.13 min; purity=98%.

Examples 48 and 49

3-((2'-Fluoro-5'-isopropoxy-[1,1'-biphenyl]-4-yl)methyl)cyclobutanecarboxylic acid Example 48

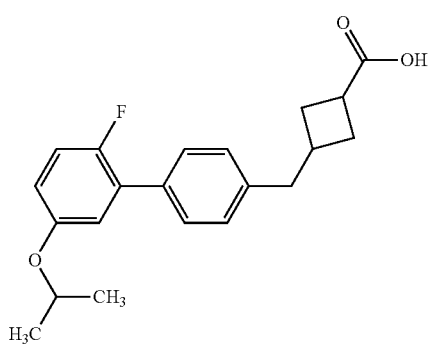

First eluting isomer

Example 49

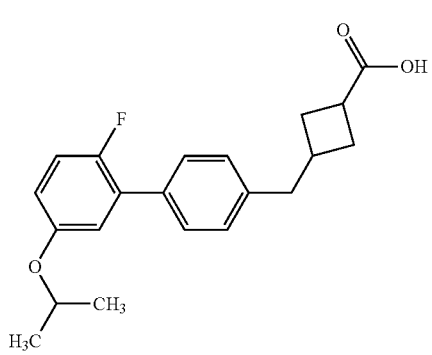

Second eluting isomer

A solution of methyl 3-((2'-fluoro-5'-isopropoxy-[1,1'-biphenyl]-4-yl)methylene)cyclobutanecarboxylate (75 mg, 0.21 mmol) in MeOH (5 mL) was evacuated and flushed with Ar. 10% Pd/C (10 mg, 0.02 mmol) was added. The mixture was evacuated, filled with an atmosphere of H$_2$ and the reaction was stirred overnight at rt. The catalyst was filtered off and washed with EtOAc. The combined filtrates were concentrated in vacuo to give the crude ester product as a colorless oil. LiOH.H$_2$O (36 mg, 0.85 mmol) was added to a solution of the crude ester in THF (2 mL) and water (1 mL) at rt. The reaction was then stirred at rt overnight, then was partitioned between EtOAc (5 mL) and H$_2$O (5 mL). The aqueous layer was washed with EtOAc (2×5 mL). The organic layer was extracted with H$_2$O (3×5 mL). The combined aqueous layers were acidified with 1N aq. HCl to pH ~3 and extracted with EtOAc (3×10 mL). The combined organic extracts were washed with brine (5 mL), dried (MgSO$_4$) and concentrated in vacuo. The residue was purified by preparative LC/MS using the following conditions: Column: Waters XBridge C18, 19×200 mm, 5 μm particles; Guard Column: Waters XBridge C18, 19×10 mm, 5 μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5 min hold at 100% B; Flow: 20 mL/min. Fractions containing the desired product were combined and dried via centrifugal evaporation. Example 48, the first eluting peak (7.8 mg, 0.023 mmol, 39% yield) was obtained. LCMS, [M–H]$^+$=341.2. $^1$H NMR (500 MHz, DMSO-d$_6$) δ 7.44 (dd, J=8.1, 1.5 Hz, 2H), 7.24 (d, J=8.3 Hz, 2H), 7.18 (dd, J=10.5, 9.1 Hz, 1H), 6.96 (dd, J=6.5, 3.2 Hz, 1H), 6.90 (dt, J=8.9, 3.5 Hz, 1H), 4.66-4.57 (m, 1H), 2.84 (quin, J=8.9 Hz, 1H), 2.68 (d, J=7.7 Hz, 2H), 2.47-2.38 (m, 1H), 2.18 (qd, J=8.5, 2.3 Hz, 2H), 1.91-1.81 (m, 2H), 1.27 (s, 6H). HPLC-4: RT=1.86 min; HPLC-5: RT=2.18 min; purity=100%. Example 49, the second eluting peak (1.5 mg, 0.004 mmol, 8% yield) was obtained. LCMS, [M–H]$^+$=341.2. $^1$H NMR (500 MHz, DMSO-d$_6$) δ 7.45 (dd, J=8.0, 1.7 Hz, 2H), 7.27 (d, J=8.3 Hz, 2H), 7.18 (dd, J=10.3, 8.9 Hz, 1H), 6.97 (dd, J=6.5, 3.2 Hz, 1H), 6.90 (dt, J=8.9, 3.5 Hz, 1H), 4.66-4.59 (m, 1H), 3.05-2.96 (m, 1H), 2.76 (d, J=7.7 Hz, 2H), 2.59-2.52 (m, 1H), 2.21 (ddd, J=12.0, 8.3, 6.1 Hz, 2H), 1.91 (ddd, J=11.8, 9.4, 6.1 Hz, 2H), 1.27 (s, 6H). HPLC-4: RT=1.87 min; HPLC-5: RT=2.19 min; purity=100%.

Example 50

2-(3-((2'-Fluoro-5'-isopropoxy-[1,1'-biphenyl]-4-yl)methyl)cyclobutyl)acetic acid

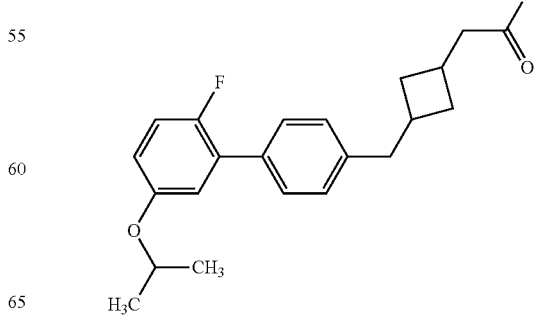

50A. 2-Diazo-1-(3-((2'-fluoro-5'-isopropoxy-[1,1'-biphenyl]-4-yl)methyl)cyclobutyl) ethanone

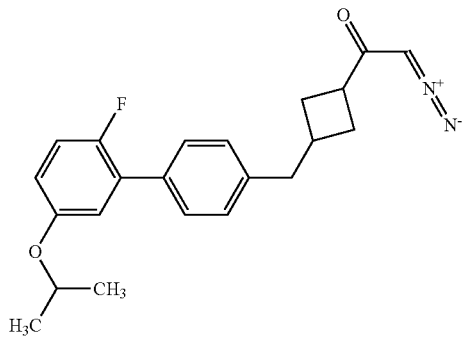 [SMILES: CC(C)Oc1ccc(F)c(-c2ccc(CC3CC(C(=O)C=[N+]=[N-])C3)cc2)c1]

To a 0° C. solution of 3-((2'-fluoro-5'-isopropoxy-[1,1'-biphenyl]-4-yl)methyl) cyclobutane carboxylic acid (50 mg, 0.15 mmol) in $CH_2Cl_2$ (2 mL) was added oxalyl chloride (0.22 mL of a 2.0 M solution in $CH_2Cl_2$; 0.44 mmol), followed by 1 drop of DMF. The mixture was stirred for 10 min at 0° C., then was warmed to rt and stirring was continued at rt for 1 h. Volatiles were removed in vacuo and the residue was azeotroped with toluene to give the crude acid chloride, which was dissolved in THF (2 mL) and MeCN (2 mL). $Me_3SiCHN_2$ (0.37 mL of a 2.0 M solution in $Et_2O$; 0.73 mmol) was added at 0° C., and the resulting mixture was allowed to warm to rt slowly and stirring was continued at rt overnight. The reaction mixture was concentrated in vacuo to afford a light yellow oil, which was chromatographed ($SiO_2$; 12 g; gradient from 0 to 25% Solvent B over 20 min, hold at 25% Solvent B for 10 min, where Solvent A=hexanes and Solvent B=EtOAc) to give the title compound (34 mg, 0.09 mmol, 63% yield) as a colorless oil. LCMS, $[M+H]^+=367.2$.

Example 50

To a solution of 2-diazo-1-(3-((2'-fluoro-5'-isopropoxy-[1,1'-biphenyl]-4-yl)methyl)cyclobutyl)ethanone (33 mg, 0.09 mmol) in THF (2.6 mL) and water (1.2 mL) was added $AgNO_3$ (16 mg, 0.10 mmol). The yellow/green solution was stirred overnight at RT, then was diluted with EtOAc. The organic layer was washed with brine (10 mL), dried ($MgSO_4$) and concentrated in vacuo. The residue was purified by preparative LC/MS using the following conditions: Column: Waters XBridge C18, 19×200 mm, 5-μm particles; Guard Column: Waters XBridge C18, 19×10 mm, 5 μm particles; Mobile Phase A: 5:95 MeCN:$H_2O$ with 0.1% TFA; Mobile Phase B: 95:5 MeCN:$H_2O$ with 0.1% TFA; Gradient: 50-90% B over 20 min, then a 5 min hold at 100% B; Flow: 20 mL/min. Fractions containing the desired product were combined and dried via centrifugal evaporation to provide the title compound (24 mg, 0.07 mmol, 75% yield). LCMS, [M−H]=355.1.

Example 51

2-(Cis-3-((2'-fluoro-5'-isopropoxy-[1,1'-biphenyl]-4-yl)methyl)cyclobutyl)acetic acid and

Example 52

2-(Trans-3-((2'-fluoro-5'-isopropoxy-[1,1'-biphenyl]-4-yl)methyl)cyclobutyl)acetic acid

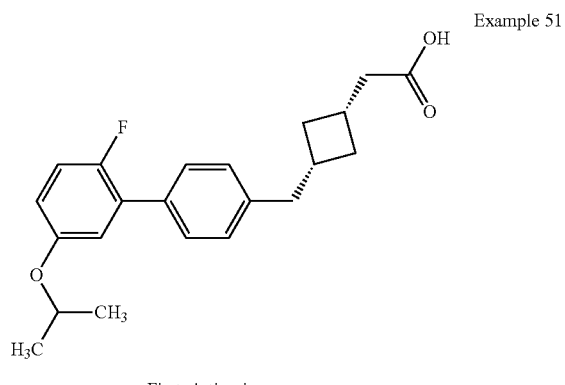

First eluting isomer

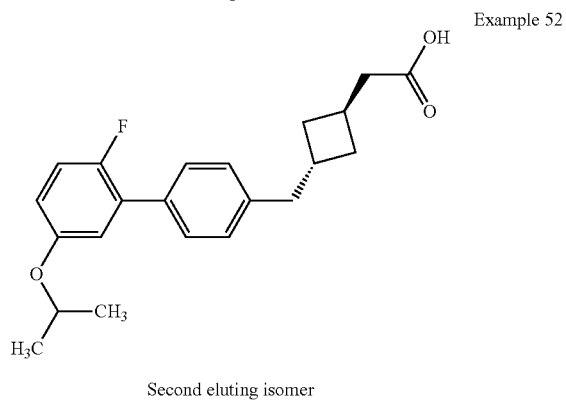

Second eluting isomer

A sample of 2-(3-((2'-fluoro-5'-isopropoxy-[1,1'-biphenyl]-4-yl)methyl) cyclobutyl)acetic acid (17 mg, 0.048 mmol) were separated by chiral HPLC chromatography (Instrument: Berger Multigram II SFC; Column: CHIRALPAK® ID, 30×250 mm, 5μ; Mobile Phase: 10% EtOH/90% $CO_2$; Flow Conditions: 85 mL/min, 100 Bar, 40° C.; Detector Wavelength: 247 nm; Injection Details: 0.5 mL of 4 mg/mL in MeCN). Example 51 (cis-isomer), the first eluting peak (11.4 mg, 0.032 mmol, 67% yield) was obtained. LCMS, $[M–H]^+=355.2$. $^1H$ NMR (500 MHz, $CDCl_3$) δ 7.44 (dd, J=8.1, 1.5 Hz, 2H), 7.19 (d, J=8.3 Hz, 2H), 7.03 (dd, J=10.0, 8.9 Hz, 1H), 6.94 (dd, J=6.5, 3.2 Hz, 1H), 6.80 (dt, J=8.9, 3.5 Hz, 1H), 4.50 (spt, J=6.1 Hz, 1H), 2.71 (d, J=7.4 Hz, 2H), 2.55-2.40 (m, 4H), 2.36-2.27 (m, 2H), 1.52-1.43 (m, 2H), 1.34 (d, J=6.1 Hz, 6H). HPLC-4: RT=1.95 min; HPLC-5: RT=2.10 min; purity=100%. Example 52 (trans-isomer), the second eluting peak (3.8 mg, 10.66 nmol, 22% yield) was obtained. LCMS, $[M–H]^+=355.2$. $^1H$ NMR (500 MHz, $CDCl_3$) δ 7.47-7.43 (m, 2H), 7.21 (d, J=8.0 Hz, 2H), 7.06-7.01 (m, 1H), 6.94 (dd, J=6.5, 3.2 Hz, 1H), 6.80 (dt, J=8.8, 3.4 Hz, 1H), 4.50 (dt, J=12.1, 6.1 Hz, 1H), 2.81 (d, J=7.7 Hz, 2H), 2.77-2.59 (m, 2H), 2.53 (d, J=7.7 Hz, 2H),

Example 53

4-(Cis-3-(3-phenoxybenzyloxy)cyclobutyl)butanoic acid

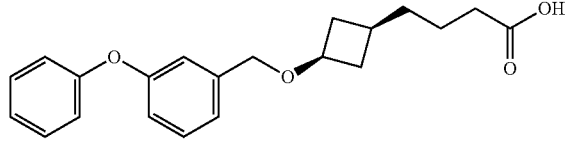 [SMILES: O=C(O)CCC[C@H]1C[C@@H](OCc2cccc(Oc3ccccc3)c2)C1]

53A. Ethyl 3-oxocyclobutanecarboxylate

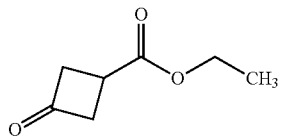

To a −78° C. solution of 3-oxocyclobutanecarboxylic acid (2.0 g, 17.5 mmol) in EtOH (20 mL) was bubbled HCl gas for 3 min. The solution was then warmed to rt and stirred at rt for 18 h. Volatiles were concentrated in vacuo and the residue was chromatographed (SiO$_2$; 10% EtOAc:hexanes) to afford the title compound (2.15 g, 82% yield) as a clear oil. $^1$H NMR (400 MHz, CDCl$_3$) δ 4.23 (q, J=7.1 Hz, 2H), 3.38-3.47 (m, 2H), 3.18-3.34 (m, 3H), 1.30 (t, J=7.2 Hz, 3H).

53B. Ethyl 3-hydroxycyclobutanecarboxylate

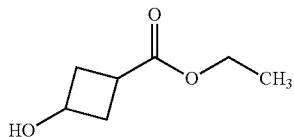

To a 0° C. solution of ethyl 3-oxocyclobutanecarboxylate (0.18 g, 1.27 mmol) in MeOH (10 mL) was added NaBH$_4$ (0.048 g, 1.27 mmol). The solution was stirred at 0° C. for 30 min and then quenched with 1 N aq. HCl. Volatiles were removed in vacuo, and the residue was partitioned between EtOAc and 1 N aq. HCl. The organic layer was dried (MgSO$_4$) and concentrated in vacuo to afford the title compound (0.17 g, 93% yield) as a mixture of the cis- and trans-isomers. $^1$H NMR (500 MHz, CDCl$_3$) δ 4.17-4.24 (m, 1H), 4.15 (d, J=7.2 Hz, 2H), 2.54-2.66 (m, 3H), 2.11-2.22 (m, 2H), 1.27 (t, J=7.2 Hz, 3H).

53C. Cis-ethyl 3-(3-phenoxybenzyloxy)cyclobutanecarboxylate

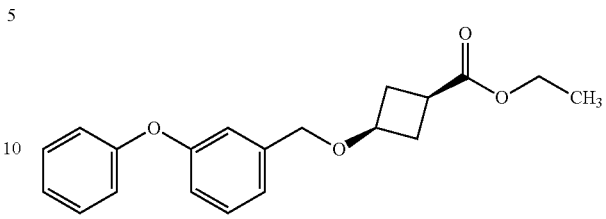

To a 0° C. solution of ethyl 3-hydroxycyclobutanecarboxylate (0.12 g, 0.83 mmol) in 5 mL of DCM at was added AgOTf (0.321 g, 1.25 mmol) and 2,6-di-tert-butylpyridine (0.318 g, 1.67 mmol). The solution was stirred for at 0° C. for 10 min, after which 1-(chloromethyl)-3-phenoxybenzene (0.273 g, 1.25 mmol) was added. The mixture was stirred at 0° C. for 30 min, then was allowed to slowly warm to rt and stirred at rt for 18 h. The mixture was diluted with DCM and washed with sat'd aq. NaHCO$_3$. The organic layer was dried (MgSO$_4$) and concentrated in vacuo to give a mixture of cis and trans-isomers. The residue was purified by flash chromatography (20% EtOAc:hexanes) to afford the title compound (0.21 g, 70% yield; cis-isomer (clear oil) as the faster moving isomer on an SiO$_2$ column. $^1$H NMR (500 MHz, CDCl$_3$) δ 7.28-7.37 (m, 3H), 7.06-7.14 (m, 2H), 6.98-7.04 (m, 3H), 6.90-6.95 (m, 1H), 4.41 (s, 2H), 4.14 (q, J=7.0 Hz, 2H), 3.91-3.99 (m, 1H), 2.57-2.64 (m, 1H), 2.45-2.52 (m, 2H), 2.21-2.29 (m, 2H), 1.26 (t, J=7.0 Hz, 3H).

53D. (Cis-3-(3-phenoxybenzyloxy)cyclobutyl)methanol

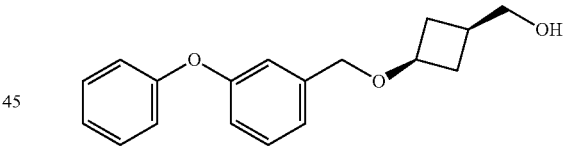

To a 0° C. solution of cis-ethyl 3-(3-phenoxybenzyloxy) cyclobutanecarboxylate (0.18 g, 0.55 mmol) in DCM (10 mL) was added DIBAL-H (1.21 mL of a 1 M solution in toluene, 1.21 mmol). The solution was stirred at 0° C. for 1 h and then quenched with 1 N aq. NaOH. The organic layer was separated. The aqueous layer was extracted with DCM. The combined organic extracts were dried (MgSO$_4$) and concentrated in vacuo. The residue was chromatographed (SiO$_2$; 20% EtOAc:hexanes) to afford the title compound (85 mg, 52% yield) as an oil. $^1$H NMR (500 MHz, CDCl$_3$) δ 7.28-7.37 (m, 3H), 7.06-7.14 (m, 2H), 6.99-7.04 (m, 3H), 6.91-6.95 (m, 1H), 4.40 (s, 2H), 3.91-3.99 (m, 1H), 3.62 (d, J=6.3 Hz, 2H), 2.32-2.39 (m, 2H), 2.01-2.09 (m, 1H), 1.69-1.77 (m, 2H).

---

2.06-1.97 (m, 2H), 1.93-1.84 (m, 2H), 1.34 (d, J=6.1 Hz, 6H). HPLC-4: RT=1.95 min; HPLC-5: RT=2.09 min; purity=100%.

53E. 1-((Cis-3-(iodomethyl)cyclobutoxy)methyl)-3-phenoxybenzene

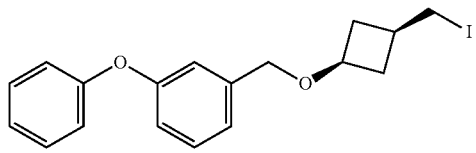 [SMILES: IC[C@H]1C[C@@H](OCc2cccc(Oc3ccccc3)c2)C1]

To a solution of iodine (107 mg, 0.42 mmol) and Ph₃P (111 mg, 0.42 mmol) in DCM (10 mL) was added imidazole (35 mg, 0.51 mmol). The mixture was stirred at rt for 10 min, after which (cis-3-(3-phenoxybenzyloxy)cyclobutyl)methanol (80 mg, 0.28 mmol) in DCM (1 mL) was added dropwise. The mixture was stirred at rt for 1 h and then quenched with 10% aq. Na₂SO₃ (20 mL). The organic layer was separated. The aqueous layer was extracted with DCM. The combined organic extracts were dried (MgSO₄) and concentrated in vacuo. The residue was chromatographed (SiO₂; 10% EtOAc:hexanes) to afford the title compound (80 mg, 72% yield) as a pale yellow oil. ¹H NMR (500 MHz, CD₂Cl₂) δ 7.18-7.27 (m, 3H), 7.00-7.04 (m, 1H), 6.97 (dd, J=7.6, 0.7 Hz, 1H), 6.88-6.92 (m, 3H), 6.82 (dt, J=8.3, 1.2 Hz, 1H), 4.27 (s, 2H), 3.68-3.77 (m, 1H), 3.14 (d, J=7.4 Hz, 2H), 2.25-2.34 (m, 2H), 2.01-2.10 (m, 1H), 1.41-1.50 (m, 2H).

Example 53

A mixture of zinc (53 mg, 0.81 mmol) and methyl acrylate (70 mg, 0.81 mmol)) in pyridine (5 mL) was warmed to 50° C. and NiCl₂.6H₂O (19 mg, 0.081 mmol) was added. The mixture was stirred at 50° C. for 1.5 h (the mixture turned reddish) and then cooled to 0° C. A solution of 1-((cis-3-(iodomethyl)cyclobutoxy)methyl)-3-phenoxybenzene (40 mg, 0.101 mmol) in 2 mL of pyridine was added and the mixture was stirred at 5° C. for 20 h. The mixture was warmed to rt, filtered through CELITE®, and washed with EtOAc. The filtrate was washed with 1 N aq. HCl, dried (MgSO₄), and concentrated in vacuo to give methyl 4-(cis-3-(3-phenoxybenzyloxy)cyclobutyl)butanoate as a yellow oil. To a solution of the above ester (35 mg, 0.099 mmol) in MeOH (5 mL), THF (2 mL), and water (2 mL) was added LiOH.H₂O (21 mg, 0.494 mmol). The mixture was stirred at rt for 18 h and then neutralized with 1 N aq. HCl. The mixture was extracted with EtOAc. The organic layer was concentrated in vacuo. The residue was purified by preparative HPLC (PHENOMENEX® Axia Luna 5µ 21.2×250 mm column; flow rate=25 mL/min, 50 to 100% Solvent B over 10 min, hold to 12 min, where Solvent A=90:10:0.1 H₂O: MeCN:TFA and Solvent B=90:10:0.1 MeCN:H₂O:TFA) to give the title compound (18 mg, 51% yield) as a clear oil. LCMS, [M-H]⁺=339.4. ¹H NMR (500 MHz, CD₂Cl₂) δ 7.29-7.44 (m, 3H), 7.08-7.19 (m, 2H), 6.99-7.06 (m, 3H), 6.94 (dt, J=8.0, 1.2 Hz, 1H), 4.39 (s, 2H), 3.82-3.96 (m, 1H), 2.38-2.44 (m, 2H), 2.36 (t, J=7.4 Hz, 2H), 1.74-1.82 (m, 1H), 1.45-1.63 (m, 7H). HPLC-1: Rt=10.1 min, purity=100%; HPLC-2: Rt=8.9 min, purity=91.2%.

Example 54

2-((3-(3-Phenoxybenzyloxy)cyclobutyl)methoxy)acetic acid

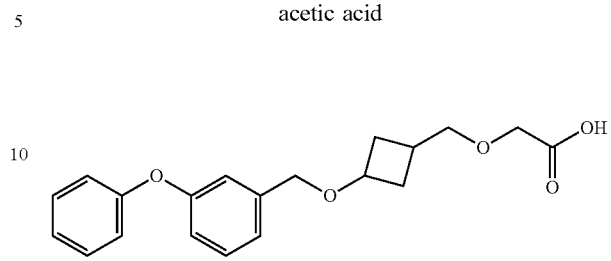

54A. (3,3-Dimethoxycyclobutyl)methanol

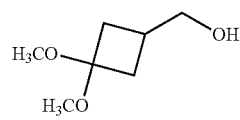

To a −78° C. solution of methyl 3,3-dimethoxycyclobutanecarboxylate (1.0 g, 5.74 mmol) in THF (20 mL) was added LAH (8.61 mL of a 1 M solution in THF, 8.61 mmol). The solution was stirred at −78° C. for 1 h and then quenched with 1 N aq. NaOH. The mixture was warmed to rt and extracted with EtOAc. The organic layer was dried (MgSO₄) and concentrated in vacuo. The residue was chromatographed (SiO₂; 50% EtOAc:hexanes) to afford the title compound (0.60 g, 68% yield). ¹H NMR (500 MHz, CDCl₃) δ 3.67 (d, J=5.8 Hz, 2H), 3.17 (s, 3H), 3.15 (s, 3H), 2.26-2.33 (m, 3H), 1.87-1.94 (m, 2H).

54B. Ethyl 2-((3,3-dimethoxycyclobutyl)methoxy)acetate

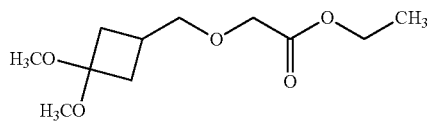 [SMILES: CCOC(=O)COCC1CC(OC)(OC)C1]

To a 0° C. solution of (3,3-dimethoxycyclobutyl)methanol (0.4 g, 2.74 mmol) in THF (10 mL) was added LHMDS (3.6 mL of a 1 M solution in THF, 3.56 mmol). The solution was stirred at 0° C. for 1 h, after which ethyl 2-bromoacetate (0.685 g, 4.10 mmol) was added. The reaction was stirred at 0° C. for another 3 h, after which water was added. The mixture was extracted with EtOAc. The organic layer was dried (MgSO₄) and concentrated in vacuo. The residue was chromatographed (SiO₂; 50% EtOAc:hexanes) to afford the title compound (0.28 g, 40% yield) as a clear oil. ¹H NMR (500 MHz, CDCl₃) δ 4.20-4.25 (m, 4H), 3.84 (s, 2H), 3.16 (s, 3H), 3.14 (s, 3H), 2.36-2.46 (m, 1H), 2.28-2.35 (m, 2H), 1.89-1.94 (m, 2H), 1.30 (t, J=7.2 Hz, 3H).

54C. Ethyl 2-((3-oxocyclobutyl)methoxy)acetate

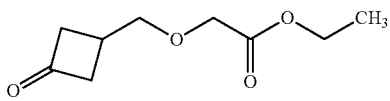

To a solution of ethyl 2-((3,3-dimethoxycyclobutyl) methoxy)acetate (0.28 g, 1.205 mmol) in MeOH (10 mL) was added aq. HCl (3 mL of a 1 M solution, 3.00 mmol). The solution was stirred at 70° C. for 2 h and then cooled to rt. Sat'd aq. NaHCO$_3$ (10 mL) was added and volatiles were removed in vacuo. The residue was extracted with EtOAc. The organic layer was dried (MgSO$_4$) and concentrated in vacuo. The residue was chromatographed (SiO$_2$; 20% EtOAc:hexanes) to afford the title compound (0.15 g, 60% yield) as a clear oil. $^1$H NMR (500 MHz, CDCl$_3$) δ 4.34-4.39 (m, 2H), 4.23 (q, J=7.2 Hz, 2H), 3.86 (s, 2H), 3.17-3.25 (m, 2H), 2.93-3.00 (m, 2H), 2.78-2.86 (m, 1H), 0.89 (t, J=7.2 Hz, 3H).

Example 54

To a 0° C. solution of ethyl 2-((3-oxocyclobutyl)methoxy) acetate (0.15 g, 0.806 mmol) in MeOH (5 mL) was added NaBH$_4$ (0.030 g, 0.806 mmol). The solution was stirred at 0° C. for 1 h and then quenched with sat'd aq. NaHCO$_3$. The mixture was concentrated in vacuo. The residue was extracted with EtOAc. The organic layer was dried (MgSO$_4$) and concentrated in vacuo. The residue was taken up in DCM (5 mL) and added oxo((trifluoromethyl)sulfonyl)silver (0.269 g, 1.05 mmol) followed by 2,6-di-tert-butylpyridine (0.185 g, 0.967 mmol) at 0° C. The solution was stirred for 30 min and 1-(chloromethyl)-3-phenoxybenzene (0.264 g, 1.21 mmol) was added. The mixture was stirred at rt for 18 h, then was diluted with DCM and washed with sat'd aq. NaHCO$_3$. The organic layer was dried (MgSO$_4$) and concentrated in vacuo. The residue was dissolved in MeOH (5 mL) and 1 N aq. NaOH (2 mL) was added. The solution was stirred at rt for 17 h, then was neutralized with 1 N aq. HCl and concentrated in vacuo. The residue was taken up in EtOAc and washed with 1 N aq. HCl. The organic layer was dried (MgSO$_4$) and concentrated in vacuo. The residue was purified by preparative HPLC (PHENOMENEX® Axia Luna 5μ 21.2×250 mm column; flow rate=25 mL/min, 50 to 100% Solvent B over 10 min, hold to 12 min, where Solvent A=90:10:0.1 H$_2$O:MeCN:TFA and Solvent B=90:10:0.1 MeCN:H$_2$O:TFA) to give the title compound (0.7 mg, 0.2% yield) as a pale yellow oil. LCMS, [M+H]$^+$=343.3. $^1$H NMR (500 MHz, CD$_2$Cl$_2$) δ 7.26-7.39 (m, 3H), 7.11 (t, J=7.4 Hz, 1H), 7.04-7.09 (m, 1H), 6.96-7.03 (m, 3H), 6.91 (d, J=9.6 Hz, 1H), 4.34-4.41 (m, 2H), 4.03-4.12 (m, 2H), 3.90-3.98 (m, 1H), 3.51-3.61 (m, 2H), 2.33-2.42 (m, 3H), 1.68-1.78 (m, 2H). HPLC-1: Rt=9.0 min, purity=95.0%; HPLC-2: Rt=7.8 min, purity=95.0%.

Example 55

3-((Cis-3-(3-phenoxybenzyloxy)cyclobutyl)methoxy)propanoic acid

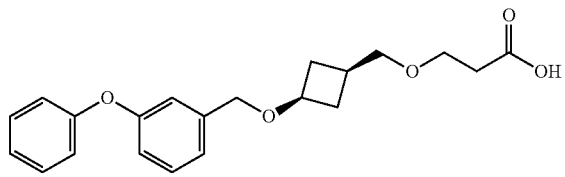 [SMILES: O=C(O)CCOC[C@H]1C[C@@H](OCc2cccc(Oc3ccccc3)c2)C1]

To a solution of (cis-3-((3-phenoxybenzyl)oxy)cyclobutyl)methanol (50 mg, 0.176 mmol) in toluene (5 mL) was added methyl acrylate (38 mg, 0.440 mmol) and N,N,N-trimethyl-1-phenylmethanaminium hydroxide (29 mg, 0.18 mmol). The solution was stirred at rt for 26 h and then acidified with 1 N aq. HCl. The mixture was extracted with EtOAc (2×). The combined organic extracts were dried (MgSO$_4$) and concentrated in vacuo to afford the crude methyl 3-((cis-3-(3-phenoxybenzyloxy)cyclobutyl) methoxy) propanoate. To a solution of this ester (50 mg, 0.135 mmol) in THF (5 mL) was added aq. LiOH (1 mL of a 2 M solution, 2.0 mmol). The mixture was stirred at rt for 24 h, then was neutralized with 1 N aq. HCl and concentrated in vacuo. The residue was taken up in EtOAc and washed with 1 N aq. HCl. The organic layer was dried (MgSO$_4$) and concentrated in vacuo. The residue was purified by preparative HPLC (PHENOMENEX® Axia Luna 5 μ21.2×250 mm column; flow rate=25 mL/min, 40 to 100% Solvent B over 10 min, hold to 12 min, where Solvent A=90:10:0.1 H$_2$O:MeCN:TFA and Solvent B=90:10:0.1 MeCN:H$_2$O:TFA) to give the title compound (10 mg, 20% yield) as a clear oil. LCMS, [M−H]$^+$=355.1. $^1$H NMR (400 MHz, CD$_2$Cl$_2$) δ 7.17-7.29 (m, 3H), 6.85-7.06 (m, 5H), 6.81 (dd, J=7.7, 2.2 Hz, 1H), 4.27 (s, 2H), 3.77-3.88 (m, 1H), 3.60 (t, J=6.2 Hz, 2H), 3.36 (d, J=6.6 Hz, 2H), 2.51 (t, J=6.2 Hz, 2H), 2.17-2.31 (m, 2H), 1.91-2.04 (m, 1H), 1.52-1.65 (m, 2H). HPLC-1: Rt=9.3 min, purity=100%; HPLC-2: Rt=7.8 min, purity=95.0%.

Example 56

2-(3-(Trans-3-(3-phenoxyphenyl)cyclobutyl) propoxy)acetic acid

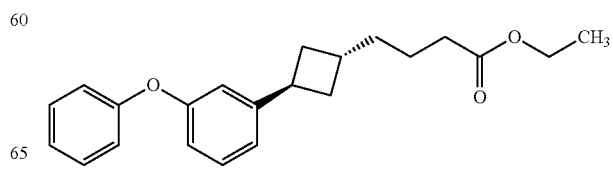

56A. Trans-ethyl 3-hydroxy-3-(3-phenoxyphenyl)cyclobutanecarboxylate

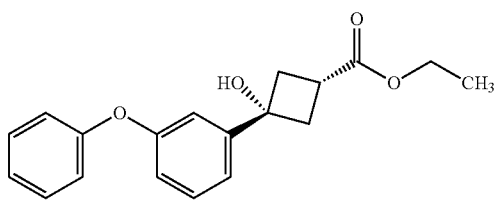 [SMILES: CCOC(=O)[C@H]1C[C@](O)(c2cccc(Oc3ccccc3)c2)C1]

To a −78° C. solution of 1-bromo-3-phenoxybenzene (1.05 g, 4.22 mmol) in 20 mL THF at was added n-BuLi (0.422 mL of a 10 M solution in THF, 4.22 mmol) over 5 min. The solution was stirred at −78° C. for 45 min and then slowly added into a −78° C. solution of ethyl 3-oxocyclobutanecarboxylate (0.5 g, 3.52 mmol) in THF (5 mL). The reaction was stirred at −78° C. for 2.5 h, then was quenched with sat'd aq. NH$_4$Cl. The mixture was warmed to rt and extracted with EtOAc. The organic layer was dried over MgSO$_4$ and concentrated in vacuo. The residue was purified by preparative HPLC (PHENOMENEX® Axia Luna 5μ 21.2×250 mm column; flow rate=25 mL/min, 60 to 100% Solvent B over 10 min, hold to 12 min, where Solvent A=90:10:0.1 H$_2$O:MeCN:TFA and Solvent B=90:10:0.1 MeCN:H$_2$O:TFA) to give trans-ethyl 3-hydroxy-3-(3-phenoxyphenyl)cyclobutanecarboxylate (0.32 g, 29% yield) as the major product. $^1$H NMR (500 MHz, DMSO-d$_6$) δ 7.32-7.46 (m, 3H), 7.25-7.32 (m, 1H), 7.09-7.18 (m, 2H), 6.98-7.04 (m, 2H), 6.83-6.92 (m, 1H), 5.65-5.87 (m, 1H), 4.03-4.13 (m, 3H), 2.74-2.86 (m, 1H), 2.56-2.65 (m, 2H), 2.44-2.55 (m, 2H), 1.12-1.23 (m, J=4.4 Hz, 2H). Also isolated is cis-ethyl 3-hydroxy-3-(3-phenoxyphenyl)cyclobutanecarboxylate (0.12 g, 11% yield) as the later eluting isomer. LCMS [M+Na]$^+$=335.0.

56B. Trans-3-(3-phenoxyphenyl)cyclobutanecarboxylic acid

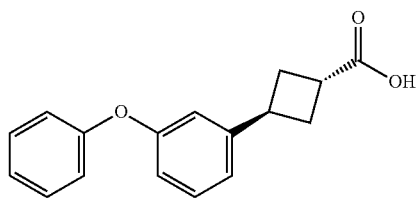 [SMILES: O=C(O)[C@H]1C[C@H](c2cccc(Oc3ccccc3)c2)C1]

A mixture of ethyl 3-hydroxy-3-(3-phenoxyphenyl)cyclobutanecarboxylate (0.20 g, 0.64 mmol), trimethylsilane (0.51 mL, 3.2 mmol), and TFA (0.49 mL, 6.4 mmol) was stirred at 80° C. for 5 h and then at rt for 16 h. The solution was concentrated in vacuo and the residue was purified by preparative HPLC (PHENOMENEX® Axia Luna 5μ 21.2×250 mm column; flow rate=25 mL/min, 60 to 100% Solvent B over 10 min, hold to 12 min, where Solvent A=90:10:0.1 H$_2$O:MeCN:TFA and Solvent B=90:10:0.1 MeCN:H$_2$O:TFA) to give the title compound (11 mg, 6% yield) as a clear oil. $^1$H NMR (500 MHz, CD$_2$Cl$_2$) δ 7.34 (dd, J=7.4, 8.5 Hz, 2H), 7.28 (t, J=7.8 Hz, 1H), 7.08-7.13 (m, 1H), 6.97-7.02 (m, 3H), 6.91 (t, J=2.1 Hz, 1H), 6.80-6.84 (m, 1H), 3.71-3.80 (m, 1H), 3.13-3.21 (m, 1H), 2.65-2.72 (m, 2H), 2.40-2.49 (m, 2H).

56C. Trans-3-(3-phenoxyphenyl)cyclobutanecarbaldehyde

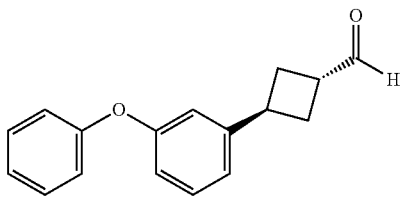 [SMILES: O=C[C@H]1C[C@H](c2cccc(Oc3ccccc3)c2)C1]

To a solution of trans-3-(3-phenoxyphenyl)cyclobutanecarboxylic acid (30 mg, 0.112 mmol) in 5 mL of THF at 0° C. was added DIBAL-H (0.25 mL of a 1 M solution in THF, 0.25 mmol). The reaction was stirred at 78° C. for 1 h and then at rt for 18 h. The reaction was quenched with sat'd aq. NaHCO$_3$ and extracted with EtOAc. The organic layer was dried over MgSO$_4$ and concentrated in vacuo. The residue was dissolved in 10 mL of DCM and Dess-Martin periodinane (71 mg, 0.168 mmol) was added at 0° C. The solution was stirred at 0° C. for 30 min and at rt for 2 h. The reaction was quenched with sat'd aq. NaHCO$_3$ and extracted with DCM. The organic layer was dried over MgSO$_4$ and concentrated in vacuo. The residue was chromatographed (SiO$_2$; 10% EtOAc:hexanes) to afford the title compound (28 mg, 96% yield) as a clear oil. $^1$H NMR (400 MHz, CDCl$_3$) δ 5.70-5.75 (m, 1H), 4.50 (d, J=3.5 Hz, 2H), 4.37-4.45 (m, 3H).

56D. (E)-Ethyl 3-(trans-3-(3-phenoxyphenyl)cyclobutyl)acrylate

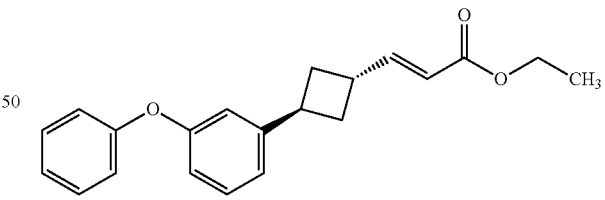

To a solution of trans-3-(3-phenoxyphenyl)cyclobutanecarbaldehyde (30 mg, 0.119 mmol) in 5 mL of DCM was added ethyl 2-(triphenylphosphoranylidene)acetate (50 mg, 0.143 mmol). The reaction was stirred for at 75° C. for 1 h and then cooled to rt. The mixture was concentrated in vacuo and the residue was chromatographed (SiO$_2$; 10% EtOAc:hexanes) to afford the title compound (31 mg, 77% yield) as a clear oil. $^1$H NMR (400 MHz, CDCl$_3$) δ 7.19-7.30 (m, 4H), 7.14-7.18 (m, 1H), 6.71-7.06 (m, 8H), 5.79 (dd, J=15.5, 1.4 Hz, 1H), 4.14 (q, J=7.1 Hz, 2H), 3.56 (quin, J=8.4 Hz, 1H), 3.01-3.09 (m, 1H), 2.23-2.42 (m, 4H), 1.23 (t, J=7.1 Hz, 3H).

56E. Ethyl 3-(trans-3-(3-phenoxyphenyl)cyclobutyl)propanoate

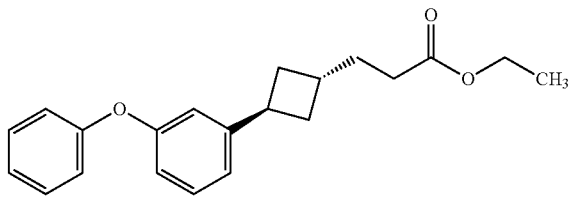 [SMILES: CCOC(=O)CC[C@H]1C[C@H](c2cccc(Oc3ccccc3)c2)C1]

To a solution of (E)-ethyl 3-(trans-3-(3-phenoxyphenyl)cyclobutyl)acrylate (30 mg, 0.093 mmol) in MeOH (5 mL) was added Pd/C (10 mg, 10% on charcoal). The mixture was stirred under an atmosphere of $H_2$ for 1 h and then filtered through CELITE®. The filtrate was concentrated in vacuo to give the title compound (30 mg, 94% yield) as a clear oil. $^1$H NMR (400 MHz, $CDCl_3$) δ 7.31-7.37 (m, 2H), 6.91-7.15 (m, 5H), 6.83 (d, J=7.3 Hz, 1H), 4.09-4.23 (m, 2H), 3.59 (br. s., 1H), 2.24-2.35 (m, 5H), 2.12 (d, J=5.3 Hz, 2H), 1.93 (br. s., 2H), 1.26-1.36 (m, 3H).

56F. 3-(Trans-3-(3-phenoxyphenyl)cyclobutyl)propan-1-ol

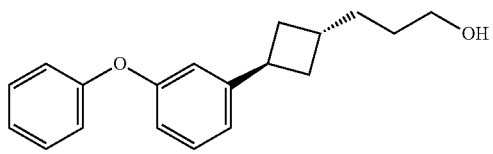 [SMILES: OCCC[C@H]1C[C@H](c2cccc(Oc3ccccc3)c2)C1]

To a solution of ethyl 3-(trans-3-(3-phenoxyphenyl)cyclobutyl)propanoate (30 mg, 0.092 mmol) in 20 mL of DCM at −78° C. was added DIBAL-H (0.20 mL of a 1 M solution in DCM, 0.20 mmol). The reaction was stirred at −78° C. for 30 min and EtOAc (5 mL) was added followed by 1 N aq. NaOH. The mixture was warmed to rt and extracted with EtOAc. The organic layer was dried over $MgSO_4$ and concentrated in vacuo. The residue was chromatographed ($SiO_2$; 30% EtOAc:hexanes) to afford the title compound (24 mg, 87% yield) as a clear oil. $^1$H NMR (500 MHz, $CD_2Cl_2$) δ 7.35-7.40 (m, 2H), 7.30 (t, J=7.8 Hz, 1H), 7.11-7.18 (m, 1H), 7.02-7.07 (m, 3H), 6.97 (t, J=1.9 Hz, 1H), 6.83 (dd, J=7.8, 2.1 Hz, 1H), 3.55-3.70 (m, 3H), 2.25-2.35 (m, 3H), 2.09-2.18 (m, 2H), 1.64-1.71 (m, 2H), 1.53-1.61 (m, 2H).

Example 56

To a solution of 3-(trans-3-(3-phenoxyphenyl)cyclobutyl)propan-1-ol (25 mg, 0.089 mmol) in 5 mL of toluene was added tert-butyl 2-bromoacetate (23 mg, 0.115 mmol), aq. NaOH (5 mL of a 0.018 M solution, 0.090 mmol) and $Bu_4NCl·H_2O$ (8 mg, 0.027 mmol). The reaction mixture was stirred at rt for 20 h and then diluted with EtOAc. The mixture was washed with 1 N aq. HCl, dried ($MgSO_4$), and concentrated in vacuo to give tert-butyl 2-(3-(trans-3-(3-phenoxyphenyl)cyclobutyl)propoxy)acetate (30 mg, 77% yield). This ester was dissolved in 2.5 mL of DCM and TFA (2.5 mL, 32.4 mmol) was added. The reaction mixture was stirred at rt for 30 min, then was concentrated in vacuo. The residue was purified by preparative HPLC (PHENOMENEX® Axia Luna 5μ 21.2×250 mm column; flow rate=25 mL/min, gradient from 50 to 100% Solvent B over 10 min, hold for 12 min, where Solvent A=90:10:0.1 $H_2O$:MeCN:TFA and Solvent B=90:10:0.1 MeCN:$H_2O$:TFA) to give the title compound (14 mg, 51% yield) as a clear oil. LCMS, [M+H]$^+$=341.2. $^1$H NMR (500 MHz, $CD_2Cl_2$) δ 7.37 (dd, J=8.8, 7.4 Hz, 2H), 7.30 (t, J=7.8 Hz, 1H), 7.11-7.16 (m, 1H), 7.01-7.07 (m, 3H), 6.95-6.98 (m, 1H), 6.83 (dd, J=8.1, 1.8 Hz, 1H), 4.11 (s, 2H), 3.57-3.65 (m, 3H), 2.26-2.34 (m, 3H), 2.09-2.15 (m, 2H), 1.62-1.69 (m, 4H). HPLC-1: Rt=10.6 min, purity=100%; HPLC-2: Rt=8.8 min, purity=93.1%.

Example 57

2-(2-(3-(3-Phenoxybenzyloxy)cyclobutyl)ethoxy)acetic acid

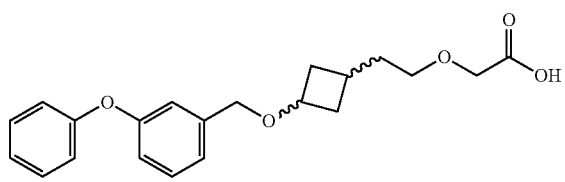 [SMILES: O=C(O)COCCC1CC(OCc2cccc(Oc3ccccc3)c2)C1]

57A. Ethyl 2-(3-(benzyloxy)cyclobutylidene)acetate

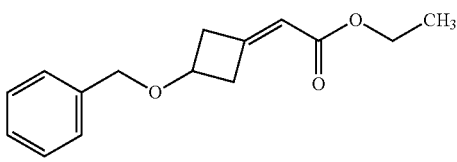 [SMILES: CCOC(=O)C=C1CC(OCc2ccccc2)C1]

A solution of 3-(benzyloxy)cyclobutanone (0.75 g, 4.26 mmol) and methyl 2-(triphenylphosphoranylidene)acetate (1.71 g, 5.11 mmol) in 10 mL of DCM was stirred at 60° C. for 3 h. The solution was cooled to rt and concentrated in vacuo. The residue was chromatographed ($SiO_2$; 10% EtOAc:hexanes) to afford the title compound (0.61 g, 52% yield) as a clear oil. $^1$H NMR (500 MHz, $CDCl_3$) δ 7.30-7.42 (m, 5H), 5.69-5.78 (m, 1H), 4.44-4.54 (m, 2H), 4.10-4.28 (m, 3H), 3.46-3.55 (m, 1H), 2.97-3.12 (m, 2H), 2.84-2.94 (m, 1H).

57B. Ethyl 2-(3-(benzyloxy)cyclobutyl)acetate

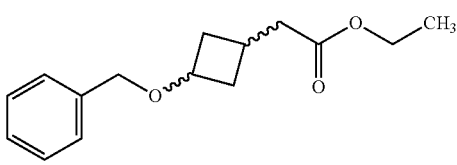 [SMILES: CCOC(=O)CC1CC(OCc2ccccc2)C1]

To a solution of ethyl 2-(3-(benzyloxy)cyclobutylidene)acetate (0.60 g, 2.44 mmol) in MeOH (10 mL) was added Pd/C (0.1 g, 0.940 mmol). The mixture was hydrogenated at 60 psi pressure for 5 days, then the $H_2$ was released and the mixture was filtered through CELITE® and concentrated in vacuo to give the title compound (0.45 g, 74% yield). $^1$H NMR (500 MHz, CDCl$_3$) δ 7.30-7.37 (m, 5H), 4.43 (m, 2H), 4.11-4.16 (m, 2H), 3.86-3.99 (m, 1H), 2.48-2.54 (m, 2H), 2.45 (d, J=7.4 Hz, 2H), 1.67-1.74 (m, 2H).

57C. 2-(3-(Benzyloxy)cyclobutyl)ethanol

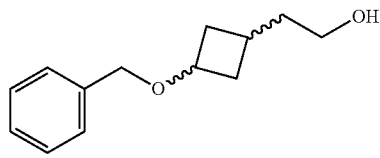 [SMILES: OCCC1CC(OCc2ccccc2)C1]

To a -78° C. solution of ethyl 2-(3-(benzyloxy)cyclobutyl)acetate (0.45 g, 1.81 mmol) in DCM (20 mL) at was added DIBAL-H (3.99 mL of a 1 M solution in DCM, 3.99 mmol). The reaction was stirred at -78° C. for 3 h and then EtOAC (5 mL) was added, followed by 1 N aq. NaOH (10 mL). The mixture was warmed to rt and the organic layer was separated. The aqueous layer was extracted with EtOAc. The combined organic extracts were dried over MgSO$_4$ and concentrated in vacuo. The residue was chromatographed (SiO$_2$; 30% EtOAc:hexanes) to afford the title compound (0.32 g, 86% yield) as a colorless oil. $^1$H NMR (500 MHz, CD$_2$Cl$_2$) δ 7.29-7.39 (m, 5H), 4.42 (s, 2H), 3.88-3.96 (m, 1H), 3.59 (t, J=6.5 Hz, 2H), 2.41-2.48 (m, 2H), 1.66-1.74 (m, 3H), 1.58-1.65 (m, 2H).

57D. tert-Butyl 2-(2-(3-(benzyloxy)cyclobutyl)ethoxy)acetate

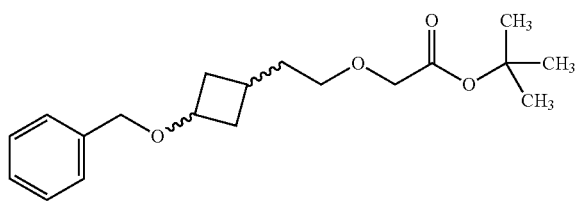 [SMILES: CC(C)(C)OC(=O)COCCC1CC(OCc2ccccc2)C1]

To a solution of 2-(3-(benzyloxy)cyclobutyl)ethanol (50 mg, 0.242 mmol) in 5 mL of toluene was added tert-butyl 2-bromoacetate (71 mg, 0.361 mmol) and NaOH (5 mL of a 0.048 M solution, 0.24 mmol). To the mixture was added Bu$_4$NCl.H$_2$O (22 mg, 0.073 mmol). The reaction mixture was stirred for 20 h at rt, then was diluted with EtOAc and washed with 1 N aq. HCl. The aqueous washed was extracted with EtOAc. The combined organic layers were dried (MgSO$_4$) and concentrated in vacuo to give the title compound (45 mg, 0.126 mmol, 52.1% yield) as a pale yellow oil.

57E. tert-Butyl 2-(2-(3-hydroxycyclobutyl)ethoxy)acetate

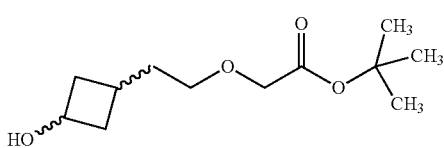 [SMILES: CC(C)(C)OC(=O)COCCC1CC(O)C1]

To a solution of tert-butyl 2-(2-(3-(benzyloxy)cyclobutyl)ethoxy)acetate (50 mg, 0.156 mmol) in 10 mL of methanol was added 10% Pd/C (10 mg, 9.4 μmol). The mixture was stirred under 1 atm of hydrogen for 18 h. The mixture was filtered and added a fresh 10% Pd/C (10 mg, 9.4 μmol) and stirred for 7 h under 50 psi of hydrogen. The mixture was filtered and concentrated in vacuo to give the title compound (30 mg, 0.117 mmol, 75% yield) as a colorless oil.

57F. tert-Butyl 2-(2-(3-((3-phenoxybenzyl)oxy)cyclobutyl)ethoxy)acetate

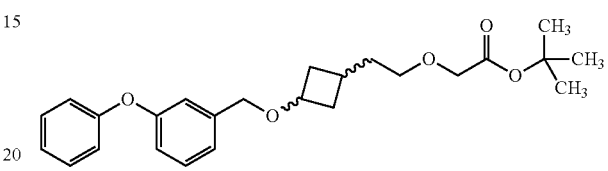

To a solution of tert-butyl 2-(2-(3-hydroxycyclobutyl)ethoxy)acetate (35 mg, 0.15 mmol) in 5 mL of DCM was added 2,6-di-tert-butylpyridine (44 mg, 0.23 mmol) and 1-(chloromethyl)-3-phenoxybenzene (67 mg, 0.30 mmol). The solution was stirred for 10 min at rt and AgOTf (59 mg, 0.23 mmol) was added. The mixture was stirred for 5 days, then was diluted with DCM and washed with 1 N aq. NaOH. The aqueous layer was extracted with additional DCM. The combined organic extracts were dried (MgSO$_4$) and concentrated in vacuo to give the crude title compound (45 mg, 0.093 mmol, 61.0% yield) as a pale yellow oil. LCMS, [M+Na]$^+$=435.1.

Example 57

To a solution of tert-butyl 2-(2-(3-((3-phenoxybenzyl)oxy)cyclobutyl)ethoxy) acetate (15 mg, 0.036 mmol) in MeOH (5 mL) was added NaOH (1 mL of 1.0 M aq. solution, 1.00 mmol). The reaction was stirred for 20 h at rtm, then was acidified with 1 N aq. HCl to pH ~2 and concentrated in vacuo. The residue was taken up with EtOAc and washed with 1 N aq. HCl. The organic layer was dried (MgSO$_4$) and concentrated in vacuo. The residue was purified with Prep. HPLC (YMC reverse phase PHENOMENEX® 30×100 mm Axia Luna column; flow rate=40 mL/min, 0 to 100% Solvent B:A over 30 min, hold to 40 min, where Solvent A=90:10:0.1 H$_2$O:CH$_3$CN:TFA and Solvent B=90:10:0.1 CH$_3$CN:H$_2$O:TFA) to give 2-(2-(3-((3-phenoxybenzyl)oxy)cyclobutyl)ethoxy) acetic acid (5.2 mg, 0.014 mmol, 38.5% yield) as a pale yellow oil. LCMS, [M–H]$^+$=355.1. $^1$H NMR (500 MHz, CD$_2$Cl$_2$) δ 7.36-7.41 (m, 2H), 7.34 (t, J=7.8 Hz, 1H), 7.13-7.17 (m, 1H), 7.08-7.12 (m, 1H), 7.01-7.06 (m, 3H), 6.94 (dd, J=8.0, 2.0 Hz, 1H), 4.33-4.47 (m, 2H), 4.03-4.12 (m, 2H), 3.81-3.98 (m, 1H), 3.51-3.63 (m, 2H), 2.39-2.49 (m, 2H), 1.83-1.94 (m, 1H), 1.78 (quin, J=6.7 Hz, 3H), 1.54-1.68 (m, 3H). HPLC-1: Rt=9.5 min, purity=100%; HPLC-2: Rt=8.1 min, purity=98.1%.

Example 58

2-(3-(Cis-3-(3-phenoxyphenyl)cyclobutyl)propoxy) acetic acid

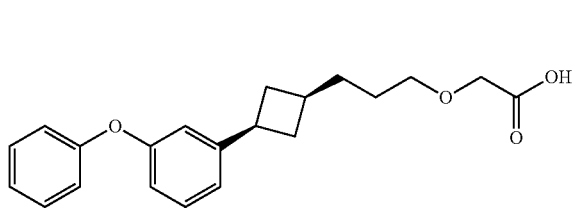 [SMILES: O=C(O)COCCC[C@H]1C[C@@H](c2cccc(Oc3ccccc3)c2)C1]

58A. Cis-ethyl 3-(3-phenoxyphenyl)cyclobutanecarboxylate

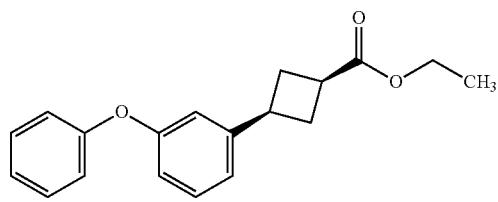 [SMILES: CCOC(=O)[C@H]1C[C@@H](c2cccc(Oc3ccccc3)c2)C1]

A mixture of cis-ethyl 3-hydroxy-3-(3-phenoxyphenyl) cyclobutanecarboxylate (0.2 g, 0.640 mmol), trimethylsilane (0.511 ml, 3.20 mmol), and TFA (0.493 ml, 6.40 mmol) was stirred at 80° C. for 5 h, then was cooled to rt and stirred at rt for 16 h. Volatiles were removed in vacuo and the residue was purified by preparative HPLC (PHENOMENEX® Axia Luna 5μ 21.2×250 mm column; flow rate=25 mL/min, gradient from 60 to 100% Solvent B:Solvent A over 10 min, hold for 12 min, where Solvent A=90:10:0.1 H$_2$O:MeCN: TFA and Solvent B=90:10:0.1 MeCN:H$_2$O:TFA) to give the title compound (0.095 g, 50% yield) as a colorless oil. $^1$H NMR (500 MHz, CD$_2$Cl$_2$) δ 7.33 (dd, J=7.6, 8.4 Hz, 2H), 7.26 (t, J=8.0 Hz, 1H), 7.09 (t, J=7.4 Hz, 1H), 6.95-7.01 (m, 3H), 6.89 (s, 1H), 6.78-6.83 (m, 1H), 4.10 (q, J=7.2 Hz, 2H), 3.37-3.47 (m, 1H), 3.01-3.12 (m, 1H), 2.52-2.62 (m, 2H), 2.29-2.38 (m, 2H), 1.23 (t, J=7.2 Hz, 3H).

58B. Cis-3-(3-phenoxyphenyl)cyclobutanecarbaldehyde

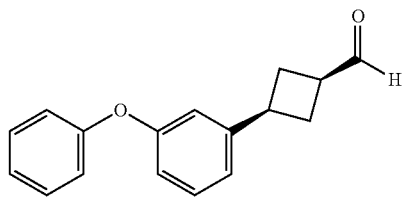 [SMILES: O=C[C@H]1C[C@@H](c2cccc(Oc3ccccc3)c2)C1]

The title compound (colorless oil) was prepared from cis-ethyl 3-(3-phenoxy-phenyl)cyclobutanecarboxylate using a procedure analogous to the synthesis of trans-3-(3-phenoxyphenyl)cyclobutanecarbaldehyde. $^1$H NMR (400 MHz, CDCl$_3$) δ 5.70-5.75 (m, 1H), 4.50 (d, J=3.5 Hz, 2H), 4.37-4.45 (m, 3H).

58C. (E)-3-(Cis-3-(3-phenoxyphenyl)cyclobutyl) acrylaldehyde

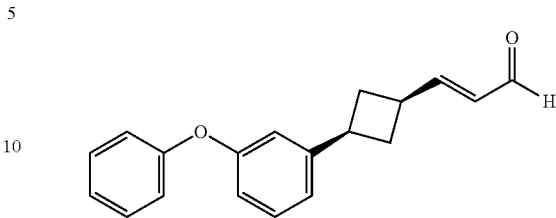

A solution of cis-3-(3-phenoxyphenyl)cyclobutanecarbaldehyde (30 mg, 0.119 mmol) and 2-(triphenylphosphoranylidene)acetaldehyde (47 mg, 0.155 mmol) in DCM (5 mL) was stirred at 60° C. for 2.5 days, then was cooled to rt and stirred at rt for 2 days. The mixture was concentrated in vacuo and the residue was chromatographed (SiO$_2$; 10% EtOAc:hexanes) to afford the title compound (26 mg, 75% yield) as a colorless oil. $^1$H NMR (400 MHz, CD$_2$Cl$_2$) δ 9.50 (d, J=7.8 Hz, 1H), 7.31-7.39 (m, 2H), 7.27 (t, J=7.8 Hz, 1H), 7.07-7.14 (m, 1H), 6.94-7.04 (m, 3H), 6.85-6.93 (m, 2H), 6.79-6.84 (m, 1H), 6.04 (ddd, J=1.4, 7.8, 15.5 Hz, 1H), 3.43-3.56 (m, 1H), 3.12-3.26 (m, 1H), 2.59-2.71 (m, 2H), 2.03-2.15 (m, 2H).

58D. 3-(Cis-3-(3-phenoxyphenyl)cyclobutyl)propan-1-ol

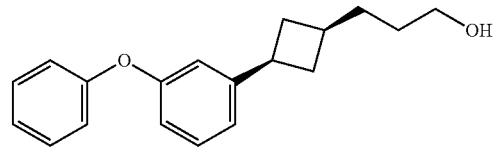 [SMILES: OCCC[C@H]1C[C@@H](c2cccc(Oc3ccccc3)c2)C1]

To a solution of (E)-3-(cis-3-(3-phenoxyphenyl)cyclobutyl)acrylaldehyde (26 mg, 0.093 mmol) in MeOH (5 mL) was added Pd/C (10 mg, 9.40 nmol). The mixture was stirred under an ambient atmosphere of H$_2$ for 3 h. The reaction mixture was filtered through CELITE® and the filtrate was concentrated in vacuo to give 3-(cis-3-(3-phenoxyphenyl) cyclobutyl)propanal (20 mg, 69% yield). To a solution of this aldehyde (20 mg, 0.071 mmol) in MeOH (5 mL) at 0° C. was added NaBH$_4$ (3 mg, 0.086 mmol). The solution was stirred at 0° C. for 10 min and then allowed to warm to rt and stirred at rt for 1 h. The reaction was quenched with sat'd aq. NaHCO$_3$ and concentrated in vacuo. The residue was taken up in EtOAc. The organic layer was dried (MgSO$_4$) and concentrated in vacuo to afford the title compound (20 mg, 89% yield) as a clear oil. $^1$H NMR (500 MHz, CD$_2$Cl$_2$) δ 7.28-7.37 (m, 2H), 7.24 (t, J=7.8 Hz, 1H), 7.06-7.12 (m, 1H), 6.92-7.01 (m, 3H), 6.87 (br. s., 1H), 6.75-6.80 (m, 1H), 3.28-3.37 (m, 1H), 2.40-2.53 (m, 2H), 2.17-2.28 (m, 1H), 1.61-1.72 (m, 2H), 1.37-1.55 (m, 4H), 1.19-1.31 (m, 2H).

Example 58

The title compound (colorless oil) was prepared from 3-(cis-3-(3-phenoxyphenyl)cyclobutyl)propan-1-ol using a procedure analogous to that for the synthesis of Example 56. LCMS, [M−H]$^+$=339.1. $^1$H NMR (500 MHz, CD$_2$Cl$_2$) δ 7.36 (t, J=7.8 Hz, 2H), 7.27 (t, J=7.8 Hz, 1H), 7.12 (t, J=7.4

Hz, 1H), 6.96-7.03 (m, 3H), 6.90 (s, 1H), 6.81 (dd, J=8.0, 2.0 Hz, 1H), 4.06 (br. s., 2H), 3.57 (t, J=6.3 Hz, 2H), 3.29-3.40 (m, 1H), 2.51 (qd, J=7.9, 2.8 Hz, 2H), 2.23-2.29 (m, 1H), 1.67-1.75 (m, 2H), 1.56-1.62 (m, 2H), 1.43-1.52 (m, 2H). HPLC-1: Rt=10.7 min, purity=100%; HPLC-2: Rt=9.0 min, purity=95.0%.

Example 59

2-(3-(Cis-3-(3-phenoxybenzyloxy)cyclobutyl)propoxy)acetic acid

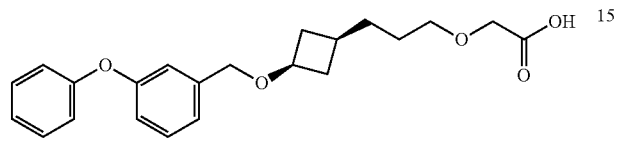

59A.
Cis-3-((3-phenoxybenzyl)oxy)cyclobutanecarboxylic acid

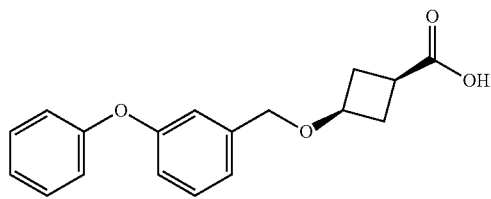 [SMILES: O=C(O)[C@H]1C[C@@H](OCc2cccc(Oc3ccccc3)c2)C1]

A mixture of ethyl 3-hydroxy-3-(3-phenoxyphenyl)cyclobutanecarboxylate (0.20 g, 0.64 mmol), trimethylsilane (0.51 mL, 3.2 mmol), and TFA (0.49 mL, 6.4 mmol) was stirred at 80° C. for 5 h and then at rt for 16 h. The solution was concentrated in vacuo and the residue was purified by preparative HPLC (PHENOMENEX® Axia Luna 5µ 21.2× 250 mm column; flow rate=25 mL/min, 60 to 100% Solvent B over 10 min, hold to 12 min, where Solvent A=90:10:0.1 H$_2$O:MeCN:TFA and Solvent B=90:10:0.1 MeCN:H$_2$O:TFA) to give the title compound (20 mg, 12% yield) as a clear oil. $^1$H NMR (500 MHz, methylene chloride-d$_2$) δ 7.37-7.30 (m, 2H), 7.27 (t, J=7.9 Hz, 1H), 7.13-7.07 (m, 1H), 7.02-6.96 (m, 3H), 6.90 (t, J=2.2 Hz, 1H), 6.82 (ddd, J=8.2, 2.5, 1.0 Hz, 1H), 3.47 (tt, J=10.1, 8.1 Hz, 1H), 3.15 (tt, J=9.8, 8.2 Hz, 1H), 2.67-2.58 (m, 2H), 2.44-2.32 (m, 2H).

59B. (E)-Ethyl 3-(cis-3-(3-phenoxybenzyloxy)cyclobutyl)acrylate

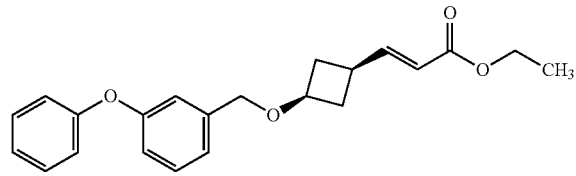 [SMILES: CCOC(=O)/C=C/[C@H]1C[C@@H](OCc2cccc(Oc3ccccc3)c2)C1]

(E)-Ethyl 3-(cis-3-(3-phenoxybenzyloxy)cyclobutyl)acrylate (colorless oil) was prepared using a procedure analogous to (E)-ethyl 3-(trans-3-(3-phenoxyphenyl)cyclobutyl)acrylate except that trans-3-(3-phenoxyphenyl)cyclobutanecarboxylic acid was replaced with cis-3-(3-phenoxyphenyl)cyclobutanecarboxylic acid. $^1$H NMR (500 MHz, CD$_2$Cl$_2$) δ 7.35 (dd, J=7.4, 8.5 Hz, 2H), 7.30 (t, J=8.0 Hz, 1H), 7.09-7.13 (m, 1H), 7.04-7.08 (m, 1H), 6.97-7.02 (m, 3H), 6.93-6.97 (m, 1H), 6.89-6.93 (m, 1H), 5.74 (dd, J=1.4, 15.4 Hz, 1H), 4.38 (s, 2H), 4.15 (q, J=7.2 Hz, 2H), 3.91-3.99 (m, 1H), 2.53-2.62 (m, 1H), 2.44-2.51 (m, 2H), 1.82-1.90 (m, 2H), 0.89 (t, J=7.2 Hz, 3H).

59C. 3-(Cis-3-(3-phenoxybenzyloxy)cyclobutyl)propan-1-ol

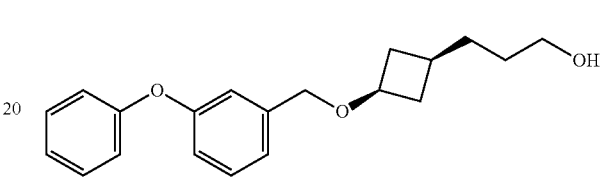

To a solution of (E)-ethyl 3-(cis-3-((3-phenoxybenzyl)oxy)cyclobutyl)acrylate (0.06 g, 0.170 mmol) in MeOH (10 mL) was added 10% Pd/C (0.018 g, 0.170 mmol). The mixture was stirred for 4 h under 1 atm of hydrogen. The mixture was filtered through CELITE® and concentrated in vacuo to give 30 mg of ethyl 3-(cis-3-((3-phenoxybenzyl)oxy)cyclobutyl)propanoate as an oil. The 3-(cis-3-(3-phenoxybenzyloxy) cyclobutyl) propan-1-ol (colorless oil) was then prepared using a procedure analogous to (cis-3-(3-phenoxybenzyloxy)cyclobutyl)methanol except that cis-ethyl 3-(3-phenoxybenzyloxy)cyclobutanecarboxylate was replaced with ethyl 3-(cis-3-((3-phenoxybenzyl)oxy)cyclobutyl)propanoate. $^1$H NMR (500 MHz, CD$_2$Cl$_2$) δ 7.32-7.37 (m, 2H), 7.30 (t, J=7.8 Hz, 1H), 7.11 (t, J=7.3 Hz, 1H), 7.07 (dd, J=0.6, 7.4 Hz, 1H), 6.96-7.02 (m, 3H), 6.88-6.92 (m, 1H), 4.35 (s, 2H), 3.80-3.89 (m, 1H), 3.52-3.60 (m, 2H), 2.32-2.40 (m, 2H), 1.69-1.79 (m, 1H), 1.40-1.55 (m, 6H).

Example 59

Example 59 was prepared using a procedure analogous to Example 56 except that 3-(trans-3-(3-phenoxyphenyl)cyclobutyl)propan-1-ol was replaced with 3-(cis-3-(3-phenoxybenzyloxy)cyclobutyl)propan-1-ol. LCMS, [M−H]$^+$=369.2. $^1$H NMR (400 MHz, CD$_2$Cl$_2$) δ 7.25-7.37 (m, 3H), 7.03-7.14 (m, 2H), 6.96-7.02 (m, 3H), 6.87-6.92 (m, 1H), 4.34 (s, 2H), 3.98-4.05 (m, 2H), 3.79-3.89 (m, 1H), 3.46-3.55 (m, 2H), 2.30-2.41 (m, 2H), 1.63-1.78 (m, 1H), 1.38-1.58 (m, 6H). HPLC-1: Rt=9.9 min, purity=95.0%; HPLC-2: Rt=8.4 min, purity=91.8%.

Example 60

2-(3-(Cis-1-methyl-3-(3-phenoxyphenyl)cyclobutyl)propoxy)acetic acid

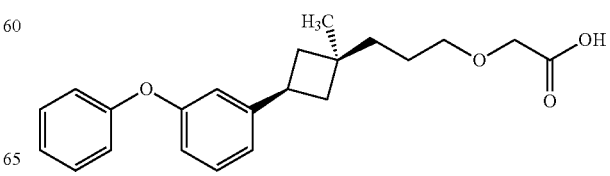

60A. Cis-ethyl 1-methyl-3-(3-phenoxyphenyl)cyclobutanecarboxylate and Trans-ethyl 1-methyl-3-(3-phenoxyphenyl)cyclobutanecarboxylate

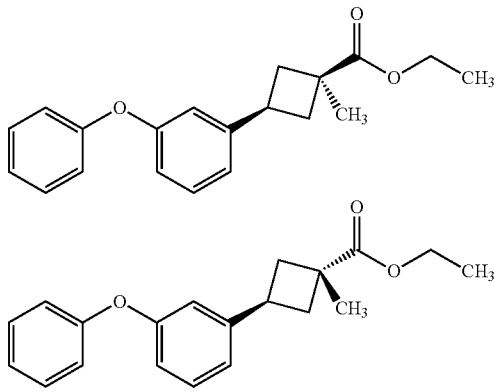

An LDA (lithium diisopropyl amide) solution was prepared by the slow addition of n-BuLi (0.12 mL of a 10 M solution in hexanes, 1.22 mmol) into a solution of iPr₂NH (0.22 mL, 1.52 mmol) in 10 mL of THF at −78° C. and the solution was stirred for 30 min at −78° C. A solution of cis-ethyl 3-(3-phenoxyphenyl)cyclobutanecarboxylate (0.30 g, 1.012 mmol) in THF (5 mL) was added dropwise to the above LDA solution at −78° C. The reaction was stirred for 1 h at −78° C., after which MeI (0.076 mL, 1.22 mmol) was added. The reaction was stirred for 2 h at −78° C. and then quenched with sat'd aq NH₄Cl. The mixture was warmed to rt and extracted with EtOAc (2×). The combined organic extracts were dried (MgSO₄) and concentrated in vacuo. The residue was purified by Preparative HPLC (PHENOMENEX® 30×100 mm Axia Luna column, 60 to 100% Solvent B over 10 min, where Solvent A=90:10:0.1 H₂O:MeCN:TFA and Solvent B=90:10:0.1 MeCN:H₂O:TFA) to afford cis-ethyl 1-methyl-3-(3-phenoxyphenyl) cyclobutanecarboxylate (0.15 g, 0.459 mmol, 45.4% yield) as a colorless oil. LCMS, [M+H]⁺=311. ¹H NMR (500 MHz, CD₂Cl₂) δ 7.40-7.35 (m, 2H), 7.30 (t, J=7.9 Hz, 1H), 7.16-7.12 (m, 1H), 7.05-7.02 (m, 3H), 6.95 (t, J=2.1 Hz, 1H), 6.84 (ddd, J=8.2, 2.6, 1.0 Hz, 1H), 4.14 (q, J=7.1 Hz, 2H), 3.58 (p, J=9.1 Hz, 1H), 2.58 (td, J=9.7, 2.6 Hz, 2H), 2.39-2.21 (m, 2H), 1.54 (s, 3H), 1.27 (t, J=7.1 Hz, 3H).

Also isolated is trans-ethyl 1-methyl-3-(3-phenoxyphenyl) cyclobutanecarboxylate (82 mg, 0.238 mmol, 23.49% yield). LCMS, [M+H]⁺=311. ¹H NMR (500 MHz, CDCl₃) δ 7.37-7.29 (m, 2H), 7.27-7.24 (m, 1H), 7.12-7.06 (m, 1H), 7.03-6.98 (m, 2H), 6.94 (ddt, J=7.6, 1.8, 0.9 Hz, 1H), 6.87 (t, J=2.3 Hz, 1H), 6.81 (ddd, J=8.0, 2.6, 1.0 Hz, 1H), 4.21 (q, J=7.1 Hz, 2H), 3.56 (p, J=9.2 Hz, 1H), 2.87 (ddd, J=9.9, 9.0, 2.6 Hz, 2H), 2.06 (td, J=9.7, 2.6 Hz, 2H), 1.37 (s, 3H), 1.30 (t, J=7.1 Hz, 3H).

60B. (Cis-1-methyl-3-(3-phenoxyphenyl)cyclobutyl)methanol

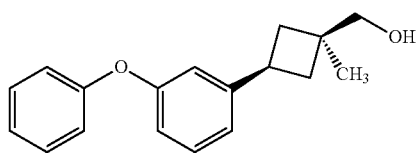 [SMILES: C[C@]1(CO)C[C@@H](c2cccc(Oc3ccccc3)c2)C1]

To a solution of cis-ethyl 1-methyl-3-(3-phenoxyphenyl) cyclobutanecarboxylate (0.15 g, 0.483 mmol) in 10 mL of DCM was added DIBAL-H (1.063 mL of a 1 M solution in DCM, 1.063 mmol) at −78° C. The solution was stirred for 1 h at −78° C. and then allowed to warm to rt. EtOAc was added and the mixture was washed with 1 N aq. HCl. The aqueous layer was extracted with EtOAc (2×). The combined organic extracts were dried (MgSO₄) and concentrated in vacuo to give the title compound (0.13 g, 0.46 mmol, 95% yield) as a colorless oil. ¹H NMR (500 MHz, CDCl₃) δ ppm 7.35 (dd, J=8.80, 7.43 Hz, 2H), 7.25-7.28 (m, 1H), 7.09-7.14 (m, 1H), 6.97-7.05 (m, 3H), 6.92-6.93 (m, 1H), 6.82 (dd, J=7.84, 2.06 Hz, 1H), 3.54 (p, J=9.1 Hz, 1H), 3.42 (s, 2H), 2.07-2.11 (m, 4H) 1.28 (s, 3H).

60C. Cis-1-methyl-3-(3-phenoxyphenyl)cyclobutanecarbaldehyde

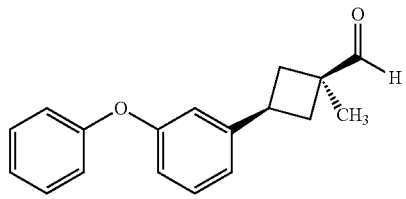 [SMILES: C[C@]1(C=O)C[C@@H](c2cccc(Oc3ccccc3)c2)C1]

To a solution of (cis-1-methyl-3-(3-phenoxyphenyl)cyclobutyl)methanol (0.13 g, 0.484 mmol) in 10 mL of DCM was added Dess-Martin Periodinane (0.205 g, 0.484 mmol) at 0° C. The mixture was warmed to rt and stirred for 2 h. The mixture was added saturated aq. NaHCO₃ and extracted with DCM. The organic layer was dried (MgSO₄) and concentrated in vacuo. The residue was purified with silica gel (EOAc/hexanes=1/9; 12 g cartridge) to give the title compound (0.11 g, 0.392 mmol, 81% yield) as a colorless oil. ¹H NMR (400 MHz, CDCl₃) δ ppm 9.51 (s, 1H), 7.26 (dd, J=8.58, 7.26 Hz, 2H), 7.19 (t, J=5.05 Hz, 1H), 7.01-7.06 (m, 1H), 6.93 (dd, J=8.69, 1.21 Hz, 2H), 6.87-6.91 (m, 1H), 6.80 (t, J=1.98 Hz, 1H), 6.71-6.77 (m, 1H), 3.62 (quin, J=9.13 Hz, 1H), 2.37-2.46 (m, 2H), 2.05-2.12 (m, 2H), 1.40 (s, 3H).

60D. (E)-Ethyl 3-(cis-1-methyl-3-(3-phenoxyphenyl)cyclobutyl)acrylate

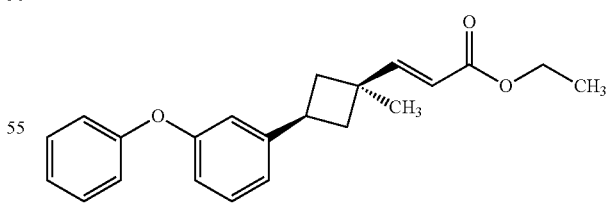

A solution of cis-1-methyl-3-(3-phenoxyphenyl)cyclobutanecarbaldehyde (0.11 g, 0.413 mmol) and ethyl 2-(triphenylphosphoranylidene)acetate (0.173 g, 0.496 mmol) in DCM was stirred for 2 h at 60° C. and then for 2 days at rt. Volatiles were removed in vacuo and the residue was chromatographed (SiO₂; 12 g; EtOAc:Hexanes 1:20) to give the title compound (0.105 g, 0.306 mmol, 74.1% yield) as a colorless oil; none of the corresponding Z isomer was observed from the ¹H NMR. ¹H NMR (500 MHz, CD₂Cl₂) δ ppm 7.22-7.27 (m, 2H), 7.17 (t, J=7.84 Hz, 1H), 7.01 (tt, J=7.43, 1.10 Hz, 1H), 6.94 (d, J=15.96 Hz, 1H), 6.86-6.91 (m, 3H), 6.79 (t, J=2.06 Hz, 1H), 6.71 (ddd, J=8.18, 2.41, 0.69 Hz, 1H), 5.62 (d, J=15.68 Hz, 1H), 4.06 (q, J=7.15 Hz, 2H), 3.53 (quin, J=9.08 Hz, 1H), 2.07-2.23 (m, 4H), 1.34 (s, 3H), 1.18 (t, J=7.15 Hz, 3H).

60E. Ethyl 3-(cis-1-methyl-3-(3-phenoxyphenyl)cyclobutyl)propanoate

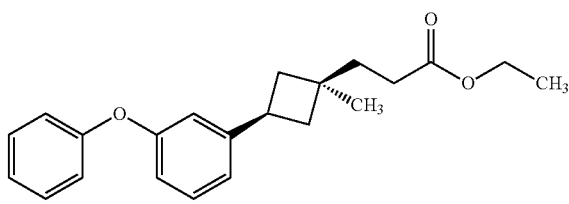 [SMILES: CCOC(=O)CC[C@]1(C)C[C@H](c2cccc(Oc3ccccc3)c2)C1]

To a solution of (E)-ethyl 3-(cis-1-methyl-3-(3-phenoxyphenyl)cyclobutyl) acrylate (75 mg, 0.223 mmol) in MeOH (10 mL) was added 10% Pd/C (24 mg, 0.022 mmol). The mixture was stirred under 1 atm of H₂ for 3 h at rt. The reaction mixture was filtered and the filtrate was concentrated in vacuo to give the title compound (75 mg, 0.217 mmol, 97% yield) as a colorless oil. ¹H NMR (500 MHz, CDCl₃) δ ppm 7.34-7.38 (m, 2H), 7.27 (t, J=7.98 Hz, 1H), 7.09-7.14 (m, 1H), 7.01-7.05 (m, 2H), 6.94-6.98 (m, 1H), 6.87-6.90 (m, 1H), 6.82 (dd, J=7.84, 2.06 Hz, 1H), 4.14 (q, J=7.15 Hz, 2H), 3.41-3.58 (m, 1H), 2.21-2.29 (m, 2H), 2.08-2.18 (m, 2H), 1.89-1.97 (m, 2H), 1.71-1.79 (m, 2H), 1.28 (t, J=7.02 Hz, 3H), 1.25 (s, 3H).

60F. 3-(Cis-1-methyl-3-(3-phenoxyphenyl)cyclobutyl)propan-1-ol

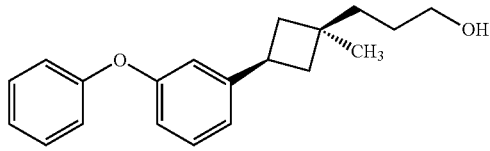 [SMILES: C[C@]1(CCCO)C[C@@H](c2cccc(Oc3ccccc3)c2)C1]

To a −78° C. solution of ethyl 3-(cis-1-methyl-3-(3-phenoxyphenyl)cyclobutyl)propanoate (70 mg, 0.207 mmol) in 5 mL of DCM was added DIBAL-H (0.517 mL of a 1 M solution in DCM, 0.517 mmol). The solution was stirred for 1 h at −78° C., after which EtOAc (2 mL) was added, followed by sat'd aq. NaHCO₃. The mixture was allowed to warm to rt and extracted with EtOAc (2×). The combined organic extracts were dried (MgSO₄) and concentrated in vacuo to give the title compound (60 mg, 0.192 mmol, 93% yield) as a colorless oil. ¹H NMR (500 MHz, CD₂Cl₂) δ ppm 7.37 (t, J=7.84 Hz, 2H), 7.28 (t, J=7.84 Hz, 1H), 7.14 (t, J=7.29 Hz, 1H), 6.99-7.05 (m, 3H), 6.92 (s, 1H), 6.82 (d, J=7.98 Hz, 1H), 3.61 (t, J=6.46 Hz, 2H), 3.54 (t, J=9.08 Hz, 1H), 2.16 (td, J=8.94, 2.48 Hz, 2H), 1.87-1.96 (m, 2H), 1.49-1.56 (m, 2H), 1.40-1.47 (m, 2H), 1.28 (s, 3H).

60G. tert-Butyl 2-(3-(cis-1-methyl-3-(3-phenoxyphenyl)cyclobutyl)propoxy)acetate

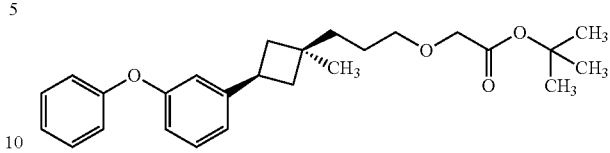

To a solution of 3-(cis-1-methyl-3-(3-phenoxyphenyl)cyclobutyl)propan-1-ol (60 mg, 0.202 mmol) in toluene (5 mL) was added tert-butyl 2-bromoacetate (99 mg, 0.506 mmol) and 30% aq. NaOH (5 mL, 0.20 mmol). The reaction mixture was stirred for 3 days at rt, then was taken up with EtOAc and washed with 1 N aq. HCl. The organic layer was dried (MgSO₄) and concentrated in vacuo. The residue was chromatographed (SiO₂; 12 g; EtOAc:Hexanes=1/9) to give the title compound (55 mg, 0.127 mmol, 62.9% yield) as a colorless oil. ¹H NMR (500 MHz, CD₂Cl₂) δ ppm 7.24 (dd, J=8.53, 7.43 Hz, 2H), 7.15 (t, J=7.98 Hz, 1H), 6.99-7.02 (m, 1H), 6.86-6.92 (m, 3H), 6.79 (t, J=1.79 Hz, 1H), 6.67-6.71 (m, 1H), 3.81 (s, 2H), 3.41 (t, J=8.94 Hz, 1H), 3.36 (t, J=6.60 Hz, 2H), 1.99-2.05 (m, 2H), 1.77-1.83 (m, 2H), 1.40-1.46 (m, 2H), 1.40 (s, 3H), 1.37 (s, 9H), 1.30-1.36 (m, 2H).

Example 60

To a solution of tert-butyl 2-(3-(cis-1-methyl-3-(3-phenoxyphenyl)cyclobutyl) propoxy)acetate (50 mg, 0.122 mmol) in 5 mL of DCM was added TFA (2 mL, 26.0 mmol). The solution was stirred for 1 h at rt and concentrated in vacuo. The residue was purified by Preparative HPLC (PHENOMENEX® 30×100 mm Axia Luna column, 70 to 100% Solvent B over 10 min, where Solvent A=90:10:0.1 H₂O:MeCN:TFA and Solvent B=90:10:0.1 MeCN:H₂O:TFA) to give the title compound (25 mg, 0.069 mmol, 57% yield) as a colorless oil. LCMS, [M−H]⁺=353.2. ¹H NMR (500 MHz, CD₂Cl₂) δ ppm 7.37 (dd, J=8.53, 7.43 Hz, 2H), 7.28 (t, J=7.84 Hz, 1H), 7.10-7.16 (m, 1H), 7.01-7.03 (m, 2H), 6.98-7.01 (m, 1H), 6.91 (s, 1H), 6.78-6.82 (m, 1H), 4.08 (s, 2H), 3.48-3.63 (m, 3H), 2.10-2.20 (m, 2H), 1.86-1.98 (m, 2H), 1.54-1.64 (m, 2H), 1.43-1.49 (m, 2H), 1.27 (s, 3H). HPLC-1: Rt=11.0 min, purity=95%; HPLC-2: RT=9.15 min, purity=95%.

Example 61

2-(3-(Trans-1-methyl-3-(3-phenoxyphenyl)cyclobutyl)propoxy)acetic acid

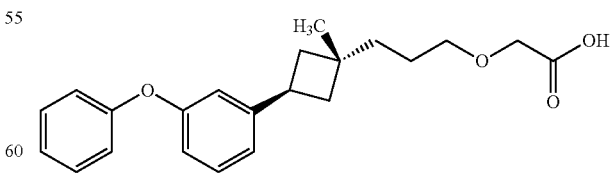

The title compound (colorless oil) was prepared using a procedure analogous to Example 60 except that cis-ethyl 1-methyl-3-(3-phenoxyphenyl)cyclobutane carboxylate was replaced with trans-ethyl 1-methyl-3-(3-phenoxyphenyl)cyclobutanecarboxylate. LCMS, [M−H]⁺=353.2. ¹H NMR (400 MHz, CD$_2$Cl$_2$) δ ppm 7.34-7.41 (m, 2H), 7.29 (t, J=7.81 Hz, 1H), 7.10-7.18 (m, 1H), 6.99-7.06 (m, 3H), 6.89-6.95 (m, 1H), 6.82 (dd, J=8.14, 1.76 Hz, 1H), 4.13 (s, 2H), 3.60-3.70 (m, 2H), 3.46 (t, J=9.13 Hz, 1H), 2.21-2.35 (m, 2H), 1.87-1.94 (m, 2H), 1.60-1.75 (m, 4H), 1.11 (s, 3H). HPLC-1: RT=11.0 min, purity=100%; HPLC-2: Rt=9.14 min. purity=97%.

Example 62

3-(3-(Cis-1-methyl-3-(3-phenoxyphenyl)cyclobutyl)propoxy)propanoic acid

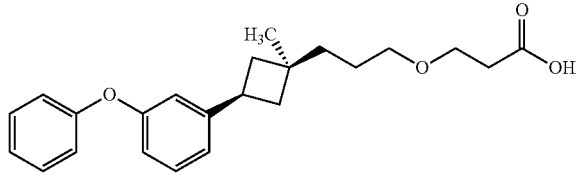 [SMILES: C[C@]1(CCCOCCC(=O)O)C[C@@H](c2cccc(Oc3ccccc3)c2)C1]

To a solution of 3-(cis-1-methyl-3-(3-phenoxyphenyl)cyclobutyl)propan-1-ol (35 mg, 0.19 mmol) in 5 mL of toluene was added tert-butyl acrylate (38 mg, 0.30 mmol) and N,N,N-trimethyl-1-phenylmethanaminium hydroxide (49 mg, 0.12 mmol). The solution was stirred for 4 days at rt. The solution was taken up in EtOAc and washed with 1 N aq. HCl. The organic layer was dried (MgSO$_4$) and concentrated in vacuo. The residue was dissolved in DCM (2 mL) and TFA (1 mL, 12.98 mmol) was added. The solution was stirred for 2 h at rt and concentrated in vacuo. The residue was purified by Preparative HPLC (PHENOMENEX® 30×100 mm Axia Luna column, 70 to 100% Solvent B over 10 min, where Solvent A=90:10:0.1 H$_2$O:MeCN:TFA and Solvent B=90:10:0.1 MeCN:H$_2$O:TFA) to give the title compound (4.5 mg, 0.011 mmol, 9.6% yield) as a colorless oil. LCMS, [M−H]$^+$=367.3. $^1$H NMR (500 MHz, CD$_2$Cl$_2$) δ ppm 7.33-7.39 (m, 2H), 7.28 (t, J=7.84 Hz, 1H), 7.09-7.18 (m, 1H), 6.96-7.04 (m, 3H), 6.92 (s, 1H), 6.81 (dd, J=7.98, 1.93 Hz, 1H), 3.71 (br. s., 2H), 3.37-3.57 (m, 3H), 2.62 (br. s., 2H), 2.12-2.18 (m, 2H), 1.87-1.95 (m, 2H), 1.52-1.60 (m, 2H), 1.39-1.46 (m, 2H), 1.26 (s, 3H). HPLC-1: Rt=11.3 min, purity=90%; HPLC-2: Rt=9.34 min. purity=90%.

Example 63

Trans-2-(((3-(3-phenoxyphenyl)cyclobutyl)methoxy)methyl)cyclopropanecarboxylic acid

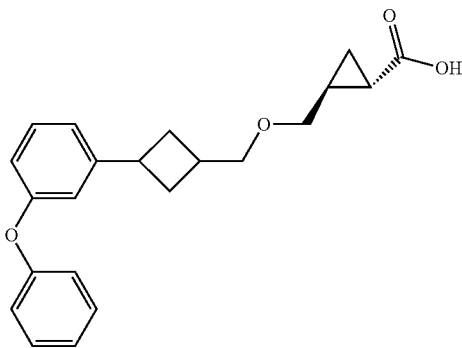 [SMILES: O=C(O)[C@H]1C[C@@H]1COCC1CC(c2cccc(Oc3ccccc3)c2)C1]

63A. 1-(3-((Benzyloxy)methyl)cyclobutyl)-3-phenoxybenzene

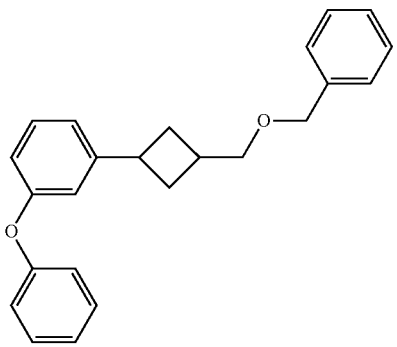 [SMILES: c1ccc(COCC2CC(c3cccc(Oc4ccccc4)c3)C2)cc1]

A solution of 3-((benzyloxy)methyl)cyclobutanone (100 mg, 0.526 mmol) and 4-methylbenzenesulfonylhydrazide (98 mg, 0.526 mmol) in 1,4-dioxane (2 mL) was stirred under Ar at 80° C. for 90 min in a sealed tube, then was cooled to rt. K$_2$CO$_3$ (109 mg, 0.788 mmol) and (3-phenoxyphenyl)boronic acid (169 mg, 0.788 mmol) were added to the reaction mixture. The reaction mixture was heated at 110° C. with stirring for 10 h, then was cooled to rt, and volatiles were removed in vacuo. CH$_2$Cl$_2$ (5 mL) and sat'd aq. NaHCO$_3$ (5 mL) were added and the layers were separated. The aqueous phase was extracted with CH$_2$Cl$_2$ (3×5 mL). The combined organic extracts were washed with brine (5 mL), dried (MgSO$_4$) and filtered. Volatiles were removed in vacuo to afford the crude product, which was chromatographed (SiO$_2$; EtOAc/hexanes, 0% to 100% of EtOAc in 12 min) to give the title compound (25 mg, 0.073 mmol, 13.8% yield) as a colorless oil. LCMS, [M+H]$^+$=345.1.

63B. (3-(3-Phenoxyphenyl)cyclobutyl)methanol

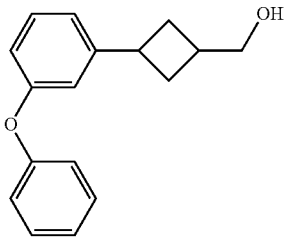 [SMILES: OCC1CC(c2cccc(Oc3ccccc3)c2)C1]

A solution of 1-(3-((benzyloxy)methyl)cyclobutyl)-3-phenoxybenzene (25 mg, 0.073 mmol) and Pd/C (20 mg, 0.188 mmol), in THF (1 mL) was stirred at rt under 1 atm of H$_2$ for 14 h. The reaction was diluted with CH$_2$Cl$_2$ (5 mL) and was filtered through a plug of CELITE®. The filtrate was concentrated in vacuo to afford the crude title compound (18 mg, 0.073 mmol, 100% yield) as a colorless oil. LCMS, [M+Na]$^+$=276.9. $^1$H NMR (500 MHz, CD$_2$Cl$_2$) δ 7.38-6.81 (m, 9H), 3.81 (d, J=7.1 Hz, 1H), 3.66-3.56 (m, 1.6H), 3.48-3.39 (m, 0.4H), 2.57-2.43 (m, 1.8H), 2.34-2.19 (m, 2.4H), 4.35 (s, 2H), 1.94-1.85 (m, 0.8H).

63C. Trans-ethyl 2-(((3-(3-phenoxyphenyl)cyclobutyl)methoxy)methyl) cyclopropanecarboxylate

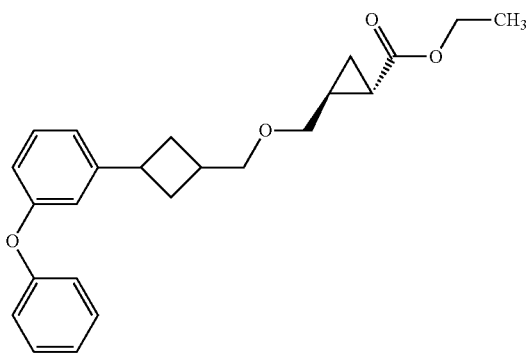 [SMILES: CCOC(=O)[C@H]1C[C@@H]1COCC1CC(c2cccc(Oc3ccccc3)c2)C1]

A suspension of (3-(3-phenoxyphenyl)cyclobutyl)methanol (20 mg, 0.079 mmol), 2,6-di-tert-butylpyridine (0.062 mL, 0.275 mmol) and AgOTf (61 mg, 0.236 mmol) in CH$_2$Cl$_2$ (0.6 mL) was cooled to 0° C. under Ar. Trans-ethyl 2-(bromomethyl) cyclopropanecarboxylate (49 mg, 0.236 mmol) was added. The mixture was stirred at rt for 14 h, then was diluted with CH$_2$Cl$_2$ (3 mL) and saturated aq. NH$_4$Cl (1 mL). The mixture was extracted with CH$_2$Cl$_2$ (3×3 mL), dried (MgSO$_4$) and concentrated in vacuo to afford the crude product. This crude material was chromatographed (SiO$_2$; EtOAc/hexanes, gradient of 0% to 100% of EtOAc over 12 min) to afford the title compound (25 mg, 0.066 mmol, 84% yield; mixture of isomers) as a colorless oil. LCMS, [M+Na]$^+$=403. $^1$H NMR (500 MHz, CDCl$_3$) δ 7.37-7.30 (m, 2H), 7.28-7.21 (m, 1H), 7.09 (t, J=7.4 Hz, 1H), 7.03-6.93 (m, 3H), 6.90 (dd, J=18.1, 2.1 Hz, 1H), 6.84-6.77 (m, 1H), 4.20-4.08 (m, 2H), 3.60-3.52 (m, 2H), 3.46-3.33 (m, 3H), 2.60-2.41 (m, 2H), 2.31-2.16 (m, 2H), 1.86 (qd, J=10.2, 9.6, 2.0 Hz, 1H), 1.76-1.66 (m, 1H), 1.61-1.52 (m, 1H), 1.30-1.17 (m, 4H), 0.91-0.82 (m, 1H).

Example 63

A solution of trans-ethyl 2-(((3-(3-phenoxyphenyl)cyclobutyl)methoxy) methyl)cyclopropanecarboxylate (25 mg, 0.066 mmol) and LiOH.H$_2$O (54 mg, 1.31 mmol) in THF (1 mL), water (1 mL), MeOH (1 mL) was heated to 80° C. for 2 h in a microwave reactor. The reaction was cooled to rt, then was acidified with 1N aq. HCl to pH=2-3. The mixture was extracted with EtOAc (4×5 mL), dried (MgSO$_4$) and concentrated in vacuo to afford the crude product. This material was purified via preparative LC/MS (Column: Waters XBridge C18, 19×200 mm, 5-μm particles; Mobile Phase A: 5:95 MeCN:H$_2$O with 10 mM NH$_4$OAc; Mobile Phase B: 95:5 MeCN:H$_2$O with 10 mM NH$_4$OAc; Gradient: 30-70% B:A over 15 min, then a 5-min hold at 100% B; Flow rate: 20 mL/min. LCMS), to afford the title compound (18.1 mg, 75% yield). [M+Na]$^+$=375.2. $^1$H NMR (500 MHz, CDCl$_3$) δ 7.32 (t, J=7.7 Hz, 2H), 7.28-7.20 (m, 1H), 7.09 (t, J=7.4 Hz, 1H), 7.02-6.93 (m, 3H), 6.89 (d, J=18.7 Hz, 1H), 6.80 (dt, J=6.6, 3.0 Hz, 1H), 3.60-3.53 (m, 2H), 3.49-3.26 (m, 3H), 2.58-2.40 (m, 2H), 2.33-2.08 (m, 2H), 1.85 (q, J=10.3, 9.9 Hz, 1H), 1.81-1.68 (m, 1H), 1.60-1.51 (m, 1H), 1.29-1.20 (m, 1H), 1.00-0.82 (m, 1H). HPLC-4: RT=1.81 min, HPLC-5: RT=2.16 min, purity=96%.

Example 64

Trans-3-((2'-fluoro-5'-phenoxy-[1,1'-biphenyl]-4-yl)oxy)cyclobutanecarboxylic acid

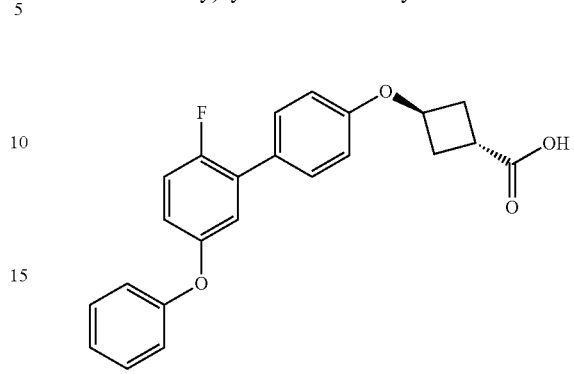

and

Example 65

Cis-3-((2'-fluoro-5'-phenoxy-[1,1'-biphenyl]-4-yl)oxy)cyclobutanecarboxylic acid

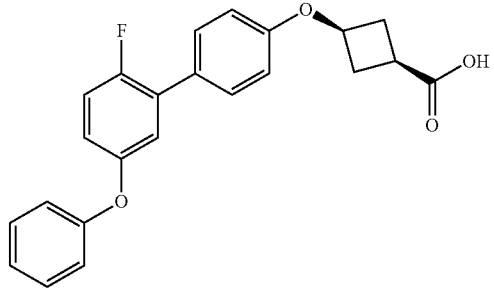 [SMILES: O=C(O)[C@H]1C[C@@H](Oc2ccc(-c3cc(Oc4ccccc4)ccc3F)cc2)C1]

64A. Methyl 3-((methylsulfonyl)oxy)cyclobutanecarboxylate

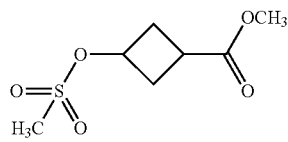

To a 0° C. solution of methyl 3-hydroxycyclobutanecarboxylate (1 g, 7.68 mmol) in pyridine (20 mL) under N$_2$ was added methanesulfonyl chloride (0.714 mL, 9.22 mmol) dropwise while maintaining the temperature at 0° C. Once the addition was complete, the reaction was allowed to warm to rt and stirred at rt for 14 h. The reaction was diluted with EtOAc (20 mL) and washed with water (20 mL), cold 5N aq. HCl (3×10 mL), water (10 mL), and brine (10 mL). The organic layer was dried (MgSO$_4$) and concentrated in vacuo to afford the title compound (243 mg, 1.167 mmol, 15.19% yield) as a light yellow oil, which was used in the next step without further purification. LCMS, [M+H]$^+$=209.

64B. (Methyl 3-(4-bromophenoxy)cyclobutanecarboxylate

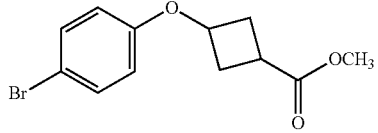 [SMILES: COC(=O)C1CC(Oc2ccc(Br)cc2)C1]

A mixture of crude methyl 3-((methylsulfonyl)oxy)cyclobutanecarboxylate (243 mg, 1.167 mmol) from above, 4-bromophenol (252 mg, 1.457 mmol) and $Cs_2CO_3$ (1.25 g, 3.84 mmol) in DMF (2 mL) was heated for 16 h at 100° C., then was cooled to RT, diluted with $H_2O$ (2 mL), and extracted with EtOAc (3×3 mL). The combined organic extracts were dried ($MgSO_4$) and concentrated in vacuo. The crude product was purified by preparative HPLC (YMC reverse phase ODS-A-5μ 30×100 mm column; flow rate=40 mL/min, 0 to 100% Solvent B:A over 30 min, hold to 40 min, where Solvent A=90:10:0.1 $H_2O:CH_3CN:TFA$ and Solvent B=90:10:0.1 $CH_3CN:H_2O:TFA$) to give the title compound (40 mg, 0.140 mmol, 12% yield) as a colorless oil. NMR indicated that this material is a mixture of the trans- and cis-isomers. LCMS, $[M+H]^+$=285. $^1$H NMR (500 MHz, $CDCl_3$) δ 7.38-7.31 (m, 2H), 6.73-6.61 (m, 2H), 4.85 (dddd, J=13.1, 7.1, 6.0, 1.0 Hz, 0.35H), 4.58-4.47 (m, 0.65H), 3.73 (s, 1.1H), 3.70 (s, 1.9H), 3.17 (ttd, J=9.9, 4.2, 1.0 Hz, 0.35H), 2.88-2.76 (m, 0.65H), 2.76-2.67 (m, 2H), 2.51-2.35 (m, 2H).

Examples 64 and 65

A mixture of trans- and cis-methyl 3-(4-bromophenoxy)cyclobutanecarboxylate (40 mg, 0.140 mmol) from above, (2-fluoro-5-phenoxyphenyl) boronic acid (48.8 mg, 0.210 mmol), $K_2CO_3$ (58.2 mg, 0.421 mmol) and $Pd(Ph_3P)_4$ (16.2 mg, 0.014 mmol) in THF (1.5 mL) in water (0.5 mL) was heated in a microwave reactor at 130° C. for 20 min, then was cooled to rt. To this reaction mixture was added MeOH (0.5 mL) and KOH (157 mg, 2.80 mmol). The reaction mixture was stirred in a microwave reactor at 100° C. for 30 min, then was cooled to rt and concentrated in vacuo. The residue was acidified with 1N aq. HCl to pH=2-3. The mixture was extracted with EtOAc (3×5 mL); the combined organic extracts were dried ($MgSO_4$) and concentrated in vacuo to afford the crude product. This crude material was purified by preparative HPLC (PHENOMENEX® Luna Axia reverse phase 5μ 21.2×100 mm column; flow rate=40 mL/min, gradient from 0 to 100% Solvent B:A over 10 min, hold for 12 min, where Solvent A=90:10:0.1 $H_2O:CH_3CN:TFA$ and Solvent B=90:10:0.1 $CH_3CN:H_2O:TFA$) to give Example 64 (first eluting isomer), trans-3-((2'-fluoro-5'-phenoxy-[1,1'-biphenyl]-4-yl)oxy)cyclobutanecarboxylic acid (28.6 mg, 0.074 mmol, 53% yield) and Example 65 (second eluting isomer), cis-3-((2'-fluoro-5'-phenoxy-[1,1'-biphenyl]-4-yl)oxy) cyclobutanecarboxylic acid (12.5 mg, 0.032 mmol, 23% yield) as white solids. The stereochemistry of each product was determined by nOe experiments. Trans-isomer: LCMS, $[M-H]^+$=377.2. $^1$H NMR (500 MHz, $CDCl_3$) δ 7.54-7.42 (m, 2H), 7.37-7.30 (m, 2H), 7.15-7.05 (m, 3H), 7.03-6.99 (m, 2H), 6.92 (dt, J=8.8, 3.5 Hz, 1H), 6.89-6.83 (m, 2H), 4.64 (p, J=7.2 Hz, 1H), 2.91-2.84 (m, 1H), 2.84-2.76 (m, 2H), 2.55-2.48 (m, 2H). HPLC-1: RT=12.0 min, purity=100%; HPLC-2: RT=10.7 min, purity=100%. Cis-isomer: LCMS, $[M-H]^+$=377.2. $^1$H NMR (500 MHz, $CDCl_3$) δ 7.48-7.41 (m, 2H), 7.36-7.29 (m, 2H), 7.13-7.06 (m, 3H), 7.03-6.99 (m, 2H), 6.94-6.89 (m, 1H), 6.88-6.82 (m, 2H), 4.96 (td, J=7.1, 6.0 Hz, 1H), 3.24 (ddt, J=9.3, 6.0, 4.5 Hz, 1H), 2.81 (ddt, J=13.9, 9.2, 3.2 Hz, 2H), 2.60-2.48 (m, 2H). HPLC-1: RT=12.3 min, purity=99%; HPLC-2: RT=10.8 min, purity=99%.

Example 66

Trans-2-(3-((2'-fluoro-5'-phenoxy-[1,1'-biphenyl]-4-yl)oxy)cyclobutyl)acetic acid

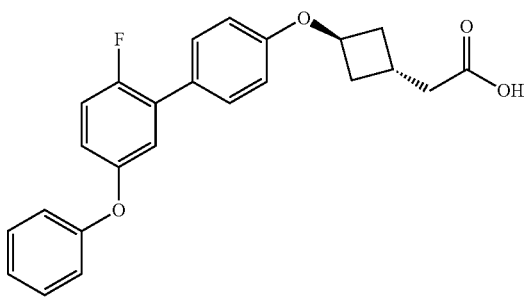 [SMILES: O=C(O)C[C@H]1C[C@H](Oc2ccc(-c3cc(Oc4ccccc4)ccc3F)cc2)C1]

To a solution of trans-3-((2'-fluoro-5'-phenoxy-[1,1'-biphenyl]-4-yl)oxy) cyclobutanecarboxylic acid (14 mg, 0.037 mmol) in $CH_2Cl_2$ (0.5 mL) at 0° C. was added $(COCl)_2$ (0.092 mL, 0.185 mmol) followed by 1 drop of DMF. After 10 min, the mixture was allowed to warm to rt and stirred for 0.5 h at rt. The reaction was concentrated in vacuo to afford the crude trans-3-((2'-fluoro-5'-phenoxy-[1,1'-biphenyl]-4-yl)oxy) cyclobutanecarbonyl chloride, which was used directly for the next step. To this crude acid chloride was added THF (0.25 mL) and MeCN (0.25 mL), followed by (diazomethyl)trimethylsilane (0.030 mL, 0.059 mmol) at 0° C. (ice water), resulting in the generation of gas. The resulting mixture was allowed to warm to rt and stirred for 14 h at rt. The reaction mixture was concentrated in vacuo to afford the crude trans-2-diazo-1-(3-((2'-fluoro-5'-phenoxy-[1,1'-biphenyl]-4-yl)oxy)cyclobutyl)ethanone as a light yellow oil, which was used directly in the next reaction. To a solution of this crude diazoketone in THF (0.6 mL) and water (0.2 mL) was added $Ag(I)NO_3$ (8 mg, 0.048 mmol). The reaction mixture was stirred for 72 h at rt, then was diluted with brine (2 mL) and extracted with EtOAc (4×3 mL). The combined organic extracts were dried ($MgSO_4$) and concentrated in vacuo to afford the crude ester product. This crude material was purified by preparative HPLC (YMC reverse phase ODS-A-5μ 30×100 mm column; flow rate=40 mL/min, gradient from 0 to 100% Solvent B:A over 30 min, hold for 40 min, where Solvent A=90:10:0.1 $H_2O:CH_3CN:TFA$ and Solvent B=90:10:0.1 $CH_3CN:H_2O:TFA$) to give the title compound (1.0 mg, 2.4 μmol, 7% overall yield) as a white solid. LCMS, $[M-H]^+$=391.2. $^1$H NMR (500 MHz, $CDCl_3$) δ 7.46-7.40 (m, 2H), 7.37-7.30 (m, 2H), 7.13-7.05 (m, 3H), 7.02-6.99 (m, 2H), 6.91 (dt, J=8.8, 3.5 Hz, 1H), 6.85 (d, J=8.5 Hz, 2H), 4.58 (br s, 1H), 2.76 (br s, 2H), 2.65-2.50 (m, 2H), 2.40 (s, 1H), 1.91 (s, 2H). HPLC-1: RT=12.4 min, purity=96%. HPLC-2: RT=10.9 min, purity=97%.

Example 67

Cis-2-(3-((2'-fluoro-5'-phenoxy-[1,1'-biphenyl]-4-yl)oxy)cyclobutyl)acetic acid

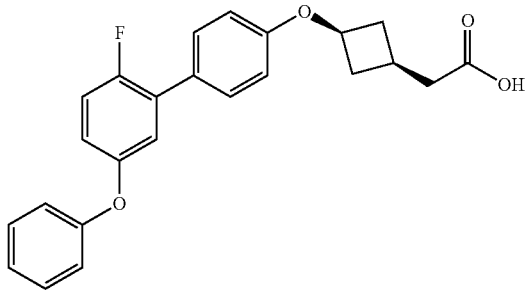 [SMILES: O=C(O)C[C@H]1C[C@@H](Oc2ccc(-c3cc(Oc4ccccc4)ccc3F)cc2)C1]

The title compound (a white solid) was prepared from cis-3-((2'-fluoro-5'-phenoxy-[1,1'-biphenyl]-4-yl)oxy)cyclobutanecarboxylic acid using a procedure analogous to the synthesis of trans-2-(3-((2'-fluoro-5'-phenoxy-[1,1'-biphenyl]-4-yl)oxy) cyclobutyl)acetic acid. LCMS, [M−H]⁺=391.2. ¹H NMR (500 MHz, CD₂Cl₂) δ 7.50-7.40 (m, 2H), 7.33 (dd, J=8.6, 7.3 Hz, 2H), 7.12-7.05 (m, 3H), 7.03-6.97 (m, 2H), 6.91 (dt, J=8.8, 3.4 Hz, 1H), 6.85-6.80 (m, 2H), 4.86-4.68 (m, 1H), 2.83 (ddt, J=12.1, 8.5, 4.2 Hz, 1H), 2.59 (d, J=7.9 Hz, 2H), 2.51-2.40 (m, 2H), 2.30 (dtd, J=13.7, 6.9, 5.9, 3.6 Hz, 2H). HPLC-1: RT=12.4 min, purity=96%. HPLC-2: RT=11.0 min, purity=97%.

Example 68

2-(3-(3-Methoxy-3-(3-phenoxyphenyl)cyclobutyl)propoxy)acetic acid

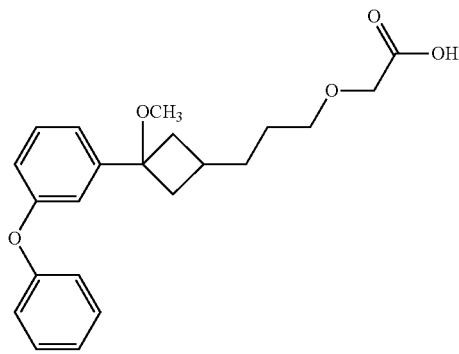 [SMILES: COC1(c2cccc(Oc3ccccc3)c2)CC(CCCOCC(=O)O)C1]

68A. Methyl 3-(3-bromophenyl)-3-methoxycyclobutanecarboxylate

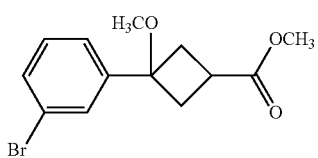 [SMILES: COC(=O)C1CC(OC)(c2cccc(Br)c2)C1]

To a solution of 3-(3-bromophenyl)-3-hydroxycyclobutanecarboxylic acid (300 mg, 1.107 mmol) in DMF (3 mL) was added NaH (111 mg, 2.77 mmol, 60% in mineral oil) at 0° C. The mixture was stirred for 10 min. Met (0.24 mL, 3.87 mmol) was added in and the reaction was allowed to warmed to rt and stirred for 72 h. The reaction was quenched with saturated NaHCO₃ solution (5 mL). The reaction mixture was extracted with EtOAc (3×5 mL). The combined organic layers dried over MgSO₄, filtered and evaporated in vacuo to afford the crude. The residue was purified by ISCO column chromatography (12 g SiO₂; 0% to 35% of EtOAc in hexanes in 15 min) to afford methyl 3-(3-bromophenyl)-3-methoxycyclobutanecarboxylate (180 mg, 0.602 mmol, 54.4% yield) as a colorless oil. LCMS, [M+H]⁺=299.0. ¹H NMR (500 MHz, chloroform-d) δ 7.56 (t, J=1.9 Hz, 1H), 7.43 (dt, J=8.1, 1.5 Hz, 1H), 7.35 (dt, J=7.7, 1.4 Hz, 1H), 7.24 (t, J=3.9 Hz, 1H), 3.69 (s, 3H), 2.92 (s, 3H), 2.80-2.69 (m, 1H), 2.62 (d, J=8.6 Hz, 4H).

68B. Methyl 3-methoxy-3-(3-phenoxyphenyl)cyclobutanecarboxylate

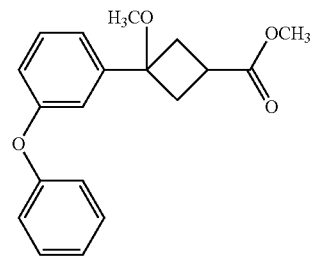 [SMILES: COC(=O)C1CC(OC)(c2cccc(Oc3ccccc3)c2)C1]

A mixture of methyl 3-(3-bromophenyl)-3-methoxycyclobutanecarboxylate (135 mg, 0.451 mmol), phenol (64 mg, 0.68 mmol), Potassium Phosphate Tribasic (192 mg, 0.903 mmol), Palladium(II) acetate (10.13 mg, 0.045 mmol) and (2'-(tert-butyl)-4',6'-diisopropyl-[1,1'-biphenyl]-2-yl)diisopropylphosphine (28 mg, 0.068 mmol) was degassed and refilled with Argon. Toluene (0.75 mL) was added in and the reaction was sealed and heated to 100° C. for 32 h. The reaction was cooled to rt, diluted with DCM (3 mL) and filtered. The filtrate was concentrated to afford the crude. This crude was purified by HPLC (PHENOMENEX®, C18, 100×30 mm, 5µ column, MeOH/H₂O with 0.1% TFA, 0% to 98% 30 min gradient, flow rate 20 mL/min) to give methyl 3-methoxy-3-(3-phenoxyphenyl)cyclobutanecarboxylate (141 mg, 0.451 mmol, 100% yield) as a colorless oil. ¹H NMR (500 MHz, chloroform-d) δ 7.35 (t, J=7.9 Hz, 3H), 7.18 (dd, J=7.8, 1.4 Hz, 1H), 7.14-7.08 (m, 2H), 7.04-6.98 (m, 2H), 6.93 (dd, J=8.1, 2.4 Hz, 1H), 3.71 (s, 3H), 2.95 (s, 3H), 2.83-2.72 (m, 1H), 2.71-2.56 (m, 4H). LCMS, [M+H]⁺=313.1.

68C. 3-Methoxy-3-(3-phenoxyphenyl)cyclobutanecarboxylic acid

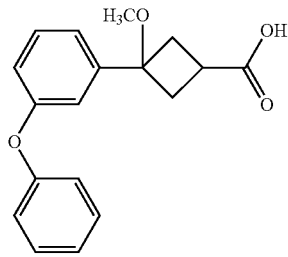 [SMILES: COC1(c2cccc(Oc3ccccc3)c2)CC(C(=O)O)C1]

To the solution of methyl 3-methoxy-3-(3-phenoxyphenyl) cyclobutanecarboxylate (172 mg, 0.551 mmol) in THF (2 mL) and water (2 mL) was added LiOH.H$_2$O (116 mg, 2.75 mmol). The mixture was stirred in at rt for 4 h. The reaction was neutralized with 1N HCl to pH=2-3. The mixture was extracted with EtOAc (4×5 mL), dried over MgSO$_4$, filtered and concentrated to afford the crude as a colorless oil. LCMS, [M–H]$^+$=297.2. This crude was used directly for next step.

68D. (3-Methoxy-3-(3-phenoxyphenyl)cyclobutyl)methanol

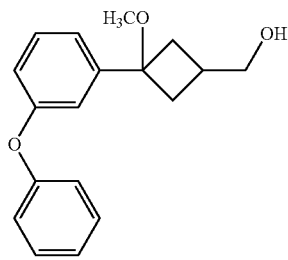 [SMILES: COC1(c2cccc(Oc3ccccc3)c2)CC(CO)C1]

Borane tetrahydrofuran complex (0.59 mL, 0.59 mmol) was added dropwise to a cold (−5° C.) solution of 3-methoxy-3-(3-phenoxyphenyl)cyclobutanecarboxylic acid (160 mg, 0.536 mmol) in THF (2 mL) and the resulting solution was stirred at −15 to 0° C. for 1 h. Additional Borane tetrahydrofuran complex (0.59 mL, 0.59 mmol) was added in and it was stirred at −15 to 0° C. for 1 h. The reaction mixture was then quenched with acetic acid (1.5 mL) and the organic solvent partially removed in vacuo. The residue was diluted with 5% of NaHCO$_3$ solution and the solution extracted with EtOAc (3×5 mL). The combined organic phase was washed with brine, dried over MgSO$_4$, filtered. The filtrate was concentrated to dryness to afford the crude (3-methoxy-3-(3-phenoxyphenyl) cyclobutyl)methanol (153 mg, 0.538 mmol, 100% yield) as a slightly yellow oil. LCMS, [M+H]$^+$=285. This crude was used directly for next step.

68E. 3-Methoxy-3-(3-phenoxyphenyl)cyclobutanecarbaldehyde

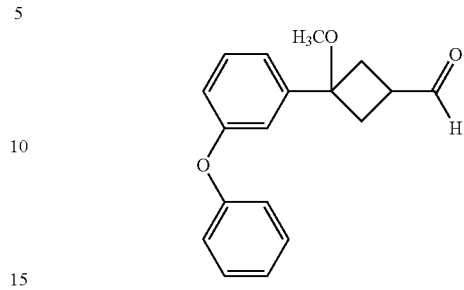

To a solution of (3-methoxy-3-(3-phenoxyphenyl)cyclobutyl)methanol (146 mg, 0.512 mmol) in DCM (3 mL) at 0° C. was added Dess-Martin Periodinane (217 mg, 0.512 mmol). The reaction was allowed to warmed to rt and stirred at rt for 2.5 h. The reaction solution was filtered through a plug of CELITE®, The DCM solution was concentrated in vacuo to give the crude. The crude was purified on an ISCO silica gel column (12 g, 0% to 60% of EtOAc in hexanes in 14 min) to afford the 3-methoxy-3-(3-phenoxyphenyl)cyclobutanecarbaldehyde (110 mg, 0.390 mmol, 76% yield) as a colorless oil. $^1$H NMR (500 MHz, chloroform-d) δ 9.80 (d, J=2.2 Hz, 1H), 7.39-7.30 (m, 3H), 7.17 (dt, J=7.7, 1.3 Hz, 1H), 7.14-7.08 (m, 2H), 7.04-7.00 (m, 2H), 6.94 (ddd, J=8.1, 2.5, 1.0 Hz, 1H), 2.95 (s, 3H), 2.83 (pd, J=8.3, 2.2 Hz, 1H), 2.65-2.55 (m, 4H).

68F. Methyl 3-(3-methoxy-3-(3-phenoxyphenyl)cyclobutyl)acrylate

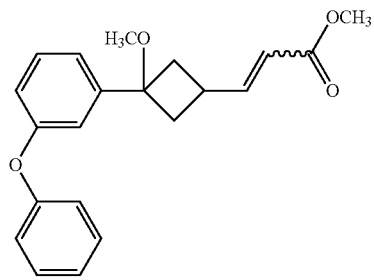 [SMILES: COC(=O)C=CC1CC(OC)(c2cccc(Oc3ccccc3)c2)C1]

A mixture of 3-methoxy-3-(3-phenoxyphenyl)cyclobutanecarbaldehyde (110 mg, 0.390 mmol) and methyl 2-(triphenylphosphoranylidene)acetate (391 mg, 1.169 mmol) in toluene (2 mL) was heated in a microwave reactor for 1 h at 130° C. The mixture was loaded onto an ISCO silica gel column (12 g; 0% to 40% of EtOAc in hexanes in 12 min) to yield methyl 3-(3-methoxy-3-(3-phenoxyphenyl)cyclobutyl) acrylate (112 mg, 0.331 mmol, 85% yield) as a colorless oil. LCMS, [M+NH$_4$]$^+$=356.1. This crude was used directly for next step.

68G. Methyl 3-(3-methoxy-3-(3-phenoxyphenyl)cyclobutyl)propanoate

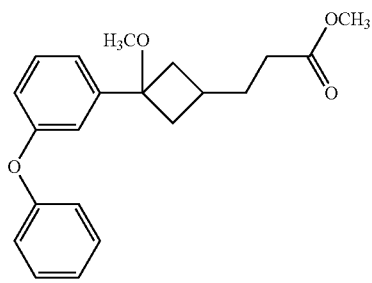 [SMILES: COC(=O)CCC1CC(OC)(c2cccc(Oc3ccccc3)c2)C1]

A solution of crude methyl 3-(3-methoxy-3-(3-phenoxyphenyl)cyclobutyl) acrylate (112 mg, 0.331 mmol) and 10% Pd/C (35 mg, 0.33 mmol) in THF (2 mL) and MeOH (1 mL) was stirred under 1 atm of Hydrogen for 2 h. The reaction was filtered through a plug of CELITE® and washed with DCM (4 mL). The filtrate was concentrated to afford the crude methyl 3-(3-methoxy-3-(3-phenoxyphenyl)cyclobutyl)propanoate (113 mg, 0.332 mmol, 100% yield) as a colorless oil. LCMS, $[M+NH_4]^+=358.2$. This crude was used directly for next step.

68H. 3-(3-Methoxy-3-(3-phenoxyphenyl)cyclobutyl) propanoic acid

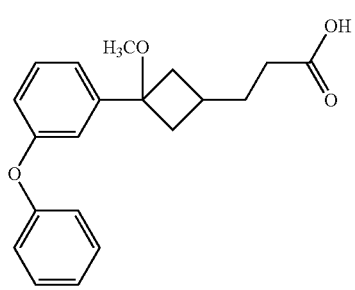 [SMILES: COC1(c2cccc(Oc3ccccc3)c2)CC(CCC(=O)O)C1]

To the solution of methyl 3-(3-methoxy-3-(3-phenoxyphenyl)cyclobutyl) propanoate (113 mg, 0.331 mmol)) in THF (2 mL) and water (2 mL) was added LiOH.H$_2$O (70 mg, 1.655 mmol) The mixture was stirred in at rt for 14 h. The reaction was neutralized with 1N HCl to pH=2-3. The mixture was extracted with EtOAc (4×5 mL), dried over MgSO$_4$, filtered and concentrated to afford the crude as a colorless oil. LCMS, $[M-H]^+=325.2$. This crude was used directly for next step.

68I. 3-(3-Methoxy-3-(3-phenoxyphenyl)cyclobutyl) propan-1-ol

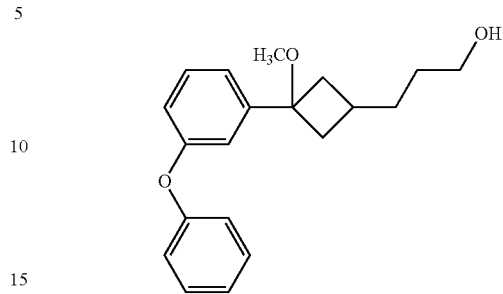

BH$_3$.THF (0.43 mL, 0.43 mmol) was added dropwise to a cold (−15° C.) solution of 3-(3-methoxy-3-(3-phenoxyphenyl)cyclobutyl)propanoic acid (108 mg, 0.331 mmol) in THF (2 mL) and the resulting solution was stirred at −15 to 0° C. for 1 h. Additional BH$_3$.THF (0.43 mL, 0.43 mmol) was added and the mixture was stirred at −5 to 0° C. for 30 min. The reaction mixture was then quenched with acetic acid (1.5 mL) and the reaction was warmed to rt. The mixture was diluted with 5% of NaHCO$_3$ solution (5 mL) and the solution extracted with EtOAc (3×5 mL). The combined organic phase was washed with brine, dried over MgSO$_4$, filtered. The filtrate was concentrated to dryness to afford the crude 3-(3-methoxy-3-(3-phenoxyphenyl)cyclobutyl)propan-1-ol (103 mg, 0.330 mmol, 100% yield) as a slightly colored oil. LCMS, $[M-H]^+=311.2$. This crude was used directly for next step.

68J. tert-Butyl 2-(3-(3-methoxy-3-(3-phenoxyphenyl)cyclobutyl)propoxy)acetate

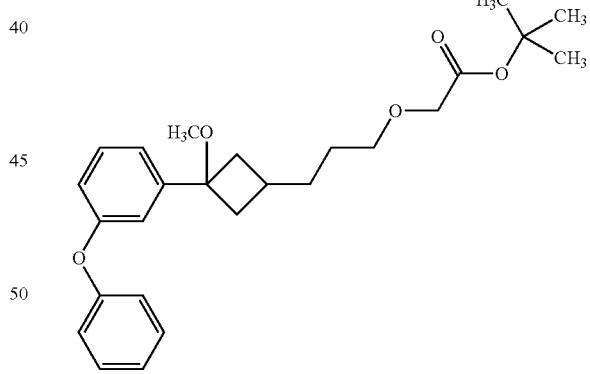

A solution of the crude 3-(3-methoxy-3-(3-phenoxyphenyl)cyclobutyl)propan-1-ol (0.103 g, 0.331 mmol) in toluene (1.5 mL) was cooled to 0° C. A 15 N aqueous solution of NaOH (0.22 mL) was added in, followed by tetrabutylammonium hydrogensulfate (0.034 g, 0.099 mmol). The mixture was stirred at 0° C. for 30 min. tert-Butyl 2-bromoacetate (0.20 mL, 1.324 mmol) was added in and the mixture was stirred for 72 h at rt. The reaction was diluted with water, extracted with EtOAc (3×10 mL). The combined organic layers were washed with brine (10 mL), dried over MgSO$_4$, filtered and evaporated in vacuo to afford the crude as a slightly yellow oil. LCMS, $[M+NH_4]^+=444.3$. This crude was used directly for next step.

Example 68

To the solution of crude tert-butyl 2-(3-(3-methoxy-3-(3-phenoxyphenyl) cyclobutyl)propoxy)acetate (141 mg, 0.331 mmol)) in THF (2 mL) and water (2 mL) was added LiOH.H$_2$O (70 mg, 1.65 mmol) The mixture was stirred in at rt for 18 h. The reaction was neutralized with 1N HCl to pH=2~3. The mixture was extracted with EtOAc (4×5 mL), dried over MgSO$_4$, filtered and concentrated to afford the crude. The crude material was purified via preparative LC/MS with the following conditions: Column: Waters XBridge C18, 19×200 mm, 5-μm particles; Mobile Phase A: 5:95 acetonitrile:water with 0.1% formic acid; Mobile Phase B: 95:5 acetonitrile:water with 0.1% formic acid; Gradient: 35-80% B over 20 minutes, then a 5-minute hold at 100% B; Flow: 20 mL/min. Fractions containing the desired product were combined and dried via centrifugal evaporation. The title compound was isolated in 42% yield (51.5 mg). LCMS, [M−H]$^+$=369.2. $^1$H NMR (500 MHz, DMSO-d$_6$) δ 7.40 (t, J=7.9 Hz, 3H), 7.22 (d, J=7.7 Hz, 1H), 7.15 (t, J=7.4 Hz, 1H), 7.02 (d, J=8.1 Hz, 3H), 6.91 (dd, J=8.0, 2.4 Hz, 1H), 3.89 (s, 2H), 3.62-3.08 (m, 3H), 2.81 (s, 3H), 2.48-2.43 (m, 1H), 1.83 (dq, J=15.1, 8.4, 7.4 Hz, 3H), 1.45 (h, J=6.9 Hz, 4H). HPLC-4: RT=1.51 min; HPLC-5: RT=2.08 min; purity=100%.

What is claimed is:

1. A compound of formula (I)

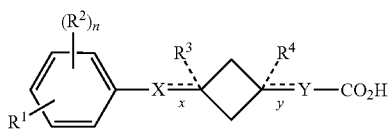

(I)

or a stereoisomer, a tautomer, a pharmaceutically acceptable salt, a polymorph, a solvate or a hydrate thereof, wherein:
- - - -  designates a single or double bond;
x and y can be both a single bond; when x is a double bond, then y is a single bond and R$^3$ is absent; when y is a double bond, then x is a single bond and R$^4$ is absent;
X is independently selected from: a bond, O, CH$_2$, —CH$_2$CH$_2$—, —OCH$_2$—, and —CH$_2$O—;
Y is independently a hydrocarbon linker substituted with 0-2 R$^a$, a hydrocarbon-heteroatom linker substituted with 0-2 R$^a$, or —(CH$_2$)$_{1-3}$-(O)$_{0-1}$-(CH$_2$)$_{1-3}$—(C$_{3-4}$ cycloalkyl substituted with 0-2 R$^a$)—(CH$_2$)$_{0-2}$—; wherein said hydrocarbon linker has one to six carbon atoms and may be straight or branched, saturated or unsaturated; and said hydrocarbon-heteroatom linker has one to four carbon atoms and one group selected from O, CO, S, NH, CONH, and NHCO;
W is independently selected from: a bond and 0;
R$^1$ is —W—R$^5$;
R$^2$, at each occurrence, is independently selected from: halogen, C$_{1-6}$ alkyl, C$_{1-4}$ alkoxy, C$_{1-4}$ alkylthio, C$_{1-4}$ haloalkyl, C$_{1-6}$ haloalkoxy, and C$_{1-4}$ haloalkylthio;
R$^3$ and R$^4$, at each occurrence, are independently selected from: H, C$_{1-4}$ alkyl, and C$_{1-4}$ alkoxy;
R$^3$ may combine with X to form a 3- to 4 carbocycle;
R$^4$ may combine with Y to form a 3- to 4 carbocycle;
R$^5$ is independently selected from: C$_{3-10}$ carbocycle, pyridyl, thiazolyl and dihydrobenzofuranyl; wherein each moiety is substituted with 0-1 R$^6$ and 0-3 R$^7$;
R$^6$ is independently selected from: unsubstituted C$_{1-6}$ alkyl, C$_{1-6}$ alkoxy, C$_{1-6}$ alkylthio, C$_{1-6}$ haloalkyl, C$_{1-6}$ haloalkoxy, C$_{1-6}$ haloalkylthio and —(X$_1$)$_{0-1}$-(CH$_2$)$_{0-2}$—R$^8$;
X$_1$ is independently selected from: O, S, NH and CO;
R$^7$, at each occurrence, is independently selected from: halogen, unsubstituted C$_{1-4}$ alkyl and C$_{1-4}$ alkoxy;
R$^8$ is independently selected from: C$_{3-6}$ carbocycle and a 5- to 6-membered heterocycle comprising carbon atoms and 1-4 heteroatoms selected from N, NR$^b$, O, and S; wherein said carbocycle and heterocycle are substituted with 0-3 R$^c$;
R$^a$, at each occurrence, is independently selected from: halogen, OH, C$_{1-4}$ alkyl, C$_{1-4}$ haloalkyl, and C$_{1-4}$ alkoxy;
R$^b$, at each occurrence, is independently selected from: H, C$_{1-4}$ alkyl, and —(CH$_2$)$_{0-2}$-phenyl;
R$^c$, at each occurrence, is independently selected from: halogen, C$_{1-4}$ alkyl, C$_{1-4}$ alkoxy, C$_{1-4}$ alkylthio, C$_{1-4}$ haloalkyl, C$_{1-4}$ haloalkoxy, and COPh; and
n is independently 0, 1, or 2.

2. A compound of Formula (II):

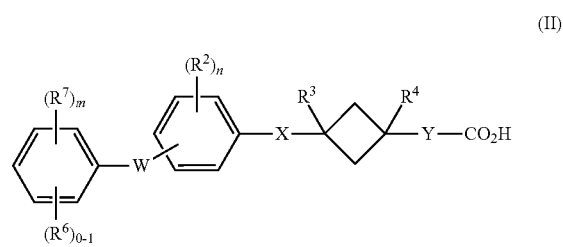

(II)

or a stereoisomer, a tautomer, a pharmaceutically acceptable salt, a polymorph, a solvate or a hydrate thereof, wherein:
X is independently selected from: a bond, O, CH$_2$, —OCH$_2$—, and —CH$_2$O—;
Y is independently selected from: —(CH$_2$)$_{0-3}$O(CH$_2$)$_{1-2}$—, —(CH$_2$)$_{1-3}$—,

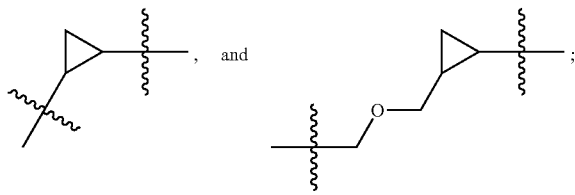 [SMILES: *C1CC1* ; *COCC1CC1*]

W is independently selected from: a bond and O;
R$^2$, at each occurrence, is independently selected from: halogen, C$_{1-4}$ alkyl, and C$_{1-4}$ alkoxy;
R$^3$ and R$^4$, at each occurrence, are independently selected from: H, C$_{1-4}$ alkyl, and C$_{1-4}$ alkoxy;
R$^6$ is independently selected from: C$_{1-4}$ alkoxy, C$_{1-4}$ haloalkoxy, Bn, and —(O)$_{0-1}$—R$^8$;
R$^7$, at each occurrence, is independently selected from: halogen, C$_{1-4}$ alkyl, and C$_{1-4}$ alkoxy;
R$^8$ is independently selected from: C$_{3-6}$ cycloalkyl, phenyl, tetrahydropyranyl, oxadiazolyl, thiazolyl, pyridyl, and pyridazinyl; wherein each moiety is substituted with 0-2 R$^c$;

R$^c$, at each occurrence, is independently selected from: halogen, C$_{1-4}$ alkyl, C$_{1-4}$ alkoxy, C$_{1-4}$ alkylthio, C$_{1-4}$ haloalkyl, C$_{1-4}$ haloalkoxy, and COPh; and m and n, at each occurrence, are independently 0, 1, or 2.

3. A compound according to claim 2 or a stereoisomer, a tautomer, a pharmaceutically acceptable salt, a polymorph, a solvate or a hydrate thereof, wherein:
Y is independently selected from: —(CH$_2$)$_{0-3}$O(CH$_2$)$_{1-2}$—, and —(CH$_2$)$_{1-3}$—;
W is O;
R$^3$ and R$^4$ are H; and
m and n, at each occurrence, are independently 0 or 1.

4. A compound according to claim 3 or a stereoisomer, a tautomer, a pharmaceutically acceptable salt, a polymorph, a solvate or a hydrate thereof, wherein:
R$^6$ is independently selected from: Bn and —(O)$_{0-1}$—R$^8$;
R$^8$ is independently selected from: phenyl and pyridyl; wherein each moiety is substituted with 0-2 R$^c$; and
R$^c$, at each occurrence, is independently selected from: halogen, C$_{1-4}$ alkyl, C$_{1-4}$ alkoxy, C$_{1-4}$ haloalkyl, and C$_{1-4}$ haloalkoxy.

5. A compound selected from the exemplified Examples 1 to 68, or a stereoisomer, a tautomer, or a pharmaceutically acceptable salt thereof.

6. A pharmaceutical composition, comprising a pharmaceutically acceptable carrier and a compound of claim 1, or a stereoisomer, a tautomer, or a pharmaceutically acceptable salt thereof.

7. The pharmaceutical composition according to claim 6, further comprising one or more other suitable therapeutic agents selected from: a dipeptidyl peptidase-IV inhibitor, a sodium-glucose transporter-2 inhibitor and a 11b-HSD-1 inhibitor.

8. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 1.

9. A pharmaceutical composition, comprising a pharmaceutically acceptable carrier and a compound of claim 2, or a stereoisomer, a tautomer, or a pharmaceutically acceptable salt thereof.

10. The pharmaceutical composition according to claim 9, further comprising one or more other suitable therapeutic agents selected from: a dipeptidyl peptidase-IV inhibitor, a sodium-glucose transporter-2 inhibitor and a 11b-HSD-1 inhibitor.

11. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 2.

12. A pharmaceutical composition, comprising a pharmaceutically acceptable carrier and a compound of claim 3, or a stereoisomer, a tautomer, or a pharmaceutically acceptable salt thereof.

13. The pharmaceutical composition according to claim 12, further comprising one or more other suitable therapeutic agents selected from: a dipeptidyl peptidase-IV inhibitor, a sodium-glucose transporter-2 inhibitor and a 11b-HSD-1 inhibitor.

14. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 3.

15. A pharmaceutical composition, comprising a pharmaceutically acceptable carrier and a compound of claim 4, or a stereoisomer, a tautomer, or a pharmaceutically acceptable salt thereof.

16. The pharmaceutical composition according to claim 15, further comprising one or more other suitable therapeutic agents selected from: a dipeptidyl peptidase-IV inhibitor, a sodium-glucose transporter-2 inhibitor and a 11b-HSD-1 inhibitor.

17. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 4.

18. A pharmaceutical composition, comprising a pharmaceutically acceptable carrier and a compound of claim 5, or a stereoisomer, a tautomer, or a pharmaceutically acceptable salt thereof.

19. The pharmaceutical composition according to claim 18, further comprising one or more other suitable therapeutic agents selected from: a dipeptidyl peptidase-IV inhibitor, a sodium-glucose transporter-2 inhibitor and a 11b-HSD-1 inhibitor.

20. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 5.

* * * * *